US012662512B2

(12) United States Patent (10) Patent No.: US 12,662,512 B2
Colella et al. (45) Date of Patent: Jun. 23, 2026

(54) CHIMERIC POLYPEPTIDES AND USES THEREOF

(71) Applicants:GENETHON, Evry-Courcouronnes (FR); UNIVERSITE D'EVRY VAL D'ESSONNE, Evry-Courcouronnes (FR); INSERM (INSTITUT NATIONAL DE LA SANTE ET DE LA RECHERCHE MEDICALE), Paris (FR); SORBONNE UNIVERSITE, PARIS (FR)

(72) Inventors: Pasqualina Colella, Naples (IT); Francesco Puzzo, Roggiano Gravina (IT); Federico Mingozzi, Philadelphia, PA (US)

(73) Assignees: GENETHON, Evry-Courcouronnes (FR); UNIVERSITE D'EVRY VAL D'ESSONNE, Evry-Courcouronnes (FR); INSERM (INSTITUT NATIONAL DE LA SANTE ET DE LA RECHERCHE MEDICALE), Paris (FR); SORBONNE UNIVERSITE, Paris (FR)

( * ) Notice: Subject to any disclaimer, the term of this patent is extended or adjusted under 35 U.S.C. 154(b) by 1017 days.

(21) Appl. No.: 17/770,641

(22) PCT Filed: Oct. 22, 2020

(86) PCT No.: PCT/EP2020/079693
§ 371 (c)(1),
(2) Date: Apr. 21, 2022

(87) PCT Pub. No.: WO2021/078833
PCT Pub. Date: Apr. 29, 2021

(65) Prior Publication Data
US 2023/0033268 A1     Feb. 2, 2023

(30) Foreign Application Priority Data
Oct. 22, 2019     (EP) .................................... 19306372

(51) Int. Cl.
C07K 7/08         (2006.01)
A61P 3/00         (2006.01)
A61P 3/02         (2006.01)
C12N 15/86        (2006.01)

(52) U.S. Cl.
CPC ................ C07K 7/083 (2013.01); A61P 3/00 (2018.01); C12N 15/86 (2013.01)

(58) Field of Classification Search
None
See application file for complete search history.

(56) References Cited

U.S. PATENT DOCUMENTS 8,252,748 B2     8/2012  Mazella et al.

FOREIGN PATENT DOCUMENTS

| EP | 3293259 A1 * | 3/2018 | ............... A61P 3/08 |
| WO | WO-2004064750 A2 * | 8/2004 | ............... A61P 3/00 |
| WO | WO 2009/103898 | 8/2009 | |
| WO | WO 2010/063122 | 6/2010 | |
| WO | WO 2016/025523 | 2/2016 | |
| WO | WO-2016025523 A1 * | 2/2016 | ............. A61P 43/00 |
| WO | WO 2016/210376 | 12/2016 | |

OTHER PUBLICATIONS

NCBI Reference Sequence: XM_003783379.3: Predicted: Otolemur garnettii neurotensin (NTS), mRNA. Jan. 12, 2018 (Year: 2018).*
Iwabuchi H, Komori S, Ohashi H, Kimura S. The amino acid sequence of a smooth muscle-contracting peptide from chicken rectum. Identity to chicken neurotensin. Jpn J Pharmacol. Aug. 1987;44(4):455-9. (Year: 1987).*
GenBank Accession A28505 (https://www.ncbi.nlm.nih.gov/protein/ P13724). Downloaded on Sep. 28, 2025. (Year: 2025).*
Mazella, J. et al. "Spadin, a Sortilin-Derived Peptide, Targeting Rodent TREK-1 Channels: A New Concept in the Antidepressant Drug Design" *PLoS Biology*, Apr. 2010, pp. 1-17, vol. 8, Issue 4, e1000355.
Williamson, P. T. F. et al. "Expression and Purification of Recombinant Neurotensin in *Escherichia coli*" *Protein Expression and Purification*, 2000, pp. 271-275, vol. 19, No. 2.
Yi, X. et al. "Agile delivery of protein therapeutics to CNS" *Journal of Controlled Release*, 2014, pp. 637-663, vol. 190.
Written Opinion in International Application No. PCT/EP2020/ 079693, Nov. 30, 2020, pp. 1-10.
Kido, J. et al. "Gene therapy for lysosomal storage diseases: Current clinical trial prospects" *Frontiers in Genetics*, Jan. 13, 2023, pp. 1-16, vol. 14, No. 1064924.
Marques, A. R. A. et al. "Lysosomal storage disorders—challenges, concepts and avenues for therapy: beyond rare diseases" Journal of Cell Science, Jan. 16, 2019, pp. 1-14, vol. 132, No. 2, jcs221739.
Sun, A. "Lysosomal storage disease overview" Ann Transl Med, Dec. 2018, pp. 1-14, vol. 6, No. 24.

* cited by examiner

*Primary Examiner* — Nicole Kinsey White
*Assistant Examiner* — Ruixue Wang
(74) *Attorney, Agent, or Firm* — SALIWANCHIK, LLOYD & EISENSCHENK

(57) ABSTRACT

The present invention relates to a nucleic acid molecule encoding a chimeric polypeptide comprising a peptide of interest fused to one or more heterologous moieties, wherein at least one of the heterologous moieties is a ligand of the Sortilin receptor. The invention also relates to a chimeric polypeptide encoded by said nucleic acid molecule and uses thereof.

Figure 1:
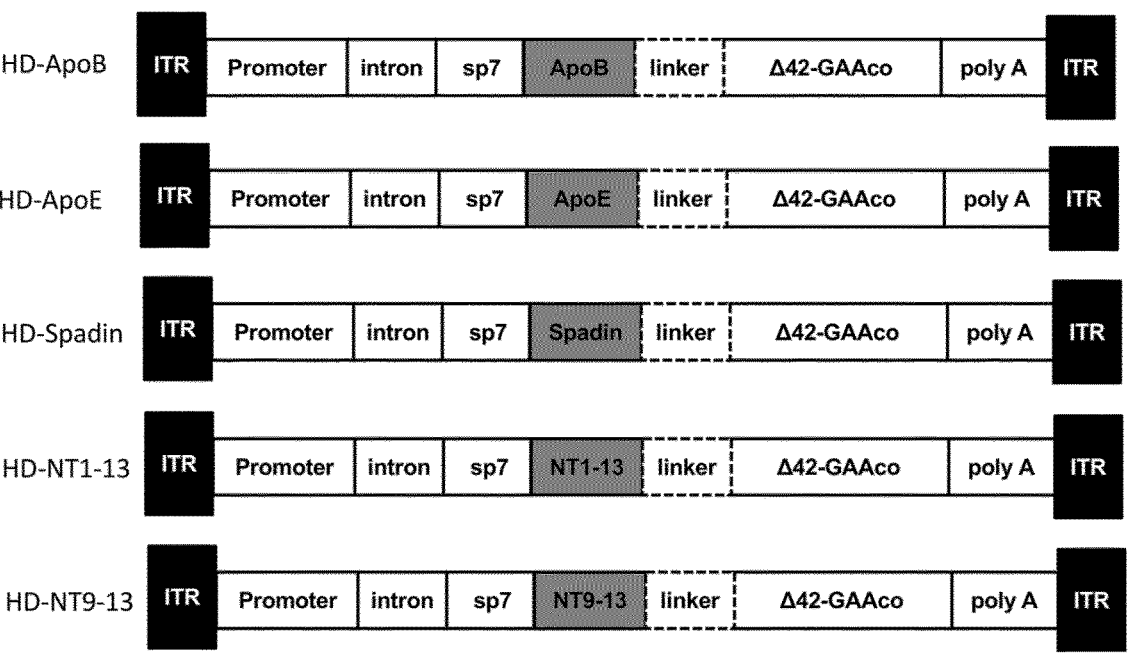

13 Claims, 6 Drawing Sheets
Specification includes a Sequence Listing.

A

B

A

B

C

A

B

SEQUENCE LISTING

<160> NUMBER OF SEQ ID NOS: 69

<210> SEQ ID NO 1
<211> LENGTH: 2859
<212> TYPE: DNA
<213> ORGANISM: Homo sapiens

<400> SEQUENCE: 1

```
atgggagtga ggcacccgcc ctgctcccac cggctcctgg ccgtctgcgc cctcgtgtcc        60
ttggcaaccg ctgcactcct ggggcacatc ctactccatg atttcctgct ggttccccga       120
gagctgagtg gctcctcccc agtcctggag gagactcacc cagctcacca gcagggagcc       180
agcagaccag ggccccggga tgcccaggca caccccggcc gtcccagagc agtgcccaca       240
cagtgcgacg tcccccccaa cagccgcttc gattgcgccc ctgacaaggc catcacccag       300
gaacagtgcg aggcccgcgg ctgctgctac atccctgcaa agcaggggct gcagggagcc       360
cagatggggc agccctggtg cttcttccca cccagctacc ccagctacaa gctggagaac       420
ctgagctcct ctgaaatggg ctacacggcc accctgaccc gtaccacccc caccttcttc       480
cccaaggaca tcctgaccct gcggctggac gtgatgatgg agactgagaa ccgcctccac       540
ttcacgatca aagatccagc taacaggcgc tacgaggtgc ccttggagac cccgcgtgtc       600
cacagccggg caccgtcccc actctacagc gtggagttct ccgaggagcc cttcggggtg       660
atcgtgcacc ggcagctgga cggccgcgtg ctgctgaaca cgacggtggc gcccctgttc       720
tttgcggacc agttccttca gctgtccacc tcgctgccct cgcagtatat cacaggcctc       780
gccgagcacc tcagtcccct gatgctcagc accagctgga ccaggatcac cctgtggaac       840
cgggaccttg cgcccacgcc cggtgcgaac ctctacgggt ctcacccttt ctacctggcg       900
ctggaggacg gcgggtcggc acacggggtg ttcctgctaa acagcaatgc catggatgtg       960
gtcctgcagc cgagccctgc ccttagctgg aggtcgacag gtgggatcct ggatgtctac      1020
atcttcctgg gcccagagcc caagagcgtg gtgcagcagt acctggacgt tgtgggatac      1080
ccgttcatgc cgccatactg gggcctgggc ttccacctgt gccgctgggg ctactcctcc      1140
accgctatca cccgccaggt ggtggagaac atgaccaggg cccacttccc cctggacgtc      1200
caatggaacg acctggacta catggactcc cggagggact tcacgttcaa caaggatggc      1260
ttccgggact ccccggccat ggtgcaggag ctgcaccagg cggccggcg ctacatgatg      1320 atcgtggatc ctgccatcag cagctcgggc cctgccggga gctacaggcc ctacgacgag      1380
ggtctgcgga gggggttttt catcaccaac gagaccggcc agccgctgat gggaaggta      1440 tggcccgggt ccactgcctt ccccgacttc accaacccca gccctggc ctggtggggag      1500 gacatggtgg ctgagttcca tgaccaggtg cccttcgacg gcatgtggat tgacatgaac      1560
gagccttcca acttcatcag aggctctgag acggctgcc ccaacaatga gctggagaac      1620
ccaccctacg tgcctggggt ggttggggg accctccagg cggccaccat ctgtgcctcc      1680
agccaccagt ttctctccac acactacaac ctgcacaacc tctacggcct gaccgaagcc      1740
atcgcctccc acagggcgct ggtgaaggct cgggggacac gcccatttgt gatctcccgc      1800
tcgacctttg ctggccacgg ccgatacgcc ggcactgga cggggacgt gtggagctcc      1860 tgggagcagc tcgcctcctc cgtgccagaa atcctgcagt ttaacctgct ggggtgcct      1920 ctggtcgggg ccgacgtctg cggcttcctg ggcaacacct cagaggagct gtgtgtgcgc      1980
tggacccagc tggggccctt ctacccttc atgcggaacc acaacagcct gctcagtctg      2040
ccccaggagc cgtacagctt cagcgagccg gcccagcagg ccatgaggaa ggccctcacc      2100
```

-continued

```
ctgcgctacg cactcctccc ccacctctac acactgttcc accaggccca cgtcgcgggg       2160
gagaccgtgg cccggcccct cttcctggag ttccccaagg actctagcac ctggactgtg       2220
gaccaccagc tcctgtgggg ggaggccctg ctcatcaccc cagtgctcca ggccgggaag       2280
gccgaagtga ctggctactt ccccttgggc acatggtacg acctgcagac ggtgccaata       2340
gaggcccttg gcagcctccc acccccacct gcagctcccc gtgagccagc catccacagc       2400
gaggggcagt gggtgacgct gccggccccc ctggacacca tcaacgtcca cctccgggct       2460
gggtacatca tcccctgca gggccctggc ctcacaacca cagagtcccg ccagcagccc        2520
atggccctgg ctgtggccct gaccaagggg ggagaggccc gaggggagct gttctgggac       2580
gatggagaga gcctggaagt gctggagcga ggggcctaca cacaggtcat cttcctggcc       2640
aggaataaca cgatcgtgaa tgagctggta cgtgtgacca gtgagggagc tggcctgcag       2700
ctgcagaagg tgactgtcct gggcgtggcc acggcgcccc agcaggtcct ctccaacggt       2760
gtccctgtct ccaacttcac ctacagcccc gacaccaagg tcctggacat ctgtgtctcg       2820
ctgttgatgg gagagcagtt tctcgtcagc tggtgttag                              2859
```

```
<210> SEQ ID NO 2
<211> LENGTH: 2778
<212> TYPE: DNA
<213> ORGANISM: artificial
<220> FEATURE:
<223> OTHER INFORMATION: hGAAco1 w/o sp

<400> SEQUENCE: 2
```

```
ggccatatcc tgctgcacga ctttctacta gtgcccagag agctgagcgg cagctctccc       60
gtgctggaag aaacacaccc tgcccatcag cagggcgcct ctagacctgg acctagagat       120
gcccaggccc accccggcag acctagagct gtgcctaccc agtgtgacgt gccccccaac       180
agcagattcg actgcgcccc tgacaaggcc atcacccagg aacagtgcga ggccagaggc       240
tgctgctaca tccctgccaa gcagggactg cagggcgctc agatgggaca gccctggtgc       300
ttcttcccac cctcctaccc cagctacaag ctggaaaacc tgagcagcag cgagatgggc       360
tacaccgcca ccctgaccag aaccaccccc acattcttcc caaaggacat cctgaccctg       420
cggctggacg tgatgatgga aaccgagaac cggctgcact tcaccatcaa ggaccccgcc       480
aatcggagat acgaggtgcc cctggaaacc ccccacgtgc actctagagc ccccagccct       540
ctgtacagcg tggaattcag cgaggaaccc ttcggcgtga tcgtgcggag acagctggat       600
ggcagagtgc tgctgaacac caccgtggcc cctctgttct tcgccgacca gttcctgcag       660
ctgagcacca gcctgcccag ccagtacatc acaggactgg ccgagcacct gagccccctg       720
atgctgagca tcctggacc ccggatcacc ctgtggaaca gggatctggc ccctacccct       780
ggcgccaatc tgtacggcag ccacccttttc tacctggccc tggaagatgg cggatctgcc       840 cacgagtgt ttctgctgaa ctccaacgcc atggacgtgg tgctgcagcc tagccctgcc       900
ctgtcttgga gaagcacagg cggcatcctg gatgtgtaca tctttctggg ccccgagccc       960
aagagcgtgg tgcagcagta tctggatgtc gtgggctacc ccttcatgcc ccctactgg       1020 ggcctgggat ccacctgtg cagatggggc tactccagca ccgccatcac cagacaggtg       1080
gtggaaaaca tgaccagagc ccacttccca ctggatgtgc agtggaacga cctggactac       1140
atggacagca cgggactt caccttcaac aaggacggct ccgggactt ccccgccatg       1200 gtgcaggaac tgcatcaggg cggcagacgg tacatgatga tcgtggatcc cgccatcagc       1260
```

```
tcctctggcc ctgccggctc ttacagaccc tacgacgagg gcctgcggag aggcgtgttc      1320
atcaccaacg agacaggcca gcccctgatc ggcaaagtgt ggcctggcag cacagccttc      1380
cccgacttca ccaatcctac cgccctggct tggtgggagg acatggtggc cgagttccac      1440
gaccaggtgc ccttcgacgg catgtggatc gacatgaacg agcccagcaa cttcatccgg      1500
ggcagcgagg atggctgccc caacaacgaa ctggaaaatc ccccttacgt gcccggcgtc      1560
gtgggcggaa cactgcaggc cgctacaatc tgtgccagca gccaccagtt tctgagcacc      1620
cactacaacc tgcacaacct gtacggcctg accgaggcca ttgccagcca ccgcgctctc      1680
gtgaaagcca gaggcacacg gcccttcgtg atcagcagaa gcacctttgc cggccacggc      1740
agatacgccg gacattggac tggcgacgtg tggtcctctt gggagcagct ggcctctagc      1800
gtgcccgaga tcctgcagtt caatctgctg ggcgtgccac tcgtgggcgc cgatgtgtgt      1860
ggcttcctgg gcaacacctc cgaggaactg tgtgtgcggt ggacacagct gggcgccttc      1920
taccctttca tgagaaacca caacagcctg ctgagcctgc cccaggaacc ctacagcttt      1980
agcgagcctg cacagcaggc catgcggaag gccctgacac tgagatacgc tctgctgccc      2040
cacctgtaca ccctgtttca ccaggcccat gtggccggcg agacagtggc cagacctctg      2100
tttctggaat cccccaagga cagcagcacc tggaccgtgg accatcagct gctgtgggga      2160
gaggctctgc tgattacccc agtgctgcag gcaggcaagg ccgaagtgac cggctacttt      2220
cccctgggca cttggtacga cctgcagacc gtgcctgtgg aagccctggg atctctgcct      2280
ccacctcctg ccgctcctag agagcctgcc attcactctg agggccagtg ggtcacactg      2340 cctgccccc tggataccat caacgtgcac ctgagggccg gctacatcat accactgcag      2400
ggacctggcc tgaccaccac cgagtctaga cagcagccaa tggccctggc cgtggccctg      2460
accaaaggcg agaagctag gggcgagctg ttctgggacg atggcgagag cctggaagtg      2520
ctggaaagag gcgcctatac ccaagtgatc ttcctggccc ggaacaacac catcgtgaac      2580
gagctggtgc gcgtgacctc tgaaggcgct ggactgcagc tgcagaaagt gaccgtgctg      2640
ggagtggcca cagcccctca gcaggtgctg tctaatggcg tgcccgtgtc caacttcacc      2700
tacagccccg acaccaaggt gctggacatc tgcgtgtcac tgctgatggg agagcagttt      2760
ctggtgtcct ggtgctga                                                     2778
```

<210> SEQ ID NO 3
<211> LENGTH: 2778
<212> TYPE: DNA
<213> ORGANISM: artificial
<220> FEATURE:
<223> OTHER INFORMATION: hGAAco2 w/o sp

<400> SEQUENCE: 3

```
ggacacatcc tgctgcacga cttcctgttg gtgcctagag agctgagcgg atcatcccca       60
gtgctggagg agactcatcc tgctcaccaa cagggagctt ccagaccagg accgagagac      120
gcccaagccc atcctggtag accaagagct gtgcctaccc aatgcgacgt gccacccaac      180
tcccgattcg actgcgcgcc agataaggct attacccaag agcagtgtga agccagaggt      240
tgctgctaca tccagcgaa gcaaggattg caaggcgccc aaatgggaca ccttggtgt      300 ttcttccccc cttcgtaccc atcatataaa ctcgaaaacc tgtcctcttc ggaaatgggt      360
tatactgcca ccctcaccag aactactcct actttcttcc cgaaagacat cttgaccttg      420
aggctggacg tgatgatgga gactgaaaac cggctgcatt tcactatcaa agatcctgcc      480
aatcggcgat acgaggtccc tctggaaacc cctcacgtgc actcacgggc tccttctccg      540
```

```
ctttactccg tcgaattctc tgaggaaccc ttcggagtga tcgttagacg ccagctggat      600
ggtagagtgc tgttgaacac tactgtggcc ccacttttct tcgctgacca gtttctgcaa      660
ctgtccactt ccctgccatc ccagtacatt actggactcg ccgaacacct gtcgccactg      720
atgctctcga cctcttggac tagaatcact ttgtggaaca gagacttggc ccctactccg      780
ggagcaaatc tgtacggaag ccaccctttt tacctggcgc tcgaagatgg cggatccgct      840
cacggagtgt tcctgctgaa tagcaacgca atggacgtgg tgctgcaacc ttcccctgca      900
ctcagttgga gaagtaccgg gggtattctg gacgtgtaca tcttcctcgg accagaaccc      960
aagagcgtgg tgcagcaata tctgacgtgt gtcggatacc cttttatgcc tccttactgg     1020
ggactgggat tccacctttg ccgttggggc tactcatcca ccgccattac cagacaggtg     1080
gtggagaata tgaccagagc ccacttccct ctcgacgtgc agtggaacga tctgactat      1140 atggactccc ggagagattt caccttcaac aaggacgggt tccgcgattt tcccgcgatg     1200
gttcaagagc tccaccaggg tggtcgaaga tatatgatga tcgtcgaccc agccatttcg     1260
agcagcggac ccgctggatc ttatagacct tacgacgaag gccttaggag aggagtgttc     1320
atcacaaacg agactggaca gcctttgatc ggtaaagtgt ggcctggatc aaccgccttt     1380 cctgactta ccaatcccac tgccttggct tggtgggagg acatggtggc cgaattccac      1440
gaccaagtcc cctttgatgg aatgtggatc gatatgaacg aaccaagcaa ttttatcaga     1500
ggttccgaag acggttgccc caacaacgaa ctggaaaacc ctccttatgt gcccggagtc     1560
gtgggcggaa cattacaggc cgcgactatt tgcgccagca gccaccaatt cctgtccact     1620
cactacaacc tccacaacct ttatggatta accgaagcta ttgcaagtca cagggctctg     1680
gtgaaggcta gagggactag gccctttgtg atctcccgat ccacctttgc cggacacggg     1740
agatacgccg gtcactggac tggtgacgtg tggagctcat gggaacaact ggcctcctcc     1800
gtgccggaaa tcttacagtt caaccttctg ggtgtccctc ttgtcggagc agacgtgtgt     1860
gggtttcttg gtaacacctc cgaggaactg tgtgtgcgct ggactcaact gggtgcattc     1920
tacccattca tgagaaacca caactccttg ctgtccctgc acaagagcc ctactcgttc      1980 agcgagcctg cacaacaggc tatgcggaag gcactgaccc tgagatacgc cctgcttcca     2040
cacttataca ctctcttcca tcaagcgcat gtggcaggag aaaccgttgc aaggcctctt     2100
ttccttgaat tccccaagga ttcctcgact tggacggtgg atcatcagct gctgtgggga     2160
gaagctctgc tgattactcc agtgttgcaa gccggaaaag ctgaggtgac cggatacttt     2220
ccgctgggaa cctggtacga cctccagact gtccctgttg aagcccttgg atcactgcct     2280
ccgcctccgg cagctccacg cgaaccagct atacattccg agggacagtg ggttacatta     2340
ccagctcctc tggacacaat caacgtccac ttaagagctg gctacattat ccctctgcaa     2400
ggaccaggac tgactacgac cgagagcaga cagcagccaa tggcactggc tgtggctctg     2460
accaagggag gggaagctag aggagaactc ttctgggatg atggggagtc ccttgaagtg     2520
ctggaaagag gcgcttacac tcaagtcatt ttccttgcac ggaacaacac cattgtgaac     2580
gaattggtgc gagtgaccag cgaaggagct ggacttcaac tgcagaaggt cactgtgctc     2640
ggagtggcta ccgctcctca gcaagtgctg tcgaatggag tccccgtgtc aaactttacc     2700
tactcccctg acactaaggt gctcgacatt tgcgtgtccc tcctgatggg agagcagttc     2760
cttgtgtcct ggtgttga                                                   2778
```

<210> SEQ ID NO 4

<211> LENGTH: 925
<212> TYPE: PRT
<213> ORGANISM: artificial
<220> FEATURE:
<223> OTHER INFORMATION: hGAAwt w/o sp

<400> SEQUENCE: 4

```
Gly His Ile Leu Leu His Asp Phe Leu Leu Val Pro Arg Glu Leu Ser
1               5                   10                  15

Gly Ser Ser Pro Val Leu Glu Glu Thr His Pro Ala His Gln Gln Gly
            20                  25                  30

Ala Ser Arg Pro Gly Pro Arg Asp Ala Gln Ala His Pro Gly Arg Pro
        35                  40                  45

Arg Ala Val Pro Thr Gln Cys Asp Val Pro Pro Asn Ser Arg Phe Asp
    50                  55                  60

Cys Ala Pro Asp Lys Ala Ile Thr Gln Glu Gln Cys Glu Ala Arg Gly
65                  70                  75                  80

Cys Cys Tyr Ile Pro Ala Lys Gln Gly Leu Gln Gly Ala Gln Met Gly
                85                  90                  95

Gln Pro Trp Cys Phe Phe Pro Pro Ser Tyr Pro Ser Tyr Lys Leu Glu
            100                 105                 110

Asn Leu Ser Ser Ser Glu Met Gly Tyr Thr Ala Thr Leu Thr Arg Thr
        115                 120                 125

Thr Pro Thr Phe Phe Pro Lys Asp Ile Leu Thr Leu Arg Leu Asp Val
    130                 135                 140

Met Met Glu Thr Glu Asn Arg Leu His Phe Thr Ile Lys Asp Pro Ala
145                 150                 155                 160

Asn Arg Arg Tyr Glu Val Pro Leu Glu Thr Pro His Val His Ser Arg
                165                 170                 175

Ala Pro Ser Pro Leu Tyr Ser Val Glu Phe Ser Glu Glu Pro Phe Gly
            180                 185                 190

Val Ile Val Arg Arg Gln Leu Asp Gly Arg Val Leu Leu Asn Thr Thr
            195                 200                 205

Val Ala Pro Leu Phe Phe Ala Asp Gln Phe Leu Gln Leu Ser Thr Ser
    210                 215                 220

Leu Pro Ser Gln Tyr Ile Thr Gly Leu Ala Glu His Leu Ser Pro Leu
225                 230                 235                 240

Met Leu Ser Thr Ser Trp Thr Arg Ile Thr Leu Trp Asn Arg Asp Leu
                245                 250                 255

Ala Pro Thr Pro Gly Ala Asn Leu Tyr Gly Ser His Pro Phe Tyr Leu
            260                 265                 270

Ala Leu Glu Asp Gly Gly Ser Ala His Gly Val Phe Leu Leu Asn Ser
        275                 280                 285

Asn Ala Met Asp Val Val Leu Gln Pro Ser Pro Ala Leu Ser Trp Arg
        290                 295                 300

Ser Thr Gly Gly Ile Leu Asp Val Tyr Ile Phe Leu Gly Pro Glu Pro
305                 310                 315                 320

Lys Ser Val Val Gln Gln Tyr Leu Asp Val Val Gly Tyr Pro Phe Met
                325                 330                 335

Pro Pro Tyr Trp Gly Leu Gly Phe His Leu Cys Arg Trp Gly Tyr Ser
            340                 345                 350

Ser Thr Ala Ile Thr Arg Gln Val Val Glu Asn Met Thr Arg Ala His
        355                 360                 365

Phe Pro Leu Asp Val Gln Trp Asn Asp Leu Asp Tyr Met Asp Ser Arg
    370                 375                 380
```

-continued

```
Arg Asp Phe Thr Phe Asn Lys Asp Gly Phe Arg Asp Phe Pro Ala Met
385                 390                 395                 400

Val Gln Glu Leu His Gln Gly Gly Arg Arg Tyr Met Met Ile Val Asp
                405                 410                 415

Pro Ala Ile Ser Ser Ser Gly Pro Ala Gly Ser Tyr Arg Pro Tyr Asp
                420                 425                 430

Glu Gly Leu Arg Arg Gly Val Phe Ile Thr Asn Glu Thr Gly Gln Pro
                435                 440                 445

Leu Ile Gly Lys Val Trp Pro Gly Ser Thr Ala Phe Pro Asp Phe Thr
                450                 455                 460

Asn Pro Thr Ala Leu Ala Trp Trp Glu Asp Met Val Ala Glu Phe His
465                 470                 475                 480

Asp Gln Val Pro Phe Asp Gly Met Trp Ile Asp Met Asn Glu Pro Ser
                485                 490                 495

Asn Phe Ile Arg Gly Ser Glu Asp Gly Cys Pro Asn Asn Glu Leu Glu
                500                 505                 510

Asn Pro Pro Tyr Val Pro Gly Val Val Gly Gly Thr Leu Gln Ala Ala
                515                 520                 525

Thr Ile Cys Ala Ser Ser His Gln Phe Leu Ser Thr His Tyr Asn Leu
                530                 535                 540

His Asn Leu Tyr Gly Leu Thr Glu Ala Ile Ala Ser His Arg Ala Leu
545                 550                 555                 560

Val Lys Ala Arg Gly Thr Arg Pro Phe Val Ile Ser Arg Ser Thr Phe
                565                 570                 575

Ala Gly His Gly Arg Tyr Ala Gly His Trp Thr Gly Asp Val Trp Ser
                580                 585                 590

Ser Trp Glu Gln Leu Ala Ser Ser Val Pro Glu Ile Leu Gln Phe Asn
                595                 600                 605

Leu Leu Gly Val Pro Leu Val Gly Ala Asp Val Cys Gly Phe Leu Gly
                610                 615                 620

Asn Thr Ser Glu Glu Leu Cys Val Arg Trp Thr Gln Leu Gly Ala Phe
625                 630                 635                 640

Tyr Pro Phe Met Arg Asn His Asn Ser Leu Leu Ser Leu Pro Gln Glu
                645                 650                 655

Pro Tyr Ser Phe Ser Glu Pro Ala Gln Gln Ala Met Arg Lys Ala Leu
                660                 665                 670

Thr Leu Arg Tyr Ala Leu Leu Pro His Leu Tyr Thr Leu Phe His Gln
                675                 680                 685

Ala His Val Ala Gly Glu Thr Val Ala Arg Pro Leu Phe Leu Glu Phe
                690                 695                 700

Pro Lys Asp Ser Ser Thr Trp Thr Val Asp His Gln Leu Leu Trp Gly
705                 710                 715                 720

Glu Ala Leu Leu Ile Thr Pro Val Leu Gln Ala Gly Lys Ala Glu Val
                725                 730                 735

Thr Gly Tyr Phe Pro Leu Gly Thr Trp Tyr Asp Leu Gln Thr Val Pro
                740                 745                 750

Val Glu Ala Leu Gly Ser Leu Pro Pro Pro Ala Ala Pro Arg Glu
                755                 760                 765

Pro Ala Ile His Ser Glu Gly Gln Trp Val Thr Leu Pro Ala Pro Leu
                770                 775                 780

Asp Thr Ile Asn Val His Leu Arg Ala Gly Tyr Ile Ile Pro Leu Gln
785                 790                 795                 800
```

```
Gly Pro Gly Leu Thr Thr Thr Glu Ser Arg Gln Gln Pro Met Ala Leu
            805             810             815

Ala Val Ala Leu Thr Lys Gly Gly Glu Ala Arg Gly Glu Leu Phe Trp
            820             825             830

Asp Asp Gly Glu Ser Leu Glu Val Leu Glu Arg Gly Ala Tyr Thr Gln
        835             840             845

Val Ile Phe Leu Ala Arg Asn Asn Thr Ile Val Asn Glu Leu Val Arg
    850             855             860

Val Thr Ser Glu Gly Ala Gly Leu Gln Leu Gln Lys Val Thr Val Leu
865             870             875             880

Gly Val Ala Thr Ala Pro Gln Gln Val Leu Ser Asn Gly Val Pro Val
            885             890             895

Ser Asn Phe Thr Tyr Ser Pro Asp Thr Lys Val Leu Asp Ile Cys Val
            900             905             910

Ser Leu Leu Met Gly Glu Gln Phe Leu Val Ser Trp Cys
            915             920             925
```

<210> SEQ ID NO 5
<211> LENGTH: 952
<212> TYPE: PRT
<213> ORGANISM: Homo sapiens

<400> SEQUENCE: 5

```
Met Gly Val Arg His Pro Pro Cys Ser His Arg Leu Leu Ala Val Cys
1               5               10              15

Ala Leu Val Ser Leu Ala Thr Ala Ala Leu Leu Gly His Ile Leu Leu
            20              25              30

His Asp Phe Leu Leu Val Pro Arg Glu Leu Ser Gly Ser Ser Pro Val
        35              40              45

Leu Glu Glu Thr His Pro Ala His Gln Gln Gly Ala Ser Arg Pro Gly
    50              55              60

Pro Arg Asp Ala Gln Ala His Pro Gly Arg Pro Arg Ala Val Pro Thr
65              70              75              80

Gln Cys Asp Val Pro Pro Asn Ser Arg Phe Asp Cys Ala Pro Asp Lys
            85              90              95

Ala Ile Thr Gln Glu Gln Cys Glu Ala Arg Gly Cys Cys Tyr Ile Pro
            100             105             110

Ala Lys Gln Gly Leu Gln Gly Ala Gln Met Gly Gln Pro Trp Cys Phe
            115             120             125

Phe Pro Pro Ser Tyr Pro Ser Tyr Lys Leu Glu Asn Leu Ser Ser Ser
        130             135             140

Glu Met Gly Tyr Thr Ala Thr Leu Thr Arg Thr Thr Pro Thr Phe Phe
145             150             155             160

Pro Lys Asp Ile Leu Thr Leu Arg Leu Asp Val Met Met Glu Thr Glu
            165             170             175

Asn Arg Leu His Phe Thr Ile Lys Asp Pro Ala Asn Arg Arg Tyr Glu
            180             185             190

Val Pro Leu Glu Thr Pro His Val His Ser Arg Ala Pro Ser Pro Leu
            195             200             205

Tyr Ser Val Glu Phe Ser Glu Glu Pro Phe Gly Val Ile Val Arg Arg
        210             215             220

Gln Leu Asp Gly Arg Val Leu Leu Asn Thr Thr Val Ala Pro Leu Phe
225             230             235             240

Phe Ala Asp Gln Phe Leu Gln Leu Ser Thr Ser Leu Pro Ser Gln Tyr
            245             250             255
```

-continued

```
Ile Thr Gly Leu Ala Glu His Leu Ser Pro Leu Met Leu Ser Thr Ser
        260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
        290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
                340                 345                 350

Gln Tyr Leu Asp Val Val Gly Tyr Pro Phe Met Pro Pro Tyr Trp Gly
                355                 360                 365

Leu Gly Phe His Leu Cys Arg Trp Gly Tyr Ser Ser Thr Ala Ile Thr
        370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
                420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Pro Tyr Asp Glu Gly Leu Arg Arg
        450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
                500                 505                 510

Asp Gly Met Trp Ile Asp Met Asn Glu Pro Ser Asn Phe Ile Arg Gly
                515                 520                 525

Ser Glu Asp Gly Cys Pro Asn Asn Glu Leu Glu Asn Pro Pro Tyr Val
        530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
                580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
        610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
        660                 665                 670
```

-continued

```
Asn His Asn Ser Leu Leu Ser Leu Pro Gln Glu Pro Tyr Ser Phe Ser
        675             680             685

Glu Pro Ala Gln Gln Ala Met Arg Lys Ala Leu Thr Leu Arg Tyr Ala
    690             695             700

Leu Leu Pro His Leu Tyr Thr Leu Phe His Gln Ala His Val Ala Gly
705             710             715             720

Glu Thr Val Ala Arg Pro Leu Phe Leu Glu Phe Pro Lys Asp Ser Ser
                725             730             735

Thr Trp Thr Val Asp His Gln Leu Leu Trp Gly Glu Ala Leu Leu Ile
            740             745             750

Thr Pro Val Leu Gln Ala Gly Lys Ala Glu Val Thr Gly Tyr Phe Pro
        755             760             765

Leu Gly Thr Trp Tyr Asp Leu Gln Thr Val Pro Val Glu Ala Leu Gly
    770             775             780

Ser Leu Pro Pro Pro Ala Ala Pro Arg Glu Pro Ala Ile His Ser
785             790             795             800

Glu Gly Gln Trp Val Thr Leu Pro Ala Pro Leu Asp Thr Ile Asn Val
            805             810             815

His Leu Arg Ala Gly Tyr Ile Ile Pro Leu Gln Gly Pro Gly Leu Thr
        820             825             830

Thr Thr Glu Ser Arg Gln Gln Pro Met Ala Leu Ala Val Ala Leu Thr
        835             840             845

Lys Gly Gly Glu Ala Arg Gly Glu Leu Phe Trp Asp Asp Gly Glu Ser
    850             855             860

Leu Glu Val Leu Glu Arg Gly Ala Tyr Thr Gln Val Ile Phe Leu Ala
865             870             875             880

Arg Asn Asn Thr Ile Val Asn Glu Leu Val Arg Val Thr Ser Glu Gly
            885             890             895

Ala Gly Leu Gln Leu Gln Lys Val Thr Val Leu Gly Val Ala Thr Ala
        900             905             910

Pro Gln Gln Val Leu Ser Asn Gly Val Pro Val Ser Asn Phe Thr Tyr
        915             920             925

Ser Pro Asp Thr Lys Val Leu Asp Ile Cys Val Ser Leu Leu Met Gly
    930             935             940

Glu Gln Phe Leu Val Ser Trp Cys
945             950
```

<210> SEQ ID NO 6
<211> LENGTH: 952
<212> TYPE: PRT
<213> ORGANISM: Homo sapiens

<400> SEQUENCE: 6

```
Met Gly Val Arg His Pro Pro Cys Ser His Arg Leu Leu Ala Val Cys
1               5               10              15

Ala Leu Val Ser Leu Ala Thr Ala Ala Leu Leu Gly His Ile Leu Leu
            20              25              30

His Asp Phe Leu Leu Val Pro Arg Glu Leu Ser Gly Ser Ser Pro Val
        35              40              45

Leu Glu Glu Thr His Pro Ala His Gln Gln Gly Ala Ser Arg Pro Gly
    50              55              60

Pro Arg Asp Ala Gln Ala His Pro Gly Arg Pro Arg Ala Val Pro Thr
65              70              75              80

Gln Cys Asp Val Pro Pro Asn Ser Arg Phe Asp Cys Ala Pro Asp Lys
                85              90              95
```

```
Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
            115                 120                 125

Phe Pro Pro Ser Tyr Pro Ser Tyr Lys Leu Glu Asn Leu Ser Ser Ser
        130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro Arg Val His Ser Arg Ala Pro Ser Pro Leu
            195                 200                 205

Tyr Ser Val Glu Phe Ser Glu Glu Pro Phe Gly Val Ile Val His Arg
        210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
        290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
            355                 360                 365

Leu Gly Phe His Leu Cys Arg Trp Gly Tyr Ser Ser Thr Ala Ile Thr
        370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Pro Tyr Asp Glu Gly Leu Arg Arg
        450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
            500                 505                 510
```

63                                                                          64

```
Asp Gly Met Trp Ile Asp Met Asn Glu Pro Ser Asn Phe Ile Arg Gly
        515                 520                 525

Ser Glu Asp Gly Cys Pro Asn Asn Glu Leu Glu Asn Pro Pro Tyr Val
        530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
        610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
        675                 680                 685

Glu Pro Ala Gln Gln Ala Met Arg Lys Ala Leu Thr Leu Arg Tyr Ala
        690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
        755                 760                 765

Leu Gly Thr Trp Tyr Asp Leu Gln Thr Val Pro Ile Glu Ala Leu Gly
        770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Asp Gly Glu Ser
        850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
        915                 920                 925

Ser Pro Asp Thr Lys Val Leu Asp Ile Cys Val Ser Leu Leu Met Gly
```

-continued

```
      930              935              940

Glu Gln Phe Leu Val Ser Trp Cys
945                  950

<210> SEQ ID NO 7
<211> LENGTH: 925
<212> TYPE: PRT
<213> ORGANISM: artificial
<220> FEATURE:
<223> OTHER INFORMATION: hGAAwt w/o sp

<400> SEQUENCE: 7

Gly His Ile Leu Leu His Asp Phe Leu Leu Val Pro Arg Glu Leu Ser
1               5                   10                  15

Gly Ser Ser Pro Val Leu Glu Glu Thr His Pro Ala His Gln Gln Gly
            20                  25                  30

Ala Ser Arg Pro Gly Pro Arg Asp Ala Gln Ala His Pro Gly Arg Pro
        35                  40                  45

Arg Ala Val Pro Thr Gln Cys Asp Val Pro Pro Asn Ser Arg Phe Asp
    50                  55                  60

Cys Ala Pro Asp Lys Ala Ile Thr Gln Glu Gln Cys Glu Ala Arg Gly
65                  70                  75                  80

Cys Cys Tyr Ile Pro Ala Lys Gln Gly Leu Gln Gly Ala Gln Met Gly
                85                  90                  95

Gln Pro Trp Cys Phe Phe Pro Pro Ser Tyr Pro Ser Tyr Lys Leu Glu
            100                 105                 110

Asn Leu Ser Ser Ser Glu Met Gly Tyr Thr Ala Thr Leu Thr Arg Thr
            115                 120                 125

Thr Pro Thr Phe Phe Pro Lys Asp Ile Leu Thr Leu Arg Leu Asp Val
    130                 135                 140

Met Met Glu Thr Glu Asn Arg Leu His Phe Thr Ile Lys Asp Pro Ala
145                 150                 155                 160

Asn Arg Arg Tyr Glu Val Pro Leu Glu Thr Pro His Val His Ser Arg
                165                 170                 175

Ala Pro Ser Pro Leu Tyr Ser Val Glu Phe Ser Glu Glu Pro Phe Gly
            180                 185                 190

Val Ile Val Arg Arg Gln Leu Asp Gly Arg Val Leu Leu Asn Thr Thr
            195                 200                 205

Val Ala Pro Leu Phe Phe Ala Asp Gln Phe Leu Gln Leu Ser Thr Ser
    210                 215                 220

Leu Pro Ser Gln Tyr Ile Thr Gly Leu Ala Glu His Leu Ser Pro Leu
225                 230                 235                 240

Met Leu Ser Thr Ser Trp Thr Arg Ile Thr Leu Trp Asn Arg Asp Leu
                245                 250                 255

Ala Pro Thr Pro Gly Ala Asn Leu Tyr Gly Ser His Pro Phe Tyr Leu
            260                 265                 270

Ala Leu Glu Asp Gly Gly Ser Ala His Gly Val Phe Leu Leu Asn Ser
            275                 280                 285

Asn Ala Met Asp Val Val Leu Gln Pro Ser Pro Ala Leu Ser Trp Arg
    290                 295                 300

Ser Thr Gly Gly Ile Leu Asp Val Tyr Ile Phe Leu Gly Pro Glu Pro
305                 310                 315                 320

Lys Ser Val Val Gln Gln Tyr Leu Asp Val Val Gly Tyr Pro Phe Met
                325                 330                 335

Pro Pro Tyr Trp Gly Leu Gly Phe His Leu Cys Arg Trp Gly Tyr Ser
```

-continued

```
              340             345                 350

Ser Thr Ala Ile Thr Arg Gln Val Val Glu Asn Met Thr Arg Ala His
        355             360                 365

Phe Pro Leu Asp Val Gln Trp Asn Asp Leu Asp Tyr Met Asp Ser Arg
        370             375             380

Arg Asp Phe Thr Phe Asn Lys Asp Gly Phe Arg Asp Phe Pro Ala Met
385             390             395                 400

Val Gln Glu Leu His Gln Gly Gly Arg Arg Tyr Met Met Ile Val Asp
                405             410                 415

Pro Ala Ile Ser Ser Ser Gly Pro Ala Gly Ser Tyr Arg Pro Tyr Asp
                420             425             430

Glu Gly Leu Arg Arg Gly Val Phe Ile Thr Asn Glu Thr Gly Gln Pro
            435             440             445

Leu Ile Gly Lys Val Trp Pro Gly Ser Thr Ala Phe Pro Asp Phe Thr
        450             455             460

Asn Pro Thr Ala Leu Ala Trp Trp Glu Asp Met Val Ala Glu Phe His
465             470             475                 480

Asp Gln Val Pro Phe Asp Gly Met Trp Ile Asp Met Asn Glu Pro Ser
                485             490                 495

Asn Phe Ile Arg Gly Ser Glu Asp Gly Cys Pro Asn Asn Glu Leu Glu
                500             505             510

Asn Pro Pro Tyr Val Pro Gly Val Val Gly Gly Thr Leu Gln Ala Ala
                515             520             525

Thr Ile Cys Ala Ser Ser His Gln Phe Leu Ser Thr His Tyr Asn Leu
            530             535             540

His Asn Leu Tyr Gly Leu Thr Glu Ala Ile Ala Ser His Arg Ala Leu
545             550             555                 560

Val Lys Ala Arg Gly Thr Arg Pro Phe Val Ile Ser Arg Ser Thr Phe
                565             570             575

Ala Gly His Gly Arg Tyr Ala Gly His Trp Thr Gly Asp Val Trp Ser
            580             585             590

Ser Trp Glu Gln Leu Ala Ser Ser Val Pro Glu Ile Leu Gln Phe Asn
        595             600             605

Leu Leu Gly Val Pro Leu Val Gly Ala Asp Val Cys Gly Phe Leu Gly
    610             615             620

Asn Thr Ser Glu Glu Leu Cys Val Arg Trp Thr Gln Leu Gly Ala Phe
625             630             635                 640

Tyr Pro Phe Met Arg Asn His Asn Ser Leu Leu Ser Leu Pro Gln Glu
            645             650             655

Pro Tyr Ser Phe Ser Glu Pro Ala Gln Gln Ala Met Arg Lys Ala Leu
            660             665             670

Thr Leu Arg Tyr Ala Leu Leu Pro His Leu Tyr Thr Leu Phe His Gln
            675             680             685

Ala His Val Ala Gly Glu Thr Val Ala Arg Pro Leu Phe Leu Glu Phe
        690             695             700

Pro Lys Asp Ser Ser Thr Trp Thr Val Asp His Gln Leu Leu Trp Gly
705             710             715                 720

Glu Ala Leu Leu Ile Thr Pro Val Leu Gln Ala Gly Lys Ala Glu Val
                725             730             735

Thr Gly Tyr Phe Pro Leu Gly Thr Trp Tyr Asp Leu Gln Thr Val Pro
            740             745             750

Val Glu Ala Leu Gly Ser Leu Pro Pro Pro Pro Ala Ala Pro Arg Glu
            755             760             765
```

-continued

```
Pro Ala Ile His Ser Glu Gly Gln Trp Val Thr Leu Pro Ala Pro Leu
    770             775             780

Asp Thr Ile Asn Val His Leu Arg Ala Gly Tyr Ile Ile Pro Leu Gln
785             790             795             800

Gly Pro Gly Leu Thr Thr Thr Glu Ser Arg Gln Gln Pro Met Ala Leu
            805             810             815

Ala Val Ala Leu Thr Lys Gly Gly Glu Ala Arg Gly Glu Leu Phe Trp
            820             825             830

Asp Asp Gly Glu Ser Leu Glu Val Leu Glu Arg Gly Ala Tyr Thr Gln
            835             840             845

Val Ile Phe Leu Ala Arg Asn Asn Thr Ile Val Asn Glu Leu Val Arg
    850             855             860

Val Thr Ser Glu Gly Ala Gly Leu Gln Leu Gln Lys Val Thr Val Leu
865             870             875             880

Gly Val Ala Thr Ala Pro Gln Gln Val Leu Ser Asn Gly Val Pro Val
            885             890             895

Ser Asn Phe Thr Tyr Ser Pro Asp Thr Lys Val Leu Asp Ile Cys Val
            900             905             910

Ser Leu Leu Met Gly Glu Gln Phe Leu Val Ser Trp Cys
    915             920             925

<210> SEQ ID NO 8
<211> LENGTH: 925
<212> TYPE: PRT
<213> ORGANISM: artificial
<220> FEATURE:
<223> OTHER INFORMATION: variant hGAAwt w/o sp

<400> SEQUENCE: 8

Gly His Ile Leu Leu His Asp Phe Leu Leu Val Pro Arg Glu Leu Ser
1               5               10              15

Gly Ser Ser Pro Val Leu Glu Glu Thr His Pro Ala His Gln Gln Gly
            20              25              30

Ala Ser Arg Pro Gly Pro Arg Asp Ala Gln Ala His Pro Gly Arg Pro
            35              40              45

Arg Ala Val Pro Thr Gln Cys Asp Val Pro Pro Asn Ser Arg Phe Asp
    50              55              60

Cys Ala Pro Asp Lys Ala Ile Thr Gln Glu Gln Cys Glu Ala Arg Gly
65              70              75              80

Cys Cys Tyr Ile Pro Ala Lys Gln Gly Leu Gln Gly Ala Gln Met Gly
            85              90              95

Gln Pro Trp Cys Phe Phe Pro Pro Ser Tyr Pro Ser Tyr Lys Leu Glu
            100             105             110

Asn Leu Ser Ser Ser Glu Met Gly Tyr Thr Ala Thr Leu Thr Arg Thr
            115             120             125

Thr Pro Thr Phe Phe Pro Lys Asp Ile Leu Thr Leu Arg Leu Asp Val
    130             135             140

Met Met Glu Thr Glu Asn Arg Leu His Phe Thr Ile Lys Asp Pro Ala
145             150             155             160

Asn Arg Arg Tyr Glu Val Pro Leu Glu Thr Pro Arg Val His Ser Arg
            165             170             175

Ala Pro Ser Pro Leu Tyr Ser Val Glu Phe Ser Glu Glu Pro Phe Gly
            180             185             190

Val Ile Val His Arg Gln Leu Asp Gly Arg Val Leu Leu Asn Thr Thr
    195             200             205
```

```
Val Ala Pro Leu Phe Phe Ala Asp Gln Phe Leu Gln Leu Ser Thr Ser
    210             215                 220
```

```
Leu Pro Ser Gln Tyr Ile Thr Gly Leu Ala Glu His Leu Ser Pro Leu
225                 230                 235                 240
```

```
Met Leu Ser Thr Ser Trp Thr Arg Ile Thr Leu Trp Asn Arg Asp Leu
            245                 250                 255
```

```
Ala Pro Thr Pro Gly Ala Asn Leu Tyr Gly Ser His Pro Phe Tyr Leu
            260                 265                 270
```

```
Ala Leu Glu Asp Gly Gly Ser Ala His Gly Val Phe Leu Leu Asn Ser
            275                 280                 285
```

```
Asn Ala Met Asp Val Val Leu Gln Pro Ser Pro Ala Leu Ser Trp Arg
    290                 295                 300
```

```
Ser Thr Gly Gly Ile Leu Asp Val Tyr Ile Phe Leu Gly Pro Glu Pro
305                 310                 315                 320
```

```
Lys Ser Val Val Gln Gln Tyr Leu Asp Val Val Gly Tyr Pro Phe Met
                325                 330                 335
```

```
Pro Pro Tyr Trp Gly Leu Gly Phe His Leu Cys Arg Trp Gly Tyr Ser
            340                 345                 350
```

```
Ser Thr Ala Ile Thr Arg Gln Val Val Glu Asn Met Thr Arg Ala His
            355                 360                 365
```

```
Phe Pro Leu Asp Val Gln Trp Asn Asp Leu Asp Tyr Met Asp Ser Arg
    370                 375                 380
```

```
Arg Asp Phe Thr Phe Asn Lys Asp Gly Phe Arg Asp Phe Pro Ala Met
385                 390                 395                 400
```

```
Val Gln Glu Leu His Gln Gly Gly Arg Arg Tyr Met Met Ile Val Asp
                405                 410                 415
```

```
Pro Ala Ile Ser Ser Ser Gly Pro Ala Gly Ser Tyr Arg Pro Tyr Asp
            420                 425                 430
```

```
Glu Gly Leu Arg Arg Gly Val Phe Ile Thr Asn Glu Thr Gly Gln Pro
            435                 440                 445
```

```
Leu Ile Gly Lys Val Trp Pro Gly Ser Thr Ala Phe Pro Asp Phe Thr
    450                 455                 460
```

```
Asn Pro Thr Ala Leu Ala Trp Trp Glu Asp Met Val Ala Glu Phe His
465                 470                 475                 480
```

```
Asp Gln Val Pro Phe Asp Gly Met Trp Ile Asp Met Asn Glu Pro Ser
                485                 490                 495
```

```
Asn Phe Ile Arg Gly Ser Glu Asp Gly Cys Pro Asn Asn Glu Leu Glu
            500                 505                 510
```

```
Asn Pro Pro Tyr Val Pro Gly Val Val Gly Gly Thr Leu Gln Ala Ala
            515                 520                 525
```

```
Thr Ile Cys Ala Ser Ser His Gln Phe Leu Ser Thr His Tyr Asn Leu
    530                 535                 540
```

```
His Asn Leu Tyr Gly Leu Thr Glu Ala Ile Ala Ser His Arg Ala Leu
545                 550                 555                 560
```

```
Val Lys Ala Arg Gly Thr Arg Pro Phe Val Ile Ser Arg Ser Thr Phe
                565                 570                 575
```

```
Ala Gly His Gly Arg Tyr Ala Gly His Trp Thr Gly Asp Val Trp Ser
            580                 585                 590
```

```
Ser Trp Glu Gln Leu Ala Ser Ser Val Pro Glu Ile Leu Gln Phe Asn
            595                 600                 605
```

```
Leu Leu Gly Val Pro Leu Val Gly Ala Asp Val Cys Gly Phe Leu Gly
    610                 615                 620
```

```
Asn Thr Ser Glu Glu Leu Cys Val Arg Trp Thr Gln Leu Gly Ala Phe
625             630                 635                 640

Tyr Pro Phe Met Arg Asn His Asn Ser Leu Leu Ser Leu Pro Gln Glu
                645             650                 655

Pro Tyr Ser Phe Ser Glu Pro Ala Gln Gln Ala Met Arg Lys Ala Leu
                660             665                 670

Thr Leu Arg Tyr Ala Leu Leu Pro His Leu Tyr Thr Leu Phe His Gln
            675             680                 685

Ala His Val Ala Gly Glu Thr Val Ala Arg Pro Leu Phe Leu Glu Phe
        690                 695                 700

Pro Lys Asp Ser Ser Thr Trp Thr Val Asp His Gln Leu Leu Trp Gly
705             710                 715                 720

Glu Ala Leu Leu Ile Thr Pro Val Leu Gln Ala Gly Lys Ala Glu Val
                725             730                 735

Thr Gly Tyr Phe Pro Leu Gly Thr Trp Tyr Asp Leu Gln Thr Val Pro
                740             745                 750

Ile Glu Ala Leu Gly Ser Leu Pro Pro Pro Pro Ala Ala Pro Arg Glu
            755             760                 765

Pro Ala Ile His Ser Glu Gly Gln Trp Val Thr Leu Pro Ala Pro Leu
        770             775                 780

Asp Thr Ile Asn Val His Leu Arg Ala Gly Tyr Ile Ile Pro Leu Gln
785             790                 795                 800

Gly Pro Gly Leu Thr Thr Thr Glu Ser Arg Gln Gln Pro Met Ala Leu
                805                 810                 815

Ala Val Ala Leu Thr Lys Gly Gly Glu Ala Arg Gly Glu Leu Phe Trp
                820                 825                 830

Asp Asp Gly Glu Ser Leu Glu Val Leu Glu Arg Gly Ala Tyr Thr Gln
            835                 840                 845

Val Ile Phe Leu Ala Arg Asn Asn Thr Ile Val Asn Glu Leu Val Arg
        850                 855                 860

Val Thr Ser Glu Gly Ala Gly Leu Gln Leu Gln Lys Val Thr Val Leu
865                 870                 875                 880

Gly Val Ala Thr Ala Pro Gln Gln Val Leu Ser Asn Gly Val Pro Val
                885                 890                 895

Ser Asn Phe Thr Tyr Ser Pro Asp Thr Lys Val Leu Asp Ile Cys Val
                900                 905                 910

Ser Leu Leu Met Gly Glu Gln Phe Leu Val Ser Trp Cys
            915                 920                 925
```

```
<210> SEQ ID NO 9
<211> LENGTH: 883
<212> TYPE: PRT
<213> ORGANISM: artificial
<220> FEATURE:
<223> OTHER INFORMATION: amino acid sequence of delta42 GAA

<400> SEQUENCE: 9
```

```
Ala His Pro Gly Arg Pro Arg Ala Val Pro Thr Gln Cys Asp Val Pro
1               5                   10                  15

Pro Asn Ser Arg Phe Asp Cys Ala Pro Asp Lys Ala Ile Thr Gln Glu
                20                  25                  30

Gln Cys Glu Ala Arg Gly Cys Cys Tyr Ile Pro Ala Lys Gln Gly Leu
            35                  40                  45

Gln Gly Ala Gln Met Gly Gln Pro Trp Cys Phe Phe Pro Pro Ser Tyr
        50                  55                  60
```

-continued

```
Pro Ser Tyr Lys Leu Glu Asn Leu Ser Ser Ser Glu Met Gly Tyr Thr
65              70              75              80

Ala Thr Leu Thr Arg Thr Thr Pro Thr Phe Phe Pro Lys Asp Ile Leu
            85              90              95

Thr Leu Arg Leu Asp Val Met Met Glu Thr Glu Asn Arg Leu His Phe
        100             105             110

Thr Ile Lys Asp Pro Ala Asn Arg Arg Tyr Glu Val Pro Leu Glu Thr
        115             120             125

Pro His Val His Ser Arg Ala Pro Ser Pro Leu Tyr Ser Val Glu Phe
    130             135             140

Ser Glu Glu Pro Phe Gly Val Ile Val Arg Arg Gln Leu Asp Gly Arg
145             150             155             160

Val Leu Leu Asn Thr Thr Val Ala Pro Leu Phe Phe Ala Asp Gln Phe
                165             170             175

Leu Gln Leu Ser Thr Ser Leu Pro Ser Gln Tyr Ile Thr Gly Leu Ala
            180             185             190

Glu His Leu Ser Pro Leu Met Leu Ser Thr Ser Trp Thr Arg Ile Thr
        195             200             205

Leu Trp Asn Arg Asp Leu Ala Pro Thr Pro Gly Ala Asn Leu Tyr Gly
    210             215             220

Ser His Pro Phe Tyr Leu Ala Leu Glu Asp Gly Gly Ser Ala His Gly
225             230             235             240

Val Phe Leu Leu Asn Ser Asn Ala Met Asp Val Val Leu Gln Pro Ser
                245             250             255

Pro Ala Leu Ser Trp Arg Ser Thr Gly Gly Ile Leu Asp Val Tyr Ile
            260             265             270

Phe Leu Gly Pro Glu Pro Lys Ser Val Val Gln Gln Tyr Leu Asp Val
        275             280             285

Val Gly Tyr Pro Phe Met Pro Pro Tyr Trp Gly Leu Gly Phe His Leu
    290             295             300

Cys Arg Trp Gly Tyr Ser Ser Thr Ala Ile Thr Arg Gln Val Val Glu
305             310             315             320

Asn Met Thr Arg Ala His Phe Pro Leu Asp Val Gln Trp Asn Asp Leu
            325             330             335

Asp Tyr Met Asp Ser Arg Arg Asp Phe Thr Phe Asn Lys Asp Gly Phe
            340             345             350

Arg Asp Phe Pro Ala Met Val Gln Glu Leu His Gln Gly Gly Arg Arg
        355             360             365

Tyr Met Met Ile Val Asp Pro Ala Ile Ser Ser Ser Gly Pro Ala Gly
    370             375             380

Ser Tyr Arg Pro Tyr Asp Glu Gly Leu Arg Arg Gly Val Phe Ile Thr
385             390             395             400

Asn Glu Thr Gly Gln Pro Leu Ile Gly Lys Val Trp Pro Gly Ser Thr
            405             410             415

Ala Phe Pro Asp Phe Thr Asn Pro Thr Ala Leu Ala Trp Trp Glu Asp
            420             425             430

Met Val Ala Glu Phe His Asp Gln Val Pro Phe Asp Gly Met Trp Ile
        435             440             445

Asp Met Asn Glu Pro Ser Asn Phe Ile Arg Gly Ser Glu Asp Gly Cys
        450             455             460

Pro Asn Asn Glu Leu Glu Asn Pro Pro Tyr Val Pro Gly Val Val Gly
465             470             475             480

Gly Thr Leu Gln Ala Ala Thr Ile Cys Ala Ser Ser His Gln Phe Leu
```

```
                      485                 490                 495
Ser Thr His Tyr Asn Leu His Asn Leu Tyr Gly Leu Thr Glu Ala Ile
            500                 505                 510

Ala Ser His Arg Ala Leu Val Lys Ala Arg Gly Thr Arg Pro Phe Val
            515                 520                 525

Ile Ser Arg Ser Thr Phe Ala Gly His Gly Arg Tyr Ala Gly His Trp
            530                 535                 540

Thr Gly Asp Val Trp Ser Ser Trp Glu Gln Leu Ala Ser Ser Val Pro
545                 550                 555                 560

Glu Ile Leu Gln Phe Asn Leu Leu Gly Val Pro Leu Val Gly Ala Asp
                565                 570                 575

Val Cys Gly Phe Leu Gly Asn Thr Ser Glu Glu Leu Cys Val Arg Trp
                580                 585                 590

Thr Gln Leu Gly Ala Phe Tyr Pro Phe Met Arg Asn His Asn Ser Leu
            595                 600                 605

Leu Ser Leu Pro Gln Glu Pro Tyr Ser Phe Ser Glu Pro Ala Gln Gln
            610                 615                 620

Ala Met Arg Lys Ala Leu Thr Leu Arg Tyr Ala Leu Leu Pro His Leu
625                 630                 635                 640

Tyr Thr Leu Phe His Gln Ala His Val Ala Gly Glu Thr Val Ala Arg
                645                 650                 655

Pro Leu Phe Leu Glu Phe Pro Lys Asp Ser Ser Thr Trp Thr Val Asp
                660                 665                 670

His Gln Leu Leu Trp Gly Glu Ala Leu Leu Ile Thr Pro Val Leu Gln
            675                 680                 685

Ala Gly Lys Ala Glu Val Thr Gly Tyr Phe Pro Leu Gly Thr Trp Tyr
            690                 695                 700

Asp Leu Gln Thr Val Pro Val Glu Ala Leu Gly Ser Leu Pro Pro Pro
705                 710                 715                 720

Pro Ala Ala Pro Arg Glu Pro Ala Ile His Ser Glu Gly Gln Trp Val
                725                 730                 735

Thr Leu Pro Ala Pro Leu Asp Thr Ile Asn Val His Leu Arg Ala Gly
            740                 745                 750

Tyr Ile Ile Pro Leu Gln Gly Pro Gly Leu Thr Thr Thr Glu Ser Arg
            755                 760                 765

Gln Gln Pro Met Ala Leu Ala Val Ala Leu Thr Lys Gly Gly Glu Ala
            770                 775                 780

Arg Gly Glu Leu Phe Trp Asp Asp Gly Glu Ser Leu Glu Val Leu Glu
785                 790                 795                 800

Arg Gly Ala Tyr Thr Gln Val Ile Phe Leu Ala Arg Asn Asn Thr Ile
                805                 810                 815

Val Asn Glu Leu Val Arg Val Thr Ser Glu Gly Ala Gly Leu Gln Leu
                820                 825                 830

Gln Lys Val Thr Val Leu Gly Val Ala Thr Ala Pro Gln Gln Val Leu
            835                 840                 845

Ser Asn Gly Val Pro Val Ser Asn Phe Thr Tyr Ser Pro Asp Thr Lys
            850                 855                 860

Val Leu Asp Ile Cys Val Ser Leu Leu Met Gly Glu Gln Phe Leu Val
865                 870                 875                 880

Ser Trp Cys

<210> SEQ ID NO 10
<211> LENGTH: 2652
```

```
<212> TYPE: DNA
<213> ORGANISM: artificial
<220> FEATURE:
<223> OTHER INFORMATION: hGAAco1-delta-42

<400> SEQUENCE: 10
gcccaccccg gcagacctag agctgtgcct acccagtgtg acgtgccccc caacagcaga      60
ttcgactgcg cccctgacaa ggccatcacc caggaacagt gcgaggccag aggctgctgc     120
tacatccctg ccaagcaggg actgcagggc gctcagatgg gacagccctg gtgcttcttc     180
ccaccctcct accccagcta caagctggaa aacctgagca gcagcgagat gggctacacc     240
gccaccctga ccagaaccac ccccacattc ttcccaaagg acatcctgac cctgcggctg     300
gacgtgatga tggaaaccga gaaccggctg cacttcacca tcaaggaccc cgccaatcgg     360
agatacgagg tgcccctgga aacccccac gtgcactcta gagcccccag ccctctgtac     420
agcgtggaat tcagcgagga acccttcggc gtgatcgtgc ggagacagct ggatggcaga     480
gtgctgctga acaccaccgt ggcccctctg ttcttcgccg accagttcct gcagctgagc     540
accagcctgc ccagccagta catcacagga ctggccgagc acctgagccc cctgatgctg     600
agcacatcct ggaccggat cacccctgtgg aacagggatc tggcccctac ccctggcgcc     660
aatctgtacg gcagccaccc tttctacctg gccctggaag atggcggatc tgcccacgga     720
gtgtttctgc tgaactccaa cgccatggac gtggtgctgc agcctagccc tgccctgtct     780
tggagaagca caggcggcat cctggatgtg tacatctttc tgggccccga gcccaagagc     840
gtggtgcagc agtatctgga tgtcgtgggc taccccttca tgccccctta ctggggcctg     900
ggattccacc tgtgcagatg gggctactcc agcaccgcca tcaccagaca ggtggtggaa     960
aacatgacca gagcccactt cccactggat gtgcagtgga acgacctgga ctacatggac    1020
agcagacggg acttcaccct caacaaggac ggcttccggg acttcccgc catggtgcag    1080 gaactgcatc agggcggcag acggtacatg atgatcgtgg atcccgccat cagctcctct    1140
ggccctgccg gctcttacag accctacgac gagggcctgc ggagaggcgt gttcatcacc    1200
aacgagacag gccagcccct gatcggcaaa gtgtggcctg gcagcacagc cttccccgac    1260
ttcaccaatc ctaccgccct ggcttggtgg gaggacatgg tggccgagtt ccacgaccag    1320
gtgcccttcg acggcatgtg gatcgacatg aacgagccca gcaacttcat ccggggcagc    1380
gaggatggct gccccaacaa cgaactggaa aatcccccctt acgtgcccgg cgtcgtgggc    1440
ggaacactgc aggccgctac aatctgtgcc agcagccacc agtttctgag cacccactac    1500
aacctgcaca acctgtacgg cctgaccgag gccattgcca gcaccgcgc tctcgtgaaa    1560 gccagaggca cacggcccctt cgtgatcagc agaagcacct tgccggcca cggcagatac    1620 gccggacatt ggactggcga cgtgtggtcc tcttgggagc agctggcctc tagcgtgccc    1680
gagatcctgc agttcaatct gctgggcgtg ccactcgtgg cgccgatgt gtgtggcttc    1740 ctgggcaaca cctccgagga actgtgtgtg cggtggacac agctgggcgc cttctacccct    1800 ttcatgagaa accacaacag cctgctgagc ctgcccagg aaccctacag ctttagcgag    1860
cctgcacagc aggccatgcg gaaggccctg acactgagat acgctctgct gccccacctg    1920
tacaccctgt ttaccaggc ccatgtgcc ggcgagacag tggccagacc tctgtttctg    1980
gaattcccca aggacagcag cacctggacc gtggaccatc agctgctgtg gggagaggct    2040
ctgctgatta ccccagtgct gcaggcaggc aaggccgaag tgaccggcta ctttcccctg    2100
ggcacttggt acgacctgca gaccgtgcct gtggaagccc tgggatctct gcctccacct    2160
```

```
cctgccgctc ctagagagcc tgccattcac tctgagggcc agtgggtcac actgcctgcc      2220
cccctggata ccatcaacgt gcacctgagg gccggctaca tcataccact gcagggacct      2280
ggcctgacca ccaccgagtc tagacagcag ccaatggccc tggccgtggc cctgaccaaa      2340
ggcggagaag ctaggggcga gctgttctgg gacgatggcg agagcctgga agtgctggaa      2400
agaggcgcct atacccaagt gatcttcctg gcccggaaca acaccatcgt gaacgagctg      2460
gtgcgcgtga cctctgaagg cgctggactg cagctgcaga aagtgaccgt gctgggagtg      2520
gccacagccc ctcagcaggt gctgtctaat ggcgtgcccg tgtccaactt cacctacagc      2580
cccgacacca aggtgctgga catctgcgtg tcactgctga tgggagagca gtttctggtg      2640
tcctggtgct ga                                                           2652
```

```
<210> SEQ ID NO 11
<211> LENGTH: 2652
<212> TYPE: DNA
<213> ORGANISM: artificial
<220> FEATURE:
<223> OTHER INFORMATION: hGAAco2-delta-42

<400> SEQUENCE: 11
```

```
gcccatcctg gtagaccaag agctgtgcct acccaatgcg acgtgccacc caactcccga       60
ttcgactgcg cgccagataa ggctattacc caagagcagt gtgaagccag aggttgctgc      120
tacatcccag cgaagcaagg attgcaaggc ccccaaatgg acaaccttg gtgtttcttc       180 ccccccttcgt acccatcata taaactcgaa aacctgtcct cttcggaaat gggttatact      240
gccaccctca ccagaactac tcctactttc ttcccgaaag acatcttgac cttgaggctg      300
gacgtgatga tggagactga aaaccggctg catttcacta tcaaagatcc tgccaatcgg      360
cgatacgagg tccctctgga aacccctcac gtgcactcac gggctccttc tccgctttac      420
tccgtcgaat ctctgagga acccttcgga gtgatcgtta gacgccagct ggatggtaga       480
gtgctgttga acactactgt ggccccactt ttcttcgctg accagtttct gcaactgtcc      540
acttccctgc catcccagta cattactgga ctcgccgaac acctgtcgcc actgatgctc      600
tcgacctctt ggactagaat cactttgtgg aacagagact ggcccctac tccgggagca       660 aatctgtacg gaagccaccc ttttttacctg gcgctcgaag atggcggatc cgctcacgga      720
gtgttcctgc tgaatagcaa cgcaatggac gtggtgctgc aaccttcccc tgcactcagt      780
tggagaagta ccggggggtat tctggacgtg tacatcttcc tcggaccaga acccaagagc      840
gtggtgcagc aatatctgga cgtggtcgga taccctttta tgcctcctta ctggggactg      900
ggattccacc tttgccgttg gggctactca tccaccgcca ttaccagaca ggtggtggag      960
aatatgacca gagcccactt ccctctcgac gtgcagtgga cgatctggga ctatatggac     1020
tcccggagag atttcacctt caacaaggac gggttccgcg attttcccgc gatggttcaa     1080
gagctccacc agggtggtcg aagatatatg atgatcgtcg acccagccat ttcgagcagc     1140
ggacccgctg gatcttatag accttacgac gaaggcctta ggagaggagt gttcatcaca     1200
aacgagactg gacagccttt gatcggtaaa gtgtggcctg gatcaaccgc ctttcctgac     1260
tttaccaatc ccactgcctt ggcttggtgg gaggacatgg tggccgaatt ccacgaccaa     1320
gtcccctttg atggaatgtg gatcgatatg aacgaaccaa gcaattttat cagaggttcc     1380
gaagacggtt gccccaacaa cgaactggaa aaccctcctt atgtgcccgg agtcgtgggc     1440
ggaacattac aggccgcgac tatttgcgcc agcagccacc aattcctgtc cactcactac     1500
aacctccaca accttttatgg attaaccgaa gctattgcaa gtcacagggc tctggtgaag     1560
```

-continued

```
gctagaggga ctaggccctt tgtgatctcc cgatccacct ttgccggaca cgggagatac     1620
gccggtcact ggactggtga cgtgtggagc tcatgggaac aactggcctc ctccgtgccg     1680
gaaatcttac agttcaacct tctgggtgtc cctcttgtcg agcagacgt gtgtgggttt      1740 cttggtaaca cctccgagga actgtgtgtg cgctggactc aactgggtgc attctaccca     1800
ttcatgagaa accacaactc cttgctgtcc ctgccacaag agccctactc gttcagcgag     1860
cctgcacaac aggctatgcg gaaggcactg accctgagat acgccctgct tccacactta     1920
tacactctct tccatcaagc gcatgtggca ggagaaaccg ttgcaaggcc tcttttcctt     1980
gaattcccca aggattcctc gacttggacg gtggatcatc agctgctgtg gggagaagct     2040
ctgctgatta ctccagtgtt gcaagccgga aaagctgagg tgaccggata ctttccgctg     2100
ggaacctggt acgacctcca gactgtccct gttgaagccc ttggatcact gcctccgcct     2160
ccggcagctc cacgcgaacc agctatacat tccgagggac agtgggttac attaccagct     2220
cctctggaca caatcaacgt ccacttaaga gctggctaca ttatccctct gcaaggacca     2280
ggactgacta cgaccgagag cagacagcag ccaatggcac tggctgtggc tctgaccaag     2340
ggaggggaag ctagaggaga actcttctgg gatgatgggg agtcccttga agtgctggaa     2400
agaggcgctt acactcaagt cattttcctt gcacggaaca acaccattgt gaacgaattg     2460
gtgcgagtga ccagcgaagg agctggactt caactgcaga aggtcactgt gctcggagtg     2520
gctaccgctc ctcagcaagt gctgtcgaat ggagtccccg tgtcaaactt tacctactcc     2580
cctgacacta aggtgctcga catttgcgtg tccctcctga tgggagagca gttccttgtg     2640
tcctggtgtt ga                                                          2652
```

```
<210> SEQ ID NO 12
<211> LENGTH: 28
<212> TYPE: PRT
<213> ORGANISM: artificial
<220> FEATURE:
<223> OTHER INFORMATION: amino acid sequence of the CTP

<400> SEQUENCE: 12

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25
```

```
<210> SEQ ID NO 13
<211> LENGTH: 84
<212> TYPE: DNA
<213> ORGANISM: artificial
<220> FEATURE:
<223> OTHER INFORMATION: nucleic acid sequence encoding the CTP (HD4)

<400> SEQUENCE: 13
agcagcagct ctaaagcccc tccacctagc ctgccttctc caagcagact gcctggacct     60
agcgacaccc ctattctgcc tcaa                                             84
```

```
<210> SEQ ID NO 14
<211> LENGTH: 51
<212> TYPE: DNA
<213> ORGANISM: artificial
<220> FEATURE:
<223> OTHER INFORMATION: SPADIN (HD6)

<400> SEQUENCE: 14
```

-continued

```
gctccacttc ctcgttggag tggccctatc ggagtgtctt ggggactgag a          51

<210> SEQ ID NO 15
<211> LENGTH: 39
<212> TYPE: DNA
<213> ORGANISM: artificial
<220> FEATURE:
<223> OTHER INFORMATION: Neurotensin (HD7)

<400> SEQUENCE: 15
cagctgtacg agaacaagcc cagacggccc tacatcctg                         39

<210> SEQ ID NO 16
<211> LENGTH: 15
<212> TYPE: DNA
<213> ORGANISM: artificial
<220> FEATURE:
<223> OTHER INFORMATION: Neurotensin fragment (HD8)

<400> SEQUENCE: 16
cggccctaca tcctg                                                   15

<210> SEQ ID NO 17
<211> LENGTH: 9
<212> TYPE: DNA
<213> ORGANISM: artificial
<220> FEATURE:
<223> OTHER INFORMATION: linker

<400> SEQUENCE: 17 ggcgcgccg                                                          9

<210> SEQ ID NO 18
<211> LENGTH: 27
<212> TYPE: PRT
<213> ORGANISM: artificial
<220> FEATURE:
<223> OTHER INFORMATION: sp1

<400> SEQUENCE: 18

Met Gly Val Arg His Pro Pro Cys Ser His Arg Leu Leu Ala Val Cys
1               5                   10                  15

Ala Leu Val Ser Leu Ala Thr Ala Ala Leu Leu
            20                  25

<210> SEQ ID NO 19
<211> LENGTH: 24
<212> TYPE: PRT
<213> ORGANISM: artificial
<220> FEATURE:
<223> OTHER INFORMATION: sp2

<400> SEQUENCE: 19

Met Pro Ser Ser Val Ser Trp Gly Ile Leu Leu Leu Ala Gly Leu Cys
1               5                   10                  15

Cys Leu Val Pro Val Ser Leu Ala
            20

<210> SEQ ID NO 20
<211> LENGTH: 25
<212> TYPE: PRT
<213> ORGANISM: artificial
<220> FEATURE:
<223> OTHER INFORMATION: sp6

<400> SEQUENCE: 20
```

Met Pro Pro Pro Arg Thr Gly Arg Gly Leu Leu Trp Leu Gly Leu Val
1               5                   10                  15

Leu Ser Ser Val Cys Val Ala Leu Gly
            20                  25

<210> SEQ ID NO 21
<211> LENGTH: 18
<212> TYPE: PRT
<213> ORGANISM: artificial
<220> FEATURE:
<223> OTHER INFORMATION: sp7

<400> SEQUENCE: 21

Met Ala Phe Leu Trp Leu Leu Ser Cys Trp Ala Leu Leu Gly Thr Thr
1               5                   10                  15

Phe Gly

<210> SEQ ID NO 22
<211> LENGTH: 22
<212> TYPE: PRT
<213> ORGANISM: artificial
<220> FEATURE:
<223> OTHER INFORMATION: sp8

<400> SEQUENCE: 22

Met Ala Ser Arg Leu Thr Leu Leu Thr Leu Leu Leu Leu Leu Leu Ala
1               5                   10                  15

Gly Asp Arg Ala Ser Ser
            20

<210> SEQ ID NO 23
<211> LENGTH: 397
<212> TYPE: DNA
<213> ORGANISM: artificial
<220> FEATURE:
<223> OTHER INFORMATION: hAAT promoter

<400> SEQUENCE: 23
gatcttgcta ccagtggaac agccactaag gattctgcag tgagagcaga gggccagcta      60
agtggtactc tcccagagac tgtctgactc acgccacccc ctccaccttg gacacaggac     120
gctgtggttt ctgagccagg tacaatgact cctttcggta agtgcagtgg aagctgtaca     180
ctgcccaggc aaagcgtccg ggcagcgtag gcgggcgact cagatcccag ccagtggact     240
tagcccctgt ttgctcctcc gataactggg gtgaccttgg ttaatattca ccagcagcct     300
cccccgttgc ccctctggat ccactgctta aatacggacg aggacagggc cctgtctcct     360
cagcttcagg caccaccact gacctgggac agtgaat                             397

<210> SEQ ID NO 24
<211> LENGTH: 321
<212> TYPE: DNA
<213> ORGANISM: artificial
<220> FEATURE:
<223> OTHER INFORMATION: ApoE control region

<400> SEQUENCE: 24
aggctcagag gcacacagga gtttctgggc tcaccctgcc cccttccaac ccctcagttc      60
ccatcctcca gcagctgttt gtgtgctgcc tctgaagtcc acactgaaca aacttcagcc     120
tactcatgtc cctaaaatgg gcaaacattg caagcagcaa acagcaaaca cacagccctc     180
cctgcctgct gaccttggag ctggggcaga ggtcagagac ctctctgggc ccatgccacc     240

-continued

```
tccaacatcc actcgacccc ttggaatttc ggtggagagg agcagaggtt gtcctggcgt      300
ggtttaggta gtgtgagagg g                                                321

<210> SEQ ID NO 25
<211> LENGTH: 441
<212> TYPE: DNA
<213> ORGANISM: artificial
<220> FEATURE:
<223> OTHER INFORMATION: HBB2 intron

<400> SEQUENCE: 25
gtacacatat tgaccaaatc agggtaattt tgcatttgta attttaaaaa atgctttctt       60
cttttaatat acttttttgt ttatcttatt ctaatactt tccctaatct ctttctttca      120
gggcaataat gatacaatgt atcatgcctc tttgcaccat tctaaagaat aacagtgata      180
atttctgggt taaggcaata gcaatatttc tgcatataaa tatttctgca tataaattgt      240
aactgatgta agaggtttca tattgctaat agcagctaca atccagctac cattctgctt      300
ttattttatg gttgggataa ggctggatta ttctgagtcc aagctaggcc cttttgctaa      360
tcatgttcat acctcttatc ttcctcccac agctcctggg caacgtgctg gtctgtgtgc      420
tggcccatca ctttggcaaa g                                               441

<210> SEQ ID NO 26
<211> LENGTH: 441
<212> TYPE: DNA
<213> ORGANISM: artificial
<220> FEATURE:
<223> OTHER INFORMATION: modified HBB2 intron

<400> SEQUENCE: 26
gtacacatat tgaccaaatc agggtaattt tgcatttgta attttaaaaa atgctttctt       60
cttttaatat acttttttgt ttatcttatt ctaatactt tccctaatct ctttctttca      120
gggcaataat gatacaatgt atcatgcctc tttgcaccat tctaaagaat aacagtgata      180
atttctgggt taaggcaata gcaatatttc tgcatataaa tatttctgca tataaattgt      240
aactgatgta agaggtttca tattgctaat agcagctaca atccagctac cattctgctt      300
ttattttctg gttgggataa ggctggatta ttctgagtcc aagctaggcc cttttgctaa      360
tcttgttcat acctcttatc ttcctcccac agctcctggg caacctgctg gtctctctgc      420
tggcccatca ctttggcaaa g                                               441

<210> SEQ ID NO 27
<211> LENGTH: 1438
<212> TYPE: DNA
<213> ORGANISM: artificial
<220> FEATURE:
<223> OTHER INFORMATION: FIX intron

<400> SEQUENCE: 27
ggtttgtttc cttttttaaa atacattgag tatgcttgcc ttttagatat agaaatatct       60
gatgctgtct tcttcactaa attttgatta catgatttga cagcaatatt gaagagtcta      120
acagccagca cgcaggttgg taagtactgg ttctttgtta gctaggtttt cttcttcttc      180
attttttaaa ctaaatagat cgacaatgct tatgatgcat ttatgtttaa taaacactgt      240
tcagttcatg atttggtcat gtaattcctg ttagaaaaca ttcatctcct tggtttaaaa      300
aaattaaaag tgggaaaaca aagaaatagc agaatatagt gaaaaaaaat aaccacatta      360
```

```
tttttgtttg gacttaccac tttgaaatca aaatgggaaa caaaagcaca aacaatggcc      420
ttatttacac aaaaagtctg attttaagat atatgacatt tcaaggtttc agaagtatgt      480
aatgaggtgt gtctctaatt ttttaaatta tatatcttca atttaaagtt ttagttaaaa      540
cataaagatt aacctttcat tagcaagctg ttagttatca ccaacgcttt tcatggatta      600
ggaaaaaatc attttgtctc tatgtcaaac atcttggagt tgatatttgg ggaaacacaa      660
tactcagttg agttccctag gggagaaaag cacgcttaag aattgacata aagagtagga      720
agttagctaa tgcaacatat atcactttgt tttttcacaa ctacagtgac tttatgtatt      780
tcccagagga aggcatacag ggaagaaatt atcccatttg gacaaacagc atgttctcac      840
aggaagcatt tatcacactt acttgtcaac tttctagaat caaatctagt agctgacagt      900
accaggatca ggggtgccaa ccctaagcac ccccagaaag ctgactggcc ctgtggttcc      960
cactccagac atgatgtcag ctgtgaaatc gacgtcgctg gaccataatt aggcttctgt     1020
tcttcaggag acatttgttc aaagtcattt gggcaaccat attctgaaaa cagcccagcc     1080
agggtgatgg atcactttgc aaagatcctc aatgagctat tttcaagtga tgacaaagtg     1140
tgaagttaac cgctcatttg agaactttct ttttcatcca aagtaaattc aaatatgatt     1200
agaaatctga ccttttatta ctggaattct cttgactaaa agtaaaattg aattttaatt     1260
cctaaatctc catgtgtata cagtactgtg ggaacatcac agattttggc tccatgccct     1320
aaagagaaat tggctttcag attatttgga ttaaaaacaa agactttctt aagagatgta     1380
aaattttcat gatgttttct tttttgctaa aactaaagaa ttattctttt acatttca       1438
```

<210> SEQ ID NO 28
<211> LENGTH: 1438
<212> TYPE: DNA
<213> ORGANISM: artificial
<220> FEATURE:
<223> OTHER INFORMATION: modified FIX intron

<400> SEQUENCE: 28

```
ggtttgtttc cttttttaaa atacattgag tatgcttgcc ttttagatat agaaatatct       60
gatgctgtct tcttcactaa attttgatta catgatttga cagcaatatt gaagagtcta      120
acagccagca cgcaggttgg taagtactgg ttctttgtta gctaggtttt cttcttcttc      180 attttttaaaa ctaaatagat cgacattgct tttgttgcat ttatgtttaa taaacactgt      240
tcagttcatg atttggtcat gtaattcctg ttagaaaaca ttcatctcct tggtttaaaa      300
aaattaaaag tgggaaaaca aagaaatagc agaatatagt gaaaaaaaat aaccacatta      360
tttttgtttg gacttaccac tttgaaatca aattgggaaa caaaagcaca aacaatggcc      420
ttatttacac aaaaagtctg attttaagat atatgacatt tcaaggtttc agaagtatgt      480
aatgaggtgt gtctctaatt ttttaaatta tatatcttca atttaaagtt ttagttaaaa      540
cataaagatt aacctttcat tagcaagctg ttagttatca ccaacgcttt tcatggatta      600
ggaaaaaatc attttgtctc tttgtcaaac atcttggagt tgatatttgg ggaaacacaa      660
tactcagttg agttccctag gggagaaaag cacgcttaag aattgacata aagagtagga      720
agttagctat tgcaacatat atcactttgt tttttcacaa ctacagtgac ttttgtatt      780 tcccagagga aggcatacag ggaagaaatt atcccatttg gacaaacagc ttgttctcac      840
aggaagcatt tatcacactt acttgtcaac tttctagaat caaatctagt agctgacagt      900
accaggatca ggggtgccaa ccctaagcac ccccagaaag ctgactggcc ctgtggttcc      960
cactccagac atgatgtcag ctgtgaaatc gacgtcgctg gaccataatt aggcttctgt     1020
```

-continued

```
tcttcaggag acatttgttc aaagtcattt gggcaaccat attctgaaaa cagcccagcc    1080
agggtgttgg atcactttgc aaagatcctc attgagctat tttcaagtgt tgacaaagtg    1140
tgaagttaac cgctcatttg agaactttct ttttcatcca aagtaaattc aaatatgatt    1200
agaaatctga ccttttatta ctggaattct cttgactaaa agtaaaattg aattttaatt    1260
cctaaatctc catgtgtata cagtactgtg ggaacatcac agattttggc tccatgccct    1320
aaagagaaat tggctttcag attatttgga ttaaaaacaa agactttctt aagagatgta    1380
aaattttctt gttgttttct tttttgctaa aactaaagaa ttattctttt acatttca     1438
```

<210> SEQ ID NO 29
<211> LENGTH: 881
<212> TYPE: DNA
<213> ORGANISM: artificial
<220> FEATURE:
<223> OTHER INFORMATION: chicken beta-globin intron

<400> SEQUENCE: 29

```
gcgggagtcg ctgcgttgcc ttcgccccgt gccccgctcc gccgccgcct cgcgccgccc      60
gccccggctc tgactgaccg cgttactccc acaggtgagc gggcgggacg gcccttctcc     120
tccgggctgt aattagcgct tggtttaatg acggcttgtt tcttttctgt ggctgcgtga     180
aagccttgag gggctccggg agggcccttt gtgcgggggg agcggctcgg ggggtgcgtg     240
cgtgtgtgtg tgcgtgggga gcgccgcgtg cggctccgcg ctgcccggcg gctgtgagcg     300
ctgcgggcgc ggcgcggggc tttgtgcgct ccgcagtgtg cgcgagggga gcgcggccgg     360
gggcggtgcc ccgcggtgcg gggggggctg cgaggggaac aaaggctgcg tgcggggtgt     420
gtgcgtgggg gggtgagcag ggggtgtggg cgcgtcggtc gggctgcaac ccccctgca      480 ccccctccc cgagttgctg agcacggccc ggcttcgggt gcggggctcc gtacggggcg      540
tggcgcgggg ctcgccgtgc cgggcggggg gtggcggcag gtgggggtgc cgggcggggc     600
ggggccgcct cgggccgggg agggctcggg ggaggggcgc ggcggccccc ggagcgccgg     660
cggctgtcga ggcgcggcga ccgcagcca ttgccttta tggtaatcgt gcgagagggc     720
gcagggactt cctttgtccc aaatctgtgc ggagccgaaa tctgggaggc gccgccgcac     780
cccctctagc gggcgcgggg cgaagcggtg cggcgccggc aggaaggaaa tgggcgggga     840
gggccttcgt gcgtcgccgc gccgccgtcc ccttctccct c                          881
```

<210> SEQ ID NO 30
<211> LENGTH: 881
<212> TYPE: DNA
<213> ORGANISM: artificial
<220> FEATURE:
<223> OTHER INFORMATION: modified chicken beta-globin intron

<400> SEQUENCE: 30

```
gcgggagtcg ctgcgttgcc ttcgccccgt gccccgctcc gccgccgcct cgcgccgccc      60
gccccggctc tgactgaccg cgttactccc acaggtgagc gggcgggacg gcccttctcc     120
tccgggctgt aattagcgct tggtttaatg acggcttgtt tcttttctgt ggctgcgtga     180
aagccttgag gggctccggg agggcccttt gtgcggggggg agcggctcgg ggggtgcgtg    240
cgtgtgtgtg tgcgtgggga gcgccgcgtg cggctccgcg ctgcccggcg gctgtgagcg     300
ctgcgggcgc ggcgcggggc tttgtgcgct ccgcagtgtg cgcgagggga gcgcggccgg     360
gggcggtgcc ccgcggtgcg gggggggctg cgaggggaac aaaggctgcg tgcggggtgt     420
```

-continued

```
gtgcgtgggg gggtgagcag ggggtgtggg cgcgtcggtc gggctgcaac ccccctgca      480 cccccctccc cgagttgctg agcacggccc ggcttcgggt gcggggctcc gtacggggcg      540
tggcgcgggg ctcgccgtgc cgggcggggg gtggcggcag gtgggggtgc cgggcggggc      600
ggggccgcct cgggccgggg agggctcggg ggaggggcgc ggcggccccc ggagcgccgg      660
cggctgtcga ggcgcggcga gccgcagcca ttgccttttt tggtaatcgt gcgagagggc      720
gcagggactt cctttgtccc aaatctgtgc ggagccgaaa tctgggaggc gccgccgcac      780
cccctctagc gggcgcgggg cgaagcggtg cggcgccggc aggaaggaat tgggcgggga      840
gggccttcgt gcgtcgccgc gccgccgtcc ccttctccct c                        881
```

<210> SEQ ID NO 31
<211> LENGTH: 17
<212> TYPE: PRT
<213> ORGANISM: artificial
<220> FEATURE:
<223> OTHER INFORMATION: Spadin (HD6)

<400> SEQUENCE: 31

```
Ala Pro Leu Pro Arg Trp Ser Gly Pro Ile Gly Val Ser Trp Gly Leu
1               5                   10                  15

Arg
```

<210> SEQ ID NO 32
<211> LENGTH: 13
<212> TYPE: PRT
<213> ORGANISM: artificial
<220> FEATURE:
<223> OTHER INFORMATION: Neurotensin 1-13 (HD7)

<400> SEQUENCE: 32

```
Gln Leu Tyr Glu Asn Lys Pro Arg Arg Pro Tyr Ile Leu
1               5                   10
```

<210> SEQ ID NO 33
<211> LENGTH: 5
<212> TYPE: PRT
<213> ORGANISM: artificial
<220> FEATURE:
<223> OTHER INFORMATION: Neurotensin 9-13 (HD8)

<400> SEQUENCE: 33

```
Arg Pro Tyr Ile Leu
1               5
```

<210> SEQ ID NO 34
<211> LENGTH: 165
<212> TYPE: PRT
<213> ORGANISM: artificial
<220> FEATURE:
<223> OTHER INFORMATION: Beta subunit of the human chorionic
      gonadotropin (hCG)

<400> SEQUENCE: 34

```
Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
        35                  40                  45

Val Asn Thr Thr Ile Cys Ala Gly Tyr Cys Pro Thr Met Thr Arg Val
    50                  55                  60
```

-continued

Leu Gln Gly Val Leu Pro Ala Leu Pro Gln Val Val Cys Asn Tyr Arg
65              70              75              80

Asp Val Arg Phe Glu Ser Ile Arg Leu Pro Gly Cys Pro Arg Gly Val
                85              90              95

Asn Pro Val Val Ser Tyr Ala Val Ala Leu Ser Cys Gln Cys Ala Leu
            100             105             110

Cys Arg Arg Ser Thr Thr Asp Cys Gly Gly Pro Lys Asp His Pro Leu
        115             120             125

Thr Cys Asp Asp Pro Arg Phe Gln Asp Ser Ser Ser Lys Ala Pro
    130             135             140

Pro Pro Ser Leu Pro Ser Pro Ser Arg Leu Pro Gly Pro Ser Asp Thr
145             150             155             160

Pro Ile Leu Pro Gln
                165

<210> SEQ ID NO 35
<211> LENGTH: 921
<212> TYPE: PRT
<213> ORGANISM: artificial
<220> FEATURE:
<223> OTHER INFORMATION: sp7-HDspadin-D42-hGAAco1

<400> SEQUENCE: 35

Met Ala Phe Leu Trp Leu Leu Ser Cys Trp Ala Leu Leu Gly Thr Thr
1               5               10              15

Phe Gly Ala Pro Leu Pro Arg Trp Ser Gly Pro Ile Gly Val Ser Trp
            20              25              30

Gly Leu Arg Gly Ala Pro Ala His Pro Gly Arg Pro Arg Ala Val Pro
        35              40              45

Thr Gln Cys Asp Val Pro Pro Asn Ser Arg Phe Asp Cys Ala Pro Asp
    50              55              60

Lys Ala Ile Thr Gln Glu Gln Cys Glu Ala Arg Gly Cys Cys Tyr Ile
65              70              75              80

Pro Ala Lys Gln Gly Leu Gln Gly Ala Gln Met Gly Gln Pro Trp Cys
            85              90              95

Phe Phe Pro Pro Ser Tyr Pro Ser Tyr Lys Leu Glu Asn Leu Ser Ser
            100             105             110

Ser Glu Met Gly Tyr Thr Ala Thr Leu Thr Arg Thr Thr Pro Thr Phe
        115             120             125

Phe Pro Lys Asp Ile Leu Thr Leu Arg Leu Asp Val Met Met Glu Thr
    130             135             140

Glu Asn Arg Leu His Phe Thr Ile Lys Asp Pro Ala Asn Arg Arg Tyr
145             150             155             160

Glu Val Pro Leu Glu Thr Pro His Val His Ser Arg Ala Pro Ser Pro
            165             170             175

Leu Tyr Ser Val Glu Phe Ser Glu Glu Pro Phe Gly Val Ile Val Arg
            180             185             190

Arg Gln Leu Asp Gly Arg Val Leu Leu Asn Thr Thr Val Ala Pro Leu
        195             200             205

Phe Phe Ala Asp Gln Phe Leu Gln Leu Ser Thr Ser Leu Pro Ser Gln
    210             215             220

Tyr Ile Thr Gly Leu Ala Glu His Leu Ser Pro Leu Met Leu Ser Thr
225             230             235             240

Ser Trp Thr Arg Ile Thr Leu Trp Asn Arg Asp Leu Ala Pro Thr Pro
            245             250             255

-continued

```
Gly Ala Asn Leu Tyr Gly Ser His Pro Phe Tyr Leu Ala Leu Glu Asp
            260                 265                 270

Gly Gly Ser Ala His Gly Val Phe Leu Leu Asn Ser Asn Ala Met Asp
            275                 280                 285

Val Val Leu Gln Pro Ser Pro Ala Leu Ser Trp Arg Ser Thr Gly Gly
290                 295                 300

Ile Leu Asp Val Tyr Ile Phe Leu Gly Pro Glu Pro Lys Ser Val Val
305                 310                 315                 320

Gln Gln Tyr Leu Asp Val Val Gly Tyr Pro Phe Met Pro Pro Tyr Trp
                325                 330                 335

Gly Leu Gly Phe His Leu Cys Arg Trp Gly Tyr Ser Ser Thr Ala Ile
            340                 345                 350

Thr Arg Gln Val Val Glu Asn Met Thr Arg Ala His Phe Pro Leu Asp
            355                 360                 365

Val Gln Trp Asn Asp Leu Asp Tyr Met Asp Ser Arg Arg Asp Phe Thr
    370                 375                 380

Phe Asn Lys Asp Gly Phe Arg Asp Phe Pro Ala Met Val Gln Glu Leu
385                 390                 395                 400

His Gln Gly Gly Arg Arg Tyr Met Met Ile Val Asp Pro Ala Ile Ser
                405                 410                 415

Ser Ser Gly Pro Ala Gly Ser Tyr Arg Pro Tyr Asp Glu Gly Leu Arg
                420                 425                 430

Arg Gly Val Phe Ile Thr Asn Glu Thr Gly Gln Pro Leu Ile Gly Lys
            435                 440                 445

Val Trp Pro Gly Ser Thr Ala Phe Pro Asp Phe Thr Asn Pro Thr Ala
    450                 455                 460

Leu Ala Trp Trp Glu Asp Met Val Ala Glu Phe His Asp Gln Val Pro
465                 470                 475                 480

Phe Asp Gly Met Trp Ile Asp Met Asn Glu Pro Ser Asn Phe Ile Arg
                485                 490                 495

Gly Ser Glu Asp Gly Cys Pro Asn Asn Glu Leu Glu Asn Pro Pro Tyr
                500                 505                 510

Val Pro Gly Val Val Gly Gly Thr Leu Gln Ala Ala Thr Ile Cys Ala
            515                 520                 525

Ser Ser His Gln Phe Leu Ser Thr His Tyr Asn Leu His Asn Leu Tyr
    530                 535                 540

Gly Leu Thr Glu Ala Ile Ala Ser His Arg Ala Leu Val Lys Ala Arg
545                 550                 555                 560

Gly Thr Arg Pro Phe Val Ile Ser Arg Ser Thr Phe Ala Gly His Gly
                565                 570                 575

Arg Tyr Ala Gly His Trp Thr Gly Asp Val Trp Ser Ser Trp Glu Gln
            580                 585                 590

Leu Ala Ser Ser Val Pro Glu Ile Leu Gln Phe Asn Leu Leu Gly Val
            595                 600                 605

Pro Leu Val Gly Ala Asp Val Cys Gly Phe Leu Gly Asn Thr Ser Glu
    610                 615                 620

Glu Leu Cys Val Arg Trp Thr Gln Leu Gly Ala Phe Tyr Pro Phe Met
625                 630                 635                 640

Arg Asn His Asn Ser Leu Leu Ser Leu Pro Gln Glu Pro Tyr Ser Phe
                645                 650                 655

Ser Glu Pro Ala Gln Gln Ala Met Arg Lys Ala Leu Thr Leu Arg Tyr
            660                 665                 670
```

```
Ala Leu Leu Pro His Leu Tyr Thr Leu Phe His Gln Ala His Val Ala
        675             680             685

Gly Glu Thr Val Ala Arg Pro Leu Phe Leu Glu Phe Pro Lys Asp Ser
        690             695             700

Ser Thr Trp Thr Val Asp His Gln Leu Leu Trp Gly Glu Ala Leu Leu
705             710             715             720

Ile Thr Pro Val Leu Gln Ala Gly Lys Ala Glu Val Thr Gly Tyr Phe
            725             730             735

Pro Leu Gly Thr Trp Tyr Asp Leu Gln Thr Val Pro Val Glu Ala Leu
            740             745             750

Gly Ser Leu Pro Pro Pro Ala Ala Pro Arg Glu Pro Ala Ile His
        755             760             765

Ser Glu Gly Gln Trp Val Thr Leu Pro Ala Pro Leu Asp Thr Ile Asn
        770             775             780

Val His Leu Arg Ala Gly Tyr Ile Ile Pro Leu Gln Gly Pro Gly Leu
785             790             795             800

Thr Thr Thr Glu Ser Arg Gln Gln Pro Met Ala Leu Ala Val Ala Leu
            805             810             815

Thr Lys Gly Gly Glu Ala Arg Gly Glu Leu Phe Trp Asp Asp Gly Glu
            820             825             830

Ser Leu Glu Val Leu Glu Arg Gly Ala Tyr Thr Gln Val Ile Phe Leu
        835             840             845

Ala Arg Asn Asn Thr Ile Val Asn Glu Leu Val Arg Val Thr Ser Glu
        850             855             860

Gly Ala Gly Leu Gln Leu Gln Lys Val Thr Val Leu Gly Val Ala Thr
865             870             875             880

Ala Pro Gln Gln Val Leu Ser Asn Gly Val Pro Val Ser Asn Phe Thr
            885             890             895

Tyr Ser Pro Asp Thr Lys Val Leu Asp Ile Cys Val Ser Leu Leu Met
            900             905             910

Gly Glu Gln Phe Leu Val Ser Trp Cys
        915             920
```

```
<210> SEQ ID NO 36
<211> LENGTH: 917
<212> TYPE: PRT
<213> ORGANISM: artificial
<220> FEATURE:
<223> OTHER INFORMATION: sp7-HD NT1-13-D42-hGAAco1

<400> SEQUENCE: 36

Met Ala Phe Leu Trp Leu Leu Ser Cys Trp Ala Leu Leu Gly Thr Thr
1               5               10              15

Phe Gly Gln Leu Tyr Glu Asn Lys Pro Arg Arg Pro Tyr Ile Leu Gly
            20              25              30

Ala Pro Ala His Pro Gly Arg Pro Arg Ala Val Pro Thr Gln Cys Asp
        35              40              45

Val Pro Pro Asn Ser Arg Phe Asp Cys Ala Pro Asp Lys Ala Ile Thr
        50              55              60

Gln Glu Gln Cys Glu Ala Arg Gly Cys Cys Tyr Ile Pro Ala Lys Gln
65              70              75              80

Gly Leu Gln Gly Ala Gln Met Gly Gln Pro Trp Cys Phe Phe Pro Pro
            85              90              95

Ser Tyr Pro Ser Tyr Lys Leu Glu Asn Leu Ser Ser Ser Glu Met Gly
            100             105             110
```

```
Tyr Thr Ala Thr Leu Thr Arg Thr Thr Pro Thr Phe Phe Pro Lys Asp
        115                 120                 125

Ile Leu Thr Leu Arg Leu Asp Val Met Met Glu Thr Glu Asn Arg Leu
    130                 135                 140

His Phe Thr Ile Lys Asp Pro Ala Asn Arg Arg Tyr Glu Val Pro Leu
145                 150                 155                 160

Glu Thr Pro His Val His Ser Arg Ala Pro Ser Pro Leu Tyr Ser Val
                165                 170                 175

Glu Phe Ser Glu Glu Pro Phe Gly Val Ile Val Arg Arg Gln Leu Asp
            180                 185                 190

Gly Arg Val Leu Leu Asn Thr Thr Val Ala Pro Leu Phe Phe Ala Asp
            195                 200                 205

Gln Phe Leu Gln Leu Ser Thr Ser Leu Pro Ser Gln Tyr Ile Thr Gly
    210                 215                 220

Leu Ala Glu His Leu Ser Pro Leu Met Leu Ser Thr Ser Trp Thr Arg
225                 230                 235                 240

Ile Thr Leu Trp Asn Arg Asp Leu Ala Pro Thr Pro Gly Ala Asn Leu
                245                 250                 255

Tyr Gly Ser His Pro Phe Tyr Leu Ala Leu Glu Asp Gly Gly Ser Ala
            260                 265                 270

His Gly Val Phe Leu Leu Asn Ser Asn Ala Met Asp Val Val Leu Gln
            275                 280                 285

Pro Ser Pro Ala Leu Ser Trp Arg Ser Thr Gly Gly Ile Leu Asp Val
    290                 295                 300

Tyr Ile Phe Leu Gly Pro Glu Pro Lys Ser Val Val Gln Gln Tyr Leu
305                 310                 315                 320

Asp Val Val Gly Tyr Pro Phe Met Pro Pro Tyr Trp Gly Leu Gly Phe
            325                 330                 335

His Leu Cys Arg Trp Gly Tyr Ser Ser Thr Ala Ile Thr Arg Gln Val
        340                 345                 350

Val Glu Asn Met Thr Arg Ala His Phe Pro Leu Asp Val Gln Trp Asn
        355                 360                 365

Asp Leu Asp Tyr Met Asp Ser Arg Arg Asp Phe Thr Phe Asn Lys Asp
    370                 375                 380

Gly Phe Arg Asp Phe Pro Ala Met Val Gln Glu Leu His Gln Gly Gly
385                 390                 395                 400

Arg Arg Tyr Met Met Ile Val Asp Pro Ala Ile Ser Ser Ser Gly Pro
                405                 410                 415

Ala Gly Ser Tyr Arg Pro Tyr Asp Glu Gly Leu Arg Arg Gly Val Phe
            420                 425                 430

Ile Thr Asn Glu Thr Gly Gln Pro Leu Ile Gly Lys Val Trp Pro Gly
        435                 440                 445

Ser Thr Ala Phe Pro Asp Phe Thr Asn Pro Thr Ala Leu Ala Trp Trp
    450                 455                 460

Glu Asp Met Val Ala Glu Phe His Asp Gln Val Pro Phe Asp Gly Met
465                 470                 475                 480

Trp Ile Asp Met Asn Glu Pro Ser Asn Phe Ile Arg Gly Ser Glu Asp
                485                 490                 495

Gly Cys Pro Asn Asn Glu Leu Glu Asn Pro Pro Tyr Val Pro Gly Val
            500                 505                 510

Val Gly Gly Thr Leu Gln Ala Ala Thr Ile Cys Ala Ser Ser His Gln
        515                 520                 525

Phe Leu Ser Thr His Tyr Asn Leu His Asn Leu Tyr Gly Leu Thr Glu
```

```
        530                 535                 540

Ala Ile Ala Ser His Arg Ala Leu Val Lys Ala Arg Gly Thr Arg Pro
545                 550                 555                 560

Phe Val Ile Ser Arg Ser Thr Phe Ala Gly His Gly Arg Tyr Ala Gly
                565                 570                 575

His Trp Thr Gly Asp Val Trp Ser Ser Trp Glu Gln Leu Ala Ser Ser
                580                 585                 590

Val Pro Glu Ile Leu Gln Phe Asn Leu Leu Gly Val Pro Leu Val Gly
                595                 600                 605

Ala Asp Val Cys Gly Phe Leu Gly Asn Thr Ser Glu Glu Leu Cys Val
                610                 615                 620

Arg Trp Thr Gln Leu Gly Ala Phe Tyr Pro Phe Met Arg Asn His Asn
625                 630                 635                 640

Ser Leu Leu Ser Leu Pro Gln Glu Pro Tyr Ser Phe Ser Glu Pro Ala
                645                 650                 655

Gln Gln Ala Met Arg Lys Ala Leu Thr Leu Arg Tyr Ala Leu Leu Pro
                660                 665                 670

His Leu Tyr Thr Leu Phe His Gln Ala His Val Ala Gly Glu Thr Val
                675                 680                 685

Ala Arg Pro Leu Phe Leu Glu Phe Pro Lys Asp Ser Ser Thr Trp Thr
                690                 695                 700

Val Asp His Gln Leu Leu Trp Gly Glu Ala Leu Leu Ile Thr Pro Val
705                 710                 715                 720

Leu Gln Ala Gly Lys Ala Glu Val Thr Gly Tyr Phe Pro Leu Gly Thr
                725                 730                 735

Trp Tyr Asp Leu Gln Thr Val Pro Val Glu Ala Leu Gly Ser Leu Pro
                740                 745                 750

Pro Pro Pro Ala Ala Pro Arg Glu Pro Ala Ile His Ser Glu Gly Gln
                755                 760                 765

Trp Val Thr Leu Pro Ala Pro Leu Asp Thr Ile Asn Val His Leu Arg
                770                 775                 780

Ala Gly Tyr Ile Ile Pro Leu Gln Gly Pro Gly Leu Thr Thr Thr Glu
785                 790                 795                 800

Ser Arg Gln Gln Pro Met Ala Leu Ala Val Ala Leu Thr Lys Gly Gly
                805                 810                 815

Glu Ala Arg Gly Glu Leu Phe Trp Asp Asp Gly Glu Ser Leu Glu Val
                820                 825                 830

Leu Glu Arg Gly Ala Tyr Thr Gln Val Ile Phe Leu Ala Arg Asn Asn
                835                 840                 845

Thr Ile Val Asn Glu Leu Val Arg Val Thr Ser Glu Gly Ala Gly Leu
                850                 855                 860

Gln Leu Gln Lys Val Thr Val Leu Gly Val Ala Thr Ala Pro Gln Gln
865                 870                 875                 880

Val Leu Ser Asn Gly Val Pro Val Ser Asn Phe Thr Tyr Ser Pro Asp
                885                 890                 895

Thr Lys Val Leu Asp Ile Cys Val Ser Leu Leu Met Gly Glu Gln Phe
                900                 905                 910

Leu Val Ser Trp Cys
                915

<210> SEQ ID NO 37
<211> LENGTH: 909
<212> TYPE: PRT
<213> ORGANISM: artificial
```

<220> FEATURE:
<223> OTHER INFORMATION: sp7-HD NT9-13 -D42hGAAco1

<400> SEQUENCE: 37

```
Met Ala Phe Leu Trp Leu Leu Ser Cys Trp Ala Leu Leu Gly Thr Thr
1               5                   10                  15

Phe Gly Arg Pro Tyr Ile Leu Gly Ala Pro Ala His Pro Gly Arg Pro
            20                  25                  30

Arg Ala Val Pro Thr Gln Cys Asp Val Pro Pro Asn Ser Arg Phe Asp
            35                  40                  45

Cys Ala Pro Asp Lys Ala Ile Thr Gln Glu Gln Cys Glu Ala Arg Gly
        50                  55                  60

Cys Cys Tyr Ile Pro Ala Lys Gln Gly Leu Gln Gly Ala Gln Met Gly
65                  70                  75                  80

Gln Pro Trp Cys Phe Phe Pro Pro Ser Tyr Pro Ser Tyr Lys Leu Glu
                85                  90                  95

Asn Leu Ser Ser Ser Glu Met Gly Tyr Thr Ala Thr Leu Thr Arg Thr
            100                 105                 110

Thr Pro Thr Phe Phe Pro Lys Asp Ile Leu Thr Leu Arg Leu Asp Val
            115                 120                 125

Met Met Glu Thr Glu Asn Arg Leu His Phe Thr Ile Lys Asp Pro Ala
        130                 135                 140

Asn Arg Arg Tyr Glu Val Pro Leu Glu Thr Pro His Val His Ser Arg
145                 150                 155                 160

Ala Pro Ser Pro Leu Tyr Ser Val Glu Phe Ser Glu Glu Pro Phe Gly
                165                 170                 175

Val Ile Val Arg Arg Gln Leu Asp Gly Arg Val Leu Leu Asn Thr Thr
            180                 185                 190

Val Ala Pro Leu Phe Phe Ala Asp Gln Phe Leu Gln Leu Ser Thr Ser
            195                 200                 205

Leu Pro Ser Gln Tyr Ile Thr Gly Leu Ala Glu His Leu Ser Pro Leu
        210                 215                 220

Met Leu Ser Thr Ser Trp Thr Arg Ile Thr Leu Trp Asn Arg Asp Leu
225                 230                 235                 240

Ala Pro Thr Pro Gly Ala Asn Leu Tyr Gly Ser His Pro Phe Tyr Leu
                245                 250                 255

Ala Leu Glu Asp Gly Gly Ser Ala His Gly Val Phe Leu Leu Asn Ser
            260                 265                 270

Asn Ala Met Asp Val Val Leu Gln Pro Ser Pro Ala Leu Ser Trp Arg
        275                 280                 285

Ser Thr Gly Gly Ile Leu Asp Val Tyr Ile Phe Leu Gly Pro Glu Pro
        290                 295                 300

Lys Ser Val Val Gln Gln Tyr Leu Asp Val Val Gly Tyr Pro Phe Met
305                 310                 315                 320

Pro Pro Tyr Trp Gly Leu Gly Phe His Leu Cys Arg Trp Gly Tyr Ser
                325                 330                 335

Ser Thr Ala Ile Thr Arg Gln Val Val Glu Asn Met Thr Arg Ala His
            340                 345                 350

Phe Pro Leu Asp Val Gln Trp Asn Asp Leu Asp Tyr Met Asp Ser Arg
            355                 360                 365

Arg Asp Phe Thr Phe Asn Lys Asp Gly Phe Arg Asp Phe Pro Ala Met
        370                 375                 380

Val Gln Glu Leu His Gln Gly Gly Arg Arg Tyr Met Met Ile Val Asp
385                 390                 395                 400
```

Pro Ala Ile Ser Ser Ser Gly Pro Ala Gly Ser Tyr Arg Pro Tyr Asp
            405                 410                 415

Glu Gly Leu Arg Arg Gly Val Phe Ile Thr Asn Glu Thr Gly Gln Pro
            420                 425                 430

Leu Ile Gly Lys Val Trp Pro Gly Ser Thr Ala Phe Pro Asp Phe Thr
            435                 440                 445

Asn Pro Thr Ala Leu Ala Trp Trp Glu Asp Met Val Ala Glu Phe His
    450                 455                 460

Asp Gln Val Pro Phe Asp Gly Met Trp Ile Asp Met Asn Glu Pro Ser
465                 470                 475                 480

Asn Phe Ile Arg Gly Ser Glu Asp Gly Cys Pro Asn Asn Glu Leu Glu
            485                 490                 495

Asn Pro Pro Tyr Val Pro Gly Val Val Gly Gly Thr Leu Gln Ala Ala
            500                 505                 510

Thr Ile Cys Ala Ser Ser His Gln Phe Leu Ser Thr His Tyr Asn Leu
            515                 520                 525

His Asn Leu Tyr Gly Leu Thr Glu Ala Ile Ala Ser His Arg Ala Leu
    530                 535                 540

Val Lys Ala Arg Gly Thr Arg Pro Phe Val Ile Ser Arg Ser Thr Phe
545                 550                 555                 560

Ala Gly His Gly Arg Tyr Ala Gly His Trp Thr Gly Asp Val Trp Ser
            565                 570                 575

Ser Trp Glu Gln Leu Ala Ser Ser Val Pro Glu Ile Leu Gln Phe Asn
            580                 585                 590

Leu Leu Gly Val Pro Leu Val Gly Ala Asp Val Cys Gly Phe Leu Gly
            595                 600                 605

Asn Thr Ser Glu Glu Leu Cys Val Arg Trp Thr Gln Leu Gly Ala Phe
    610                 615                 620

Tyr Pro Phe Met Arg Asn His Asn Ser Leu Leu Ser Leu Pro Gln Glu
625                 630                 635                 640

Pro Tyr Ser Phe Ser Glu Pro Ala Gln Gln Ala Met Arg Lys Ala Leu
            645                 650                 655

Thr Leu Arg Tyr Ala Leu Leu Pro His Leu Tyr Thr Leu Phe His Gln
            660                 665                 670

Ala His Val Ala Gly Glu Thr Val Ala Arg Pro Leu Phe Leu Glu Phe
            675                 680                 685

Pro Lys Asp Ser Ser Thr Trp Thr Val Asp His Gln Leu Leu Trp Gly
    690                 695                 700

Glu Ala Leu Leu Ile Thr Pro Val Leu Gln Ala Gly Lys Ala Glu Val
705                 710                 715                 720

Thr Gly Tyr Phe Pro Leu Gly Thr Trp Tyr Asp Leu Gln Thr Val Pro
            725                 730                 735

Val Glu Ala Leu Gly Ser Leu Pro Pro Pro Ala Ala Pro Arg Glu
            740                 745                 750

Pro Ala Ile His Ser Glu Gly Gln Trp Val Thr Leu Pro Ala Pro Leu
            755                 760                 765

Asp Thr Ile Asn Val His Leu Arg Ala Gly Tyr Ile Ile Pro Leu Gln
    770                 775                 780

Gly Pro Gly Leu Thr Thr Thr Glu Ser Arg Gln Gln Pro Met Ala Leu
785                 790                 795                 800

Ala Val Ala Leu Thr Lys Gly Gly Glu Ala Arg Gly Glu Leu Phe Trp
            805                 810                 815

```
Asp Asp Gly Glu Ser Leu Glu Val Leu Glu Arg Gly Ala Tyr Thr Gln
            820                 825                 830

Val Ile Phe Leu Ala Arg Asn Asn Thr Ile Val Asn Glu Leu Val Arg
        835                 840                 845

Val Thr Ser Glu Gly Ala Gly Leu Gln Leu Gln Lys Val Thr Val Leu
        850                 855                 860

Gly Val Ala Thr Ala Pro Gln Gln Val Leu Ser Asn Gly Val Pro Val
865                 870                 875                 880

Ser Asn Phe Thr Tyr Ser Pro Asp Thr Lys Val Leu Asp Ile Cys Val
                885                 890                 895

Ser Leu Leu Met Gly Glu Gln Phe Leu Val Ser Trp Cys
                900                 905
```

<210> SEQ ID NO 38
<211> LENGTH: 2766
<212> TYPE: DNA
<213> ORGANISM: artificial
<220> FEATURE:
<223> OTHER INFORMATION: nucleic acid sequence encoding sp7-HD-spadin-
      D42-hGAAco1

<400> SEQUENCE: 38

```
atggcctttc tgtggctgct gagctgttgg gccctgctgg gcaccacctt cggcgctcca        60
cttcctcgtt ggagtggccc tatcggagtg tcttggggac tgagaggcgc gccgccccac       120
cccggcagac ctagagctgt gcctacccag tgtgacgtgc cccccaacag cagattcgac       180 tgcgccctg  acaaggccat cacccaggaa cagtgcgagg ccagaggctg ctgctacatc       240
cctgccaagc agggactgca gggcgctcag atgggacagc cctggtgctt cttcccaccc       300
tcctacccca gctacaagct ggaaaacctg agcagcagcg agatgggcta caccgccacc       360
ctgaccagaa ccacccccac attcttccca aaggacatcc tgaccctgcg gctggacgtg       420
atgatggaaa ccgagaaccg gctgcacttc accatcaagg accccgccaa tcggagatac       480
gaggtgcccc tggaaacccc ccacgtgcac tctagagccc ccagccctct gtacagcgtg       540
gaattcagcg aggaacccctt cggcgtgatc gtgcggagac agctggatgg cagagtgctg       600
ctgaacacca ccgtggcccc tctgttcttc gccgaccagt tcctgcagct gagcaccagc       660
ctgcccagcc agtacatcac aggactggcc gagcacctga ccccctgat  gctgagcaca       720 tcctggaccc ggatcaccct gtggaacagg gatctggccc ctaccccctgg cgccaatctg       780 tacggcagcc acccttctca cctggccctg aagatggcg  gatctgccca cggagtgttt       840
ctgctgaact ccaacgccat ggacgtggtg ctgcagccta ccctgccct  gtcttggaga       900 agcacaggcg gcatcctgga tgtgtacatc tttctgggcc ccgagcccaa gagcgtggtg       960
cagcagtatc tggatgtcgt gggctacccc ttcatgcccc cttactgggg cctgggattc      1020
cacctgtgca gatggggcta ctccagcacc gccatcacca gacaggtggt ggaaaacatg      1080
accagagccc acttcccact ggatgtgcag tggaacgacc tggactacat ggacagcaga      1140
cgggacttca ccttcaacaa ggacggcttc cgggacttcc ccgccatggt gcaggaactg      1200
catcagggcg gcagacggta catgatgatc gtggatcccg ccatcagctc ctctggccct      1260
gccggctctt acagaccctta cgacgagggc ctgcggagag cgtgttcat  caccaacgag      1320 acaggccagc ccctgatcgg caaagtgtgg cctggcagca gccttcccc  gacttcacc       1380 aatcctaccg ccctggcttg gtgggaggac atggtggccg agttccacga ccaggtgccc      1440
ttcgacggca tgtggatcga catgaacgag cccagcaact catccggggg cagcgaggat      1500
```

```
ggctgcccca acaacgaact ggaaaatccc ccttacgtgc ccggcgtcgt gggcggaaca      1560
ctgcaggccg ctacaatctg tgccagcagc caccagtttc tgagcaccca ctacaacctg      1620
cacaacctgt acggcctgac cgaggccatt gccagccacc gcgctctcgt gaaagccaga      1680
ggcacacggc ccttcgtgat cagcagaagc acctttgccg gccacggcag atacgccgga      1740
cattggactg gcgacgtgtg gtcctcttgg gagcagctgg cctctagcgt gcccgagatc      1800
ctgcagttca atctgctggg cgtgccactc gtgggcgccg atgtgtgtgg cttcctgggc      1860
aacacctccg aggaactgtg tgtgcggtgg acacagctgg cgccttcta cccttcatg      1920 agaaaccaca acagcctgct gagcctgccc caggaaccct acagctttag cgagcctgca      1980
cagcaggcca tgcggaaggc cctgacactg agatacgctc tgctgcccca cctgtacacc      2040
ctgtttcacc aggcccatgt ggccggcgag acagtggcca gacctctgtt tctggaattc      2100
cccaaggaca gcagcacctg accgtggac catcagctgc tgtggggaga ggctctgctg      2160
attaccccag tgctgcaggc aggcaaggcc gaagtgaccg gctactttcc cctgggcact      2220
tggtacgacc tgcagaccgt gcctgtggaa gccctgggat ctctgcctcc acctcctgcc      2280
gctcctagag agcctgccat tcactctgag ggccagtggg tcacactgcc tgcccccctg      2340
gataccatca acgtgcacct gagggccggc tacatcatac cactgcaggg acctggcctg      2400
accaccaccg agtctagaca gcagccaatg gccctggccg tggccctgac caaaggcgga      2460
gaagctaggg gcgagctgtt ctgggacgat ggcgagagcc tggaagtgct ggaaagaggc      2520 gcctatacccc aagtgatctt cctggcccgg aacaacacca tcgtgaacga gctggtgcgc      2580
gtgacctctg aaggcgctgg actgcagctg cagaaagtga ccgtgctggg agtggccaca      2640
gcccctcagc aggtgctgtc taatggcgtg cccgtgtcca acttcaccta cagccccgac      2700
accaaggtgc tggacatctg cgtgtcactg ctgatgggag agcagtttct ggtgtcctgg      2760
tgctga                                                                 2766
```

<210> SEQ ID NO 39
<211> LENGTH: 2754
<212> TYPE: DNA
<213> ORGANISM: artificial
<220> FEATURE:
<223> OTHER INFORMATION: nucleic acid sequence encoding sp7-HD NT1-13-
    D42-hGAAco1

<400> SEQUENCE: 39

```
atggccttc tgtggctgct gagctgttgg gccctgctgg gcaccaccttt cggccagctg        60 tacgagaaca gcccagacg gccctacatc ctgggcgcgc cggcccaccc cggcagacct       120
agagctgtgc ctacccagtg tgacgtgccc cccaacagca gattcgactg cgcccctgac       180
aaggccatca cccaggaaca gtgcgaggcc agaggctgct gctacatccc tgccaagcag       240
ggactgcagg cgctcagat gggacagccc tggtgcttct cccacccctc ctaccccagc       300
tacaagctgg aaaacctgag cagcagcgag atgggctaca ccgccacccct gaccagaacc       360 accccacat tcttcccaaa ggacatcctg accctgcggc tggacgtgat gatggaaacc       420
gagaaccggc tgcacttcac catcaaggac cccgccaatc ggagatacga ggtgcccctg       480
gaaacccccc acgtgcactc tagagcccccc agccctctgt acagcgtgga attcagcgag       540 gaaccttcg gcgtgatcgt gcggagacag ctggatggca gagtgctgct gaacaccacc       600
gtggcccctc tgttcttcgc cgaccagttc ctgcagctga gcaccagcct gcccagccag       660
tacatcacag gactggccga gcacctgagc ccctgatgc tgagcacatc ctggaccccgg       720
```

-continued

```
atcaccctgt ggaacaggga tctggcccct acccctggcg ccaatctgta cggcagccac      780
cctttctacc tggccctgga agatggcgga tctgcccacg gagtgtttct gctgaactcc      840
aacgccatgg acgtggtgct gcagcctagc cctgccctgt cttggagaag cacaggcggc      900
atcctggatg tgtacatctt tctgggcccc gagcccaaga gcgtggtgca gcagtatctg      960
gatgtcgtgg gctacccctt catgcccccct tactggggcc tgggattcca cctgtgcaga     1020
tggggctact ccagcaccgc catcaccaga caggtggtgg aaaacatgac cagagcccac     1080
ttcccactgg atgtgcagtg gaacgacctg gactacatgg acagcagacg ggacttcacc     1140
ttcaacaagg acggcttccg ggacttcccc gccatggtgc aggaactgca tcagggcggc     1200
agacggtaca tgatgatcgt ggatcccgcc atcagctcct ctggccctgc cggctcttac     1260
agaccctacg acgagggcct gcggagaggc gtgttcatca ccaacgagac aggccagccc     1320
ctgatcggca aagtgtggcc tggcagcaca gccttccccg acttcaccaa tcctaccgcc     1380
ctggcttggt gggaggacat ggtggccgag ttccacgacc aggtgcccctt cgacggcatg     1440 tggatcgaca tgaacgagcc cagcaacttc atccggggca gcgaggatgg ctgccccaac     1500
aacgaactgg aaaatccccc ttacgtgccc ggcgtcgtgg gcggaacact gcaggccgct     1560
acaatctgtg ccagcagcca ccagtttctg agcacccact acaacctgca caacctgtac     1620
ggcctgaccg aggccattgc cagccaccgc gctctcgtga agccagagg cacacggccc      1680 ttcgtgatca gcaagaagcac ctttgccggc cacggcagat acgccggaca ttggactggc     1740
gacgtgtggt cctcttggga gcagctggcc tctagcgtgc ccgagatcct gcagttcaat     1800
ctgctgggcg tgccactcgt gggcgccgat gtgtgtggct tcctgggcaa cacctccgag     1860
gaactgtgtg tgcggtggac acagctgggc gccttctacc ctttcatgag aaaccacaac     1920
agcctgctga gctgccccca ggaaccctac agctttagcg agcctgcaca gcaggccatg     1980
cggaaggccc tgacactgag atacgctctg ctgccccacc tgtacaccct gtttcaccag     2040
gcccatgtgg ccggcgagac agtggccaga cctctgtttc tggaattccc caaggacagc     2100
agcacctgga ccgtggacca tcagctgctg tggggagagg ctctgctgat accccagtg      2160 ctgcaggcag gcaaggccga agtgaccggc tactttcccc tgggcacttg gtacgacctg     2220
cagaccgtgc ctgtggaagc cctgggatct ctgcctccac ctcctgccgc tcctagagag     2280
cctgccattc actctgaggg ccagtgggtc acactgcctg ccccccctgga taccatcaac     2340 gtgcacctga gggccggcta tcatcatacca ctgcagggac ctggcctgac caccaccgag     2400
tctagacagc agccaatggc cctggccgtg gccctgacca aaggcggaga gctaggggc      2460 gagctgttct gggacgatgg cgagagcctg gaagtgctgg aaagaggcgc ctatacccaa     2520
gtgatcttcc tggcccggaa caacaccatc gtgaacgagc tggtgcgcgt gacctctgaa     2580
ggcgctggac tgcagctgca gaaagtgacc gtgctggag tggccacagc ccctcagcag      2640
gtgctgtcta tggcgtgcc cgtgtccaac ttcacctaca gccccgacac caaggtgctg      2700
gacatctgcg tgtcactgct gatgggagag cagtttctgg tgtcctggtg ctga          2754
```

<210> SEQ ID NO 40
<211> LENGTH: 2730
<212> TYPE: DNA
<213> ORGANISM: artificial
<220> FEATURE:
<223> OTHER INFORMATION: nucleic acid sequence encoding sp7-HD NT 9-13
      -D42hGAAco1

<400> SEQUENCE: 40

-continued

```
atggcctttc tgtggctgct gagctgttgg gccctgctgg gcaccacctt cggccggccc        60
tacatcctgg gcgcgccggc ccaccccggc agacctagag ctgtgcctac ccagtgtgac       120
gtgcccccca acagcagatt cgactgcgcc cctgacaagg ccatcaccca ggaacagtgc       180
gaggccagag gctgctgcta catccctgcc aagcagggac tgcagggcgc tcagatggga       240
cagccctggt gcttcttccc accctcctac cccagctaca agctggaaaa cctgagcagc       300
agcgagatgg gctacaccgc caccctgacc agaaccaccc ccacattctt cccaaaggac       360
atcctgaccc tgcggctgga cgtgatgatg gaaaccgaga accggctgca cttcaccatc       420
aaggaccccg ccaatcggag atacgaggtg cccctggaaa cccccacgt gcactctaga       480 gcccccagcc ctctgtacag cgtggaattc agcgaggaac ccttcggcgt gatcgtgcgg       540
agacagctgg atggcagagt gctgctgaac accaccgtgg cccctctgtt cttcgccgac       600
cagttcctgc agctgagcac cagcctgccc agccagtaca tcacaggact ggccgagcac       660
ctgagccccc tgatgctgag cacatcctgg acccggatca ccctgtggaa cagggatctg       720
gcccctaccc ctggcgccaa tctgtacggc agccacccctt tctacctggc cctggaagat       780
ggcggatctg cccacggagt gtttctgctg aactccaacg ccatggacgt ggtgctgcag       840
cctagccctg ccctgtcttg gagaagcaca ggcggcatcc tggatgtgta catctttctg       900
ggccccgagc ccaagagcgt ggtgcagcag tatctggatg tcgtgggcta ccccttcatg       960
cccccttact ggggcctggg attccacctg tgcagatggg gctactccag caccgccatc      1020
accagacagg tggtggaaaa catgaccaga gcccacttcc cactggatgt gcagtggaac      1080
gacctggact acatggacag cagacgggac ttcaccttca caaggacgg cttccgggac      1140 ttccccgcca tggtgcagga actgcatcag ggcggcagac ggtacatgat gatcgtggat      1200
cccgccatca gctcctctgg ccctgccggc tcttacagac cctacgacga gggcctgcgg      1260
agaggcgtgt tcatcaccaa cgagacaggc cagcccctga tcggcaaagt gtggcctggc      1320
agcacagcct tccccgactt caccaatcct accgccctgg cttggtggga ggacatggtg      1380
gccgagttcc acgaccaggt gcccttcgac ggcatgtgga tcgacatgaa cgagcccagc      1440
aacttcatcc ggggcagcga ggatggctgc cccaacaacg aactggaaaa tccccccttac      1500 gtgcccggcg tcgtgggcgg aacactgcag gccgctacaa tctgtgccag cagccaccag      1560
tttctgagca cccactacaa cctgcacaac ctgtacggcc tgaccgaggc cattgccagc      1620
caccgcgctc tcgtgaaagc cagaggcaca cggcccttcg tgatcagcag aagcaccttt      1680 gccgccacg gcagatacgc cggacattgg actggcgacg tgtggtcctc ttgggagcag      1740
ctggcctcta gcgtgcccga gatcctgcag ttcaatctgc tgggcgtgcc actcgtgggc      1800
gccgatgtgt gtggcttcct gggcaacacc tccgaggaac tgtgtgtgcg gtggacacag      1860
ctgggcgcct tctacccttt catgagaaac cacaacagcc tgctgagcct gccccaggaa      1920
ccctacagct ttagcgagcc tgcacagcag gccatgcgga aggccctgac actgagatac      1980
gctctgctgc cccacctgta caccctgttt caccaggccc atgtggccgg cgagacagtg      2040
gccagacctc tgtttctgga attccccaag acagcagca cctggaccgt ggaccatcag      2100
ctgctgtggg gagaggctct gctgattacc ccagtgctgc aggcaggcaa ggccgaagtg      2160
accggctact ttccctgggc acttggtac gacctgcaga ccgtgcctgt ggaagccctg      2220
ggatctctgc ctccacctcc tgccgctcct agagagcctg ccattcactc tgagggccag      2280
tgggtcacac tgcctgcccc cctggatacc atcaacgtgc acctgagggc cggctacatc      2340
ataccactgc agggacctgg cctgaccacc accgagtcta gacagcagcc aatggccctg      2400
```

-continued

```
gccgtggccc tgaccaaagg cggagaagct aggggcgagc tgttctggga cgatggcgag    2460
agcctggaag tgctggaaag aggcgcctat acccaagtga tcttcctggc ccggaacaac    2520
accatcgtga acgagctggt gcgcgtgacc tctgaaggcg ctggactgca gctgcagaaa    2580
gtgaccgtgc tgggagtggc cacagcccct cagcaggtgc tgtctaatgg cgtgcccgtg    2640
tccaacttca cctacagccc cgacaccaag gtgctggaca tctgcgtgtc actgctgatg    2700
ggagagcagt ttctggtgtc ctggtgctga                                     2730

<210> SEQ ID NO 41
<211> LENGTH: 4258
<212> TYPE: DNA
<213> ORGANISM: artificial
<220> FEATURE:
<223> OTHER INFORMATION: ApoE-hAAT-modified HBB2 intron-sp7-Spadin-
      D42-hGAAco1-bgHpolyA

<400> SEQUENCE: 41
aggctcagag gcacacagga gtttctgggc tcaccctgcc cccttccaac ccctcagttc      60
ccatcctcca gcagctgttt gtgtgctgcc tctgaagtcc acactgaaca aacttcagcc     120
tactcatgtc cctaaaatgg gcaaacattg caagcagcaa acagcaaaca cacagccctc     180
cctgcctgct gaccttggag ctggggcaga ggtcagagac ctctctgggc ccatgccacc     240
tccaacatcc actcgacccc ttggaatttc ggtggagagg agcagaggtt gtcctggcgt     300
ggtttaggta gtgtgagagg ggtacccggg gatcttgcta ccagtggaac agccactaag     360
gattctgcag tgagagcaga gggccagcta agtggtactc tcccagagac tgtctgactc     420
acgccacccc ctccaccttg gacacaggac gctgtggttt ctgagccagg tacaatgact     480
cctttcggta agtgcagtgg aagctgtaca ctgcccaggc aaagcgtccg ggcagcgtag     540
gcgggcgact cagatcccag ccagtggact tagcccctgt ttgctcctcc gataactggg     600
gtgaccttgg ttaatattca ccagcagcct ccccgttgc ccctctggat ccactgctta     660
aatacggacg aggacagggc cctgtctcct cagcttcagg caccaccact gacctgggac     720
agtgaataga tcctgagaac ttcagggtga gtctatggga cccttgatgt tttctttccc     780 cttctttct atggttaagt tcatgtcata ggaaggggag aagtaacagg gtacacatat     840
tgaccaaatc agggtaattt tgcatttgta attttaaaaa atgctttctt cttttaatat     900
acttttttgt ttatcttatt ctaatactt tccctaatct ctttctttca gggcaataat     960
gatacaatgt atcatgcctc tttgcaccat tctaaagaat aacagtgata atttctgggt    1020
taaggcaata gcaatatttc tgcatataaa tatttctgca tataaattgt aactgatgta    1080
agaggtttca tattgctaat agcagctaca atccagctac cattctgctt ttattttctg    1140
gttgggataa ggctggatta ttctgagtcc aagctaggcc cttttgctaa tcttgttcat    1200
acctcttatc ttcctcccac agctcctggg caacctgctg tctctctgc tggcccatca    1260 ctttggcaaa gcacgcgtgc caccatggcc tttctgtggc tgctgagctg ttgggccctg    1320
ctgggcacca ccttcggcgc tccacttcct cgttggagtg ccctatcgg agtgtcttgg    1380 ggactgagag gcgcgccggc ccaccccggc agacctagct ctgtgcctac ccagtgtgac    1440
gtgcccccca acagcagatt cgactgcgcc cctgacaagg ccatcaccca ggaacagtgc    1500
gaggccagag gctgctgcta catccctgcc aagcagggac tgcagggcgc tcagatggga    1560
cagccctggt gcttcttccc accctcctac cccagctaca gctggaaaa cctgagcagc    1620 agcgagatgg gctacaccgc caccctgacc agaaccaccc ccacattctt cccaaaggac    1680
```

-continued

```
atcctgaccc tgcggctgga cgtgatgatg gaaaccgaga accggctgca cttcaccatc    1740
aaggaccccg ccaatcggag atacgaggtg cccctggaaa cccccacgt gcactctaga    1800 gcccccagcc ctctgtacag cgtggaattc agcgaggaac ccttcggcgt gatcgtgcgg    1860
agacagctga tggcagagt gctgctgaac accaccgtgg cccctctgtt cttcgccgac    1920
cagttcctgc agctgagcac cagcctgccc agccagtaca tcacaggact ggccgagcac    1980 ctgagcccc tgatgctgag cacatcctgg acccggatca ccctgtggaa cagggatctg    2040
gcccctaccc ctggcgccaa tctgtacggc agccaccctt tctacctggc cctggaagat    2100
ggcggatctg cccacggagt gtttctgctg aactccaacg ccatggacgt ggtgctgcag    2160
cctagccctg ccctgtcttg gagaagcaca ggcggcatcc tggatgtgta catctttctg    2220
ggccccgagc ccaagagcgt ggtgcagcag tatctggatg tcgtgggcta ccccttcatg    2280
cccccttact ggggcctggg attccacctg tgcagatggg gctactccag caccgccatc    2340
accagacagg tggtggaaaa catgaccaga gcccacttcc cactggatgt gcagtggaac    2400
gacctggact acatggacag cagacgggac ttcaccttca caaggacgg cttccgggac    2460 ttccccgcca tggtgcagga actgcatcag ggcggcagac ggtacatgat gatcgtggat    2520
cccgccatca gctcctctgg ccctgccggc tcttacagac cctacgacga gggcctgcgg    2580
agaggcgtgt tcatcaccaa cgagacaggc cagcccctga tcggcaaagt gtggcctggc    2640
agcacagcct tccccgactt caccaatcct accgccctgg cttggtggga ggacatggtg    2700
gccgagttcc acgaccaggt gcccttcgac ggcatgtgga tcgacatgaa cgagcccagc    2760
aacttcatcc ggggcagcga ggatggctgc cccaacaacg aactggaaaa tccccccttac    2820 gtgcccggcg tcgtgggcgg aacactgcag gccgctacaa tctgtgccag cagccaccag    2880
tttctgagca cccactacaa cctgcacaac ctgtacggcc tgaccgaggc cattgccagc    2940
caccgcgctc tcgtgaaagc cagaggcaca cggcccttcg tgatcagcag aagcaccttt    3000
gccggccacg gcagatacgc cggacattgg actggcgacg tgtggtcctc ttgggagcag    3060
ctggcctcta gcgtgcccga gatcctgcag ttcaatctgc tgggcgtgcc actcgtgggc    3120
gccgatgtgt gtggcttcct gggcaacacc tccgaggaac tgtgtgtgcg gtggacacag    3180
ctgggcgcct tctacccttt catgagaaac cacaacagcc tgctgagcct gccccaggaa    3240
ccctacagct ttagcgagcc tgcacagcag gccatgcgga aggccctgac actgagatac    3300
gctctgctgc cccacctgta caccctgttt caccaggccc atgtggccgg cgagacagtg    3360
gccagacctc tgtttctgga attccccaag gacagcagca cctggaccgt ggaccatcag    3420
ctgctgtggg gagaggctct gctgattacc ccagtgctgc aggcaggcaa ggccgaagtg    3480
accggctact ttcccctggg cacttggtac gacctgcaga ccgtgcctgt ggaagccctg    3540
ggatctctgc ctccacctcc tgccgctcct agagagcctg ccattcactc tgagggccag    3600
tgggtcacac tgcctgcccc cctggatacc atcaacgtgc acctgagggc cggctacatc    3660
ataccactgc agggacctgg cctgaccacc accgagtcta gacagcagcc aatggccctg    3720
gccgtggccc tgaccaaagg cggagaagct aggggcgagc tgttctggga cgatggcgag    3780
agcctggaag tgctggaaag aggcgcctat acccaagtga tcttcctggc ccggaacaac    3840
accatcgtga acgagctggt gcgcgtgacc tctgaaggcg ctggactgca gctgcagaaa    3900
gtgaccgtgc tgggagtggc cacagccccct cagcaggtgc tgtctaatgg cgtgcccgtg    3960
tccaacttca cctacagccc cgacaccaag gtgctggaca tctgcgtgtc actgctgatg    4020
```

-continued

```
ggagagcagt ttctggtgtc ctggtgctga ctcgagagat ctaccggtga attcaccgcg   4080
ggtttaaact gtgccttcta gttgccagcc atctgttgtt tgcccctccc ccgtgccttc   4140
cttgaccctg gaaggtgcca ctcccactgt cctttcctaa taaaatgagg aaattgcatc   4200
gcattgtctg agtaggtgtc attctattct gggggtgggg tgggggcta gctctaga     4258
```

```
<210> SEQ ID NO 42
<211> LENGTH: 4246
<212> TYPE: DNA
<213> ORGANISM: artificial
<220> FEATURE:
<223> OTHER INFORMATION: ApoE-hAAT-modified HBB2 intron-sp7-HD-NT1-13-
      D42-hGAAco1-bgHpolyA

<400> SEQUENCE: 42
```

```
aggctcagag gcacacagga gtttctgggc tcaccctgcc cccttccaac ccctcagttc     60
ccatcctcca gcagctgttt gtgtgctgcc tctgaagtcc acactgaaca aacttcagcc    120
tactcatgtc cctaaaatgg gcaaacattg caagcagcaa acagcaaaca cacagccctc    180
cctgcctgct gaccttggag ctggggcaga ggtcagagac ctctctgggc ccatgccacc    240
tccaacatcc actcgacccc ttggaatttc ggtggagagg agcagaggtt gtcctggcgt    300
ggtttaggta gtgtgagagg ggtacccggg gatcttgcta ccagtggaac agccactaag    360
gattctgcag tgagagcaga gggccagcta agtggtactc tcccagagac tgtctgactc    420
acgccacccc ctccaccttg gacacaggac gctgtggttt ctgagccagg tacaatgact    480
cctttcggta agtgcagtgg aagctgtaca ctgcccaggc aaagcgtccg ggcagcgtag    540
gcgggcgact cagatcccag ccagtggact tagccctgt ttgctcctcc gataactggg     600
gtgaccttgg ttaatattca ccagcagcct ccccgttgc ccctctggat ccactgctta     660
aatacggacg aggacagggc cctgtctcct cagcttcagg caccaccact gacctgggac    720
agtgaataga tcctgagaac ttcagggtga gtctatggga cccttgatgt tttctttccc    780 cttctttttct atggttaagt tcatgtcata ggaaggggag aagtaacagg gtacacatat    840
tgaccaaatc agggtaattt tgcatttgta attttaaaaa atgctttctt cttttaatat    900
acttttttgt ttatcttatt ctaatacttt tccctaatct ctttctttca gggcaataat    960
gatacaatgt atcatgcctc tttgcaccat tctaaagaat aacagtgata atttctgggt   1020
taaggcaata gcaatatttc tgcatataaa tatttctgca tataaattgt aactgatgta   1080
agaggtttca tattgctaat agcagctaca atccagctac cattctgctt ttattttctg   1140
gttgggataa ggctggatta ttctgagtcc aagctaggcc cttttgctaa tcttgttcat   1200
acctcttatc ttcctcccac agctcctggg caacctgctg gtctctctgc tggcccatca   1260
ctttggcaaa gcacgcgtgc caccatggcc tttctgtggc tgctgagctg ttgggccctg   1320
ctgggcacca ccttcggcca gctgtacgag aacaagccca gacggcccta catcctgggc   1380
gcgccggccc accccggcag acctagagct gtgcctaccc agtgtgacgt gccccccaac   1440
agcagattcg actgcgcccc tgacaaggcc atcacccagg aacagtgcga ggccagaggc   1500
tgctgctaca tccctgccaa gcagggactg cagggcgctc agatgggaca gccctggtgc   1560
ttcttcccac cctcctaccc cagctacaag ctggaaaacc tgagcagcag cgagatgggc   1620
tacaccgcca ccctgaccag aaccacccc acattcttcc caaaggacat cctgacctg   1680 cggctggacg tgatgatgga aaccgagaac cggctgcact tcaccatcaa ggaccccgcc   1740
aatcggagat acgaggtgcc cctggaaacc ccccacgtgc actctagagc ccccagccct   1800
```

```
ctgtacagcg tggaattcag cgaggaaccc ttcggcgtga tcgtgcggag acagctggat    1860
ggcagagtgc tgctgaacac caccgtggcc cctctgttct tcgccgacca gttcctgcag    1920
ctgagcacca gcctgcccag ccagtacatc acaggactgg ccgagcacct gagcccctg     1980 atgctgagca tcctggac   ccggatcacc ctgtggaaca gggatctggc ccctacccct    2040
ggcgccaatc tgtacggcag ccacccttc  tacctggccc tggaagatgg cggatctgcc    2100
cacggagtgt ttctgctgaa ctccaacgcc atggacgtgg tgctgcagcc tagccctgcc    2160
ctgtcttgga gaagcacagg cggcatcctg gatgtgtaca tctttctggg ccccgagccc    2220
aagagcgtgg tgcagcagta tctggatgtc gtgggctacc ccttcatgcc cccttactgg    2280
ggcctgggat ccacctgtg  cagatggggc tactccagca ccgccatcac cagacaggtg    2340
gtggaaaaca tgaccagagc ccacttccca ctggatgtgc agtggaacga cctggactac    2400
atggacagca gacgggactt caccttcaac aaggacggct ccgggacttt ccccgccatg    2460
gtgcaggaac tgcatcaggg cggcagacgg tacatgatga tcgtggatcc cgccatcagc    2520
tcctctggcc ctgccggctc ttacagaccc tacgacgagg gcctgcggag aggcgtgttc    2580
atcaccaacg agacaggcca gcccctgatc ggcaaagtgt ggcctggcag cacagccttc    2640
cccgacttca ccaatcctac cgccctggct tggtgggagg acatggtggc cgagttccac    2700
gaccaggtgc ccttcgacgg catgtggatc gacatgaacg agcccagcaa cttcatccgg    2760
ggcagcgagg atgctgccc  caacaacgaa ctggaaaatc cccttacgt  gcccggcgtc    2820 gtgggcggaa cactgcaggc cgctacaatc tgtgccagca gccaccagtt tctgagcacc    2880
cactacaacc tgcacaacct gtacggcctg accgaggcca ttgccagcca ccgcgctctc    2940
gtgaaagcca gaggcacacg gcccttcgtg atcagcagaa gcacctttgc cggccacggc    3000
agatacgccg gacattggac tggcgacgtg tggtcctctt gggagcagct ggcctctagc    3060
gtgcccgaga tcctgcagtt caatctgctg ggcgtgccac tcgtgggcgc cgatgtgtgt    3120
ggcttcctgg gcaacacctc cgaggaactg tgtgtgcggt ggacacagct gggcgccttc    3180 tacccttca  tgagaaacca caacagcctg ctgagcctgc cccaggaacc ctacagcttt    3240
agcgagcctg cacagcaggc catgcggaag gccctgacac tgagatacgc tctgctgccc    3300
cacctgtaca ccctgtttca ccaggcccat gtggccggcg agacagtggc cagacctctg    3360
tttctggaat cccccaagga cagcagcacc tggaccgtgg accatcagct gctgtgggga    3420
gaggctctgc tgattacccc agtgctgcag gcaggcaagg ccgaagtgac cggctacttt    3480
cccctgggca cttggtacga cctgcagacc gtgcctgtgg aagccctggg atctctgcct    3540
ccacctcctg ccgctcctag agagcctgcc attcactctg agggccagtg ggtcacactg    3600
cctgcccccc tggataccat caacgtgcac ctgagggccg gctacatcat accactgcag    3660
ggacctggcc tgaccaccac cgagtctaga cagcagccaa tggccctggc cgtggccctg    3720
accaaaggcg agaagctagg ggcgagctg  ttctgggacg atggcgagag cctggaagtg    3780
ctggaaagag gcgcctatac ccaagtgatc ttcctggccc ggaacaacac catcgtgaac    3840
gagctggtgc gcgtgaccctc tgaaggcgct ggactgcagc tgcagaaagt gaccgtgctg    3900
ggagtggcca cagcccctca gcaggtgctg tctaatggcg tgcccgtgtc caacttcacc    3960
tacagccccg acaccaaggt gctggacatc tgcgtgtcac tgctgatggg agagcagttt    4020
ctggtgtcct ggtgctgact cgagagatct accggtgaat tcaccgcggg tttaaactgt    4080 gccttcagt  tgccagccat ctgttgtttg ccccctcccc gtgccttcct tgaccctgga    4140
aggtgccact cccactgtcc tttcctaata aaatgaggaa attgcatcgc attgtctgag    4200
```

-continued

```
taggtgtcat tctattctgg ggggtggggt gggggctagc tctaga                60
```

<210> SEQ ID NO 43
<211> LENGTH: 4222
<212> TYPE: DNA
<213> ORGANISM: artificial
<220> FEATURE:
<223> OTHER INFORMATION: ApoE-hAAT-modified HBB2 intron-sp7-HD-NT9-13-
      D42-hGAAco1-bgHpolyA

<400> SEQUENCE: 43

```
aggctcagag gcacacagga gtttctgggc tcaccctgcc cccttccaac ccctcagttc      60
ccatcctcca gcagctgttt gtgtgctgcc tctgaagtcc acactgaaca aacttcagcc     120
tactcatgtc cctaaaatgg gcaaacattg caagcagcaa acagcaaaca cacagccctc     180
cctgcctgct gaccttggag ctggggcaga ggtcagagac ctctctgggc ccatgccacc     240
tccaacatcc actcgacccc ttggaatttc ggtggagagg agcagaggtt gtcctggcgt     300
ggtttaggta gtgtgagagg ggtacccggg gatcttgcta ccagtggaac agccactaag     360
gattctgcag tgagagcaga gggccagcta agtggtactc tcccagagac tgtctgactc     420
acgccacccc ctccaccttg gacacaggac gctgtggttt ctgagccagg tacaatgact     480
cctttcggta agtgcagtgg aagctgtaca ctgcccaggc aaagcgtccg ggcagcgtag     540
gcgggcgact cagatcccag ccagtggact tagcccctgt ttgctcctcc gataactggg     600
gtgaccttgg ttaatattca ccagcagcct ccccgttgc ccctctggat ccactgctta     660
aatacggacg aggacaggc cctgtctcct cagcttcagg caccaccact gacctgggac     720
agtgaataga tcctgagaac ttcagggtga gtctatggga cccttgatgt tttctttccc     780
cttcttttct atggttaagt tcatgtcata ggaaggggag aagtaacagg gtacacatat     840
tgaccaaatc agggtaattt tgcatttgta attttaaaaa atgctttctt cttttaatat     900
acttttttgt ttatcttatt ctaatactt tccctaatct ctttctttca gggcaataat     960
gatacaatgt atcatgcctc tttgcaccat tctaaagaat aacagtgata atttctgggt    1020
taaggcaata gcaatatttc tgcatataaa tatttctgca tataaattgt aactgatgta    1080
agaggtttca tattgctaat agcagctaca atccagctac cattctgctt ttattttctg    1140
gttgggataa ggctggatta ttctgagtcc aagctaggcc cttttgctaa tcttgttcat    1200
acctcttatc ttcctcccac agctcctggg caacctgctg gtctctctgc tggcccatca    1260
ctttggcaaa gcacgcgtgc caccatggcc tttctgtggc tgctgagctg ttgggccctg    1320
ctgggcacca ccttcggccg gcctacatc ctgggcgcgc cggcccaccc cggcagacct    1380
agagctgtgc ctacccagtg tgacgtgccc cccaacagca gattcgactg cgcccctgac    1440
aaggccatca cccaggaaca gtgcgaggcc agaggctgct gctacatccc tgccaagcag    1500
ggactgcagg gcgctcagat gggacagccc tggtgcttct cccaccctc ctacccagc     1560 tacaagctgg aaaacctgag cagcagcgag atgggctaca ccgccaccct gaccagaacc    1620
acccccacat tcttcccaaa ggacatcctg accctgcggc tggacgtgat gatggaaacc    1680
gagaaccggc tgcacttcac catcaaggac cccgccaatc ggagatacga ggtgcccctg    1740
gaaacccccc acgtgcactc tagagcccc agccctctgt acagcgtgga attcagcgag    1800 gaaccttcg gcgtgatcgt gcggagacac ctggatggca gagtgctgct gaacaccacc    1860
gtggcccctg tgttcttcgc cgaccagttc ctgcagctga gcaccagcct gcccagccag    1920
tacatcacag gactggccga gcacctgagc cccctgatgc tgagcacatc ctggaccggg    1980
```

```
atcaccctgt ggaacaggga tctggcccct acccctggcg ccaatctgta cggcagccac      2040
cctttctacc tggccctgga agatggcgga tctgcccacg gagtgtttct gctgaactcc      2100
aacgccatgg acgtggtgct gcagcctagc cctgccctgt cttggagaag cacaggcggc      2160
atcctggatg tgtacatctt tctgggcccc gagcccaaga gcgtggtgca gcagtatctg      2220
gatgtcgtgg gctacccctt catgcccccct tactggggcc tgggattcca cctgtgcaga     2280
tggggctact ccagcaccgc catcaccaga caggtggtgg aaaacatgac cagagcccac      2340
ttcccactgg atgtgcagtg gaacgacctg gactacatgg acagcagacg ggacttcacc      2400
ttcaacaagg acggcttccg ggacttcccc gccatggtgc aggaactgca tcagggcggc      2460
agacggtaca tgatgatcgt ggatcccgcc atcagctcct ctggccctgc cggctcttac      2520
agaccctacg acgagggcct gcggagaggc gtgttcatca ccaacgagac aggccagccc      2580
ctgatcggca aagtgtggcc tggcagcaca gccttccccg acttcaccaa tcctaccgcc      2640
ctggcttggt gggaggacat ggtggccgag ttccacgacc aggtgcccctt cgacggcatg      2700 tggatcgaca tgaacgagcc cagcaacttc atccggggca gcgaggatgg ctgccccaac      2760
aacgaactgg aaaatccccc ttacgtgccc ggcgtcgtgg gcggaacact gcaggccgct      2820
acaatctgtg ccagcagcca ccagtttctg agcacccact acaacctgca caacctgtac      2880
ggcctgaccg aggccattgc cagccaccgc gctctcgtga aagccagagg cacacggccc      2940
ttcgtgatca gcagaagcac ctttgccggc cacggcagat acgccggaca ttggactggc      3000
gacgtgtggt cctcttggga gcagctggcc tctagcgtgc ccgagatcct gcagttcaat      3060
ctgctgggcg tgccactcgt gggcgccgat gtgtgtggct tcctgggcaa cacctccgag      3120
gaactgtgtg tgcggtggac acagctgggc gccttctacc ctttcatgag aaaccacaac      3180
agcctgctga gcctgcccca ggaaccctac agctttagcg agcctgcaca gcaggccatg      3240
cggaaggccc tgacactgag atacgctctg ctgccccacc tgtacaccct gtttcaccag      3300
gcccatgtgg ccggcgagac agtggccaga cctctgtttc tggaattccc caaggacagc      3360
agcacctgga ccgtggacca tcagctgctg tggggagagg ctctgctgat taccccagtg      3420
ctgcaggcag gcaaggccga agtgaccggc tactttcccc tgggcacttg gtacgacctg      3480
cagaccgtgc ctgtggaagc cctgggatct ctgcctccac ctcctgccgc tcctagagag      3540
cctgccattc actctgaggg ccagtgggtc acactgcctg cccccctgga taccatcaac      3600
gtgcacctga gggccggcta catcatacca ctgcagggac ctggcctgac caccaccgag      3660
tctagacagc agccaatggc cctggccgtg gccctgacca aaggcggaga agctaggggc      3720
gagctgttct gggacgatgg cgagagcctg gaagtgctgg aaagaggcgc ctatacccaa      3780
gtgatcttcc tggcccggaa caacaccatc gtgaacgagc tggtgcgcgt gacctctgaa      3840
ggcgctggac tgcagctgca gaaagtgacc gtgctgggag tggccacagc ccctcagcag      3900
gtgctgtcta tggcgtgcc cgtgtccaac ttcacctaca gccccgacac caaggtgctg      3960
gacatctgcg tgtcactgct gatgggagag cagtttctgg tgtcctggtg ctgactcgag      4020
agatctaccg gtgaattcac cgcgggttta aactgtgcct tctagttgcc agccatctgt      4080
tgtttgcccc tcccccgtgc cttccttgac cctggaaggt gccactccca ctgtcctttc      4140
ctaataaaat gaggaaattg catcgcattg tctgagtagg tgtcattcta ttctggggg      4200 tggggtgggg gctagctcta ga                                                4222
```

<210> SEQ ID NO 44

-continued

```
<211> LENGTH: 23
<212> TYPE: DNA
<213> ORGANISM: artificial
<220> FEATURE:
<223> OTHER INFORMATION: Primer BGH polyA forward

<400> SEQUENCE: 44
tctagttgcc agccatctgt tgt                                               23

<210> SEQ ID NO 45
<211> LENGTH: 18
<212> TYPE: DNA
<213> ORGANISM: artificial
<220> FEATURE:
<223> OTHER INFORMATION: 45 Primer BGH polyA Reverse

<400> SEQUENCE: 45
tgggagtggc accttcca                                                     18

<210> SEQ ID NO 46
<211> LENGTH: 22
<212> TYPE: DNA
<213> ORGANISM: artificial
<220> FEATURE:
<223> OTHER INFORMATION: Primer codon-optimized hGAA forward

<400> SEQUENCE: 46
agatacgccg gacattggac tg                                                22

<210> SEQ ID NO 47
<211> LENGTH: 20
<212> TYPE: DNA
<213> ORGANISM: artificial
<220> FEATURE:
<223> OTHER INFORMATION: Primer codon-optimized hGAA reverse

<400> SEQUENCE: 47
gcacgcccag cagattgaac                                                   20

<210> SEQ ID NO 48
<211> LENGTH: 16
<212> TYPE: PRT
<213> ORGANISM: artificial
<220> FEATURE:
<223> OTHER INFORMATION: linker

<400> SEQUENCE: 48

Gly Gly Gly Gly Ser Leu Val Pro Arg Gly Ser Gly Gly Gly Gly Ser
1               5                   10                  15

<210> SEQ ID NO 49
<211> LENGTH: 6
<212> TYPE: PRT
<213> ORGANISM: artificial
<220> FEATURE:
<223> OTHER INFORMATION: linker

<400> SEQUENCE: 49

Gly Ser Gly Ser Gly Ser
1               5

<210> SEQ ID NO 50
<211> LENGTH: 15
<212> TYPE: PRT
<213> ORGANISM: artificial
<220> FEATURE:
<223> OTHER INFORMATION: linker
```

<400> SEQUENCE: 50

Gly Gly Gly Gly Ser Leu Val Pro Arg Gly Ser Gly Gly Gly Gly
1               5                   10                  15

<210> SEQ ID NO 51
<211> LENGTH: 11
<212> TYPE: PRT
<213> ORGANISM: artificial
<220> FEATURE:
<223> OTHER INFORMATION: linker

<400> SEQUENCE: 51

Gly Gly Ser Gly Gly His Met Gly Ser Gly Gly
1               5                   10

<210> SEQ ID NO 52
<211> LENGTH: 11
<212> TYPE: PRT
<213> ORGANISM: artificial
<220> FEATURE:
<223> OTHER INFORMATION: linker

<400> SEQUENCE: 52

Gly Gly Ser Gly Gly Ser Gly Gly Ser Gly Gly
1               5                   10

<210> SEQ ID NO 53
<211> LENGTH: 5
<212> TYPE: PRT
<213> ORGANISM: artificial
<220> FEATURE:
<223> OTHER INFORMATION: linker

<400> SEQUENCE: 53

Gly Gly Ser Gly Gly
1               5

<210> SEQ ID NO 54
<211> LENGTH: 8
<212> TYPE: PRT
<213> ORGANISM: artificial
<220> FEATURE:
<223> OTHER INFORMATION: linker

<400> SEQUENCE: 54

Gly Gly Ser Gly Gly Gly Gly Gly
1               5

<210> SEQ ID NO 55
<211> LENGTH: 8
<212> TYPE: PRT
<213> ORGANISM: artificial
<220> FEATURE:
<223> OTHER INFORMATION: linker

<400> SEQUENCE: 55

Gly Ser Gly Ser Gly Ser Gly Ser
1               5

<210> SEQ ID NO 56
<211> LENGTH: 18
<212> TYPE: PRT
<213> ORGANISM: artificial
<220> FEATURE:
<223> OTHER INFORMATION: linker -continued

```
<400> SEQUENCE: 56

Gly Gly Gly Ser Glu Gly Gly Gly Ser Glu Gly Gly Gly Ser Glu Gly
1               5                   10                  15

Gly Gly

<210> SEQ ID NO 57
<211> LENGTH: 7
<212> TYPE: PRT
<213> ORGANISM: artificial
<220> FEATURE:
<223> OTHER INFORMATION: linker

<400> SEQUENCE: 57

Ala Ala Gly Ala Ala Thr Ala
1               5

<210> SEQ ID NO 58
<211> LENGTH: 5
<212> TYPE: PRT
<213> ORGANISM: artificial
<220> FEATURE:
<223> OTHER INFORMATION: linker

<400> SEQUENCE: 58

Gly Gly Gly Gly Gly
1               5

<210> SEQ ID NO 59
<211> LENGTH: 5
<212> TYPE: PRT
<213> ORGANISM: artificial
<220> FEATURE:
<223> OTHER INFORMATION: linker

<400> SEQUENCE: 59

Gly Gly Ser Ser Gly
1               5

<210> SEQ ID NO 60
<211> LENGTH: 11
<212> TYPE: PRT
<213> ORGANISM: artificial
<220> FEATURE:
<223> OTHER INFORMATION: linker

<400> SEQUENCE: 60

Gly Ser Gly Gly Gly Thr Gly Gly Gly Ser Gly
1               5                   10

<210> SEQ ID NO 61
<211> LENGTH: 12
<212> TYPE: PRT
<213> ORGANISM: artificial
<220> FEATURE:
<223> OTHER INFORMATION: linker

<400> SEQUENCE: 61

Gly Ser Gly Ser Gly Ser Gly Ser Gly Gly Ser Gly
1               5                   10

<210> SEQ ID NO 62
<211> LENGTH: 14
<212> TYPE: PRT
<213> ORGANISM: artificial
<220> FEATURE:
<223> OTHER INFORMATION: linker
```

<400> SEQUENCE: 62

Gly Ser Gly Gly Ser Gly Gly Ser Gly Gly Ser Gly Gly Ser
1               5                   10

<210> SEQ ID NO 63
<211> LENGTH: 14
<212> TYPE: PRT
<213> ORGANISM: artificial
<220> FEATURE:
<223> OTHER INFORMATION: linker

<400> SEQUENCE: 63

Gly Ser Gly Gly Ser Gly Ser Gly Gly Ser Gly Gly Ser Gly
1               5                   10

<210> SEQ ID NO 64
<211> LENGTH: 2
<212> TYPE: PRT
<213> ORGANISM: artificial
<220> FEATURE:
<223> OTHER INFORMATION: linker

<400> SEQUENCE: 64

Gly Thr
1

<210> SEQ ID NO 65
<211> LENGTH: 3
<212> TYPE: PRT
<213> ORGANISM: artificial
<220> FEATURE:
<223> OTHER INFORMATION: linker

<400> SEQUENCE: 65

Gly Ala Pro
1

<210> SEQ ID NO 66
<211> LENGTH: 917
<212> TYPE: PRT
<213> ORGANISM: artificial
<220> FEATURE:
<223> OTHER INFORMATION: delta8-GAA

<400> SEQUENCE: 66

Leu Leu Val Pro Arg Glu Leu Ser Gly Ser Ser Pro Val Leu Glu Glu
1               5                   10                  15

Thr His Pro Ala His Gln Gln Gly Ala Ser Arg Pro Gly Pro Arg Asp
                20                  25                  30

Ala Gln Ala His Pro Gly Arg Pro Arg Ala Val Pro Thr Gln Cys Asp
        35                  40                  45

Val Pro Pro Asn Ser Arg Phe Asp Cys Ala Pro Asp Lys Ala Ile Thr
    50                  55                  60

Gln Glu Gln Cys Glu Ala Arg Gly Cys Cys Tyr Ile Pro Ala Lys Gln
65                  70                  75                  80

Gly Leu Gln Gly Ala Gln Met Gly Gln Pro Trp Cys Phe Phe Pro Pro
                85                  90                  95

Ser Tyr Pro Ser Tyr Lys Leu Glu Asn Leu Ser Ser Ser Glu Met Gly
            100                 105                 110

Tyr Thr Ala Thr Leu Thr Arg Thr Thr Pro Thr Phe Phe Pro Lys Asp
        115                 120                 125

-continued

```
Ile Leu Thr Leu Arg Leu Asp Val Met Met Glu Thr Glu Asn Arg Leu
    130                 135                 140

His Phe Thr Ile Lys Asp Pro Ala Asn Arg Arg Tyr Glu Val Pro Leu
145                 150                 155                 160

Glu Thr Pro His Val His Ser Arg Ala Pro Ser Pro Leu Tyr Ser Val
                165                 170                 175

Glu Phe Ser Glu Glu Pro Phe Gly Val Ile Val Arg Arg Gln Leu Asp
            180                 185                 190

Gly Arg Val Leu Leu Asn Thr Thr Val Ala Pro Leu Phe Phe Ala Asp
            195                 200                 205

Gln Phe Leu Gln Leu Ser Thr Ser Leu Pro Ser Gln Tyr Ile Thr Gly
    210                 215                 220

Leu Ala Glu His Leu Ser Pro Leu Met Leu Ser Thr Ser Trp Thr Arg
225                 230                 235                 240

Ile Thr Leu Trp Asn Arg Asp Leu Ala Pro Thr Pro Gly Ala Asn Leu
                245                 250                 255

Tyr Gly Ser His Pro Phe Tyr Leu Ala Leu Glu Asp Gly Gly Ser Ala
            260                 265                 270

His Gly Val Phe Leu Leu Asn Ser Asn Ala Met Asp Val Val Leu Gln
            275                 280                 285

Pro Ser Pro Ala Leu Ser Trp Arg Ser Thr Gly Gly Ile Leu Asp Val
    290                 295                 300

Tyr Ile Phe Leu Gly Pro Glu Pro Lys Ser Val Val Gln Gln Tyr Leu
305                 310                 315                 320

Asp Val Val Gly Tyr Pro Phe Met Pro Pro Tyr Trp Gly Leu Gly Phe
            325                 330                 335

His Leu Cys Arg Trp Gly Tyr Ser Ser Thr Ala Ile Thr Arg Gln Val
            340                 345                 350

Val Glu Asn Met Thr Arg Ala His Phe Pro Leu Asp Val Gln Trp Asn
            355                 360                 365

Asp Leu Asp Tyr Met Asp Ser Arg Arg Asp Phe Thr Phe Asn Lys Asp
    370                 375                 380

Gly Phe Arg Asp Phe Pro Ala Met Val Gln Glu Leu His Gln Gly Gly
385                 390                 395                 400

Arg Arg Tyr Met Met Ile Val Asp Pro Ala Ile Ser Ser Ser Gly Pro
            405                 410                 415

Ala Gly Ser Tyr Arg Pro Tyr Asp Glu Gly Leu Arg Arg Gly Val Phe
            420                 425                 430

Ile Thr Asn Glu Thr Gly Gln Pro Leu Ile Gly Lys Val Trp Pro Gly
            435                 440                 445

Ser Thr Ala Phe Pro Asp Phe Thr Asn Pro Thr Ala Leu Ala Trp Trp
    450                 455                 460

Glu Asp Met Val Ala Glu Phe His Asp Gln Val Pro Phe Asp Gly Met
465                 470                 475                 480

Trp Ile Asp Met Asn Glu Pro Ser Asn Phe Ile Arg Gly Ser Glu Asp
                485                 490                 495

Gly Cys Pro Asn Asn Glu Leu Glu Asn Pro Pro Tyr Val Pro Gly Val
            500                 505                 510

Val Gly Gly Thr Leu Gln Ala Ala Thr Ile Cys Ala Ser Ser His Gln
            515                 520                 525

Phe Leu Ser Thr His Tyr Asn Leu His Asn Leu Tyr Gly Leu Thr Glu
    530                 535                 540

Ala Ile Ala Ser His Arg Ala Leu Val Lys Ala Arg Gly Thr Arg Pro
```

```
545                550                555                560

Phe Val Ile Ser Arg Ser Thr Phe Ala Gly His Gly Arg Tyr Ala Gly
             565                570                575

His Trp Thr Gly Asp Val Trp Ser Ser Trp Glu Gln Leu Ala Ser Ser
             580                585                590

Val Pro Glu Ile Leu Gln Phe Asn Leu Leu Gly Val Pro Leu Val Gly
         595                600                605

Ala Asp Val Cys Gly Phe Leu Gly Asn Thr Ser Glu Glu Leu Cys Val
         610                615                620

Arg Trp Thr Gln Leu Gly Ala Phe Tyr Pro Phe Met Arg Asn His Asn
     625                630                635                640

Ser Leu Leu Ser Leu Pro Gln Glu Pro Tyr Ser Phe Ser Glu Pro Ala
                 645                650                655

Gln Gln Ala Met Arg Lys Ala Leu Thr Leu Arg Tyr Ala Leu Leu Pro
             660                665                670

His Leu Tyr Thr Leu Phe His Gln Ala His Val Ala Gly Glu Thr Val
             675                680                685

Ala Arg Pro Leu Phe Leu Glu Phe Pro Lys Asp Ser Ser Thr Trp Thr
     690                695                700

Val Asp His Gln Leu Leu Trp Gly Glu Ala Leu Leu Ile Thr Pro Val
705                710                715                720

Leu Gln Ala Gly Lys Ala Glu Val Thr Gly Tyr Phe Pro Leu Gly Thr
                 725                730                735

Trp Tyr Asp Leu Gln Thr Val Pro Val Glu Ala Leu Gly Ser Leu Pro
             740                745                750

Pro Pro Pro Ala Ala Pro Arg Glu Pro Ala Ile His Ser Glu Gly Gln
             755                760                765

Trp Val Thr Leu Pro Ala Pro Leu Asp Thr Ile Asn Val His Leu Arg
     770                775                780

Ala Gly Tyr Ile Ile Pro Leu Gln Gly Pro Gly Leu Thr Thr Thr Glu
785                790                795                800

Ser Arg Gln Gln Pro Met Ala Leu Ala Val Ala Leu Thr Lys Gly Gly
                 805                810                815

Glu Ala Arg Gly Glu Leu Phe Trp Asp Asp Gly Glu Ser Leu Glu Val
             820                825                830

Leu Glu Arg Gly Ala Tyr Thr Gln Val Ile Phe Leu Ala Arg Asn Asn
             835                840                845

Thr Ile Val Asn Glu Leu Val Arg Val Thr Ser Glu Gly Ala Gly Leu
     850                855                860

Gln Leu Gln Lys Val Thr Val Leu Gly Val Ala Thr Ala Pro Gln Gln
865                870                875                880

Val Leu Ser Asn Gly Val Pro Val Ser Asn Phe Thr Tyr Ser Pro Asp
                 885                890                895

Thr Lys Val Leu Asp Ile Cys Val Ser Leu Leu Met Gly Glu Gln Phe
             900                905                910

Leu Val Ser Trp Cys
             915
```

<210> SEQ ID NO 67
<211> LENGTH: 896
<212> TYPE: PRT
<213> ORGANISM: artificial
<220> FEATURE:
<223> OTHER INFORMATION: delta29-GAA -continued

```
<400> SEQUENCE: 67

Gln Gln Gly Ala Ser Arg Pro Gly Pro Arg Asp Ala Gln Ala His Pro
1               5                   10                  15

Gly Arg Pro Arg Ala Val Pro Thr Gln Cys Asp Val Pro Pro Asn Ser
            20                  25                  30

Arg Phe Asp Cys Ala Pro Asp Lys Ala Ile Thr Gln Glu Gln Cys Glu
        35                  40                  45

Ala Arg Gly Cys Cys Tyr Ile Pro Ala Lys Gln Gly Leu Gln Gly Ala
    50                  55                  60

Gln Met Gly Gln Pro Trp Cys Phe Phe Pro Pro Ser Tyr Pro Ser Tyr
65                  70                  75                  80

Lys Leu Glu Asn Leu Ser Ser Ser Glu Met Gly Tyr Thr Ala Thr Leu
                85                  90                  95

Thr Arg Thr Thr Pro Thr Phe Phe Pro Lys Asp Ile Leu Thr Leu Arg
            100                 105                 110

Leu Asp Val Met Met Glu Thr Glu Asn Arg Leu His Phe Thr Ile Lys
        115                 120                 125

Asp Pro Ala Asn Arg Arg Tyr Glu Val Pro Leu Glu Thr Pro His Val
    130                 135                 140

His Ser Arg Ala Pro Ser Pro Leu Tyr Ser Val Glu Phe Ser Glu Glu
145                 150                 155                 160

Pro Phe Gly Val Ile Val Arg Arg Gln Leu Asp Gly Arg Val Leu Leu
                165                 170                 175

Asn Thr Thr Val Ala Pro Leu Phe Phe Ala Asp Gln Phe Leu Gln Leu
            180                 185                 190

Ser Thr Ser Leu Pro Ser Gln Tyr Ile Thr Gly Leu Ala Glu His Leu
        195                 200                 205

Ser Pro Leu Met Leu Ser Thr Ser Trp Thr Arg Ile Thr Leu Trp Asn
    210                 215                 220

Arg Asp Leu Ala Pro Thr Pro Gly Ala Asn Leu Tyr Gly Ser His Pro
225                 230                 235                 240

Phe Tyr Leu Ala Leu Glu Asp Gly Gly Ser Ala His Gly Val Phe Leu
                245                 250                 255

Leu Asn Ser Asn Ala Met Asp Val Val Leu Gln Pro Ser Pro Ala Leu
            260                 265                 270

Ser Trp Arg Ser Thr Gly Gly Ile Leu Asp Val Tyr Ile Phe Leu Gly
        275                 280                 285

Pro Glu Pro Lys Ser Val Val Gln Gln Tyr Leu Asp Val Val Gly Tyr
    290                 295                 300

Pro Phe Met Pro Pro Tyr Trp Gly Leu Gly Phe His Leu Cys Arg Trp
305                 310                 315                 320

Gly Tyr Ser Ser Thr Ala Ile Thr Arg Gln Val Val Glu Asn Met Thr
                325                 330                 335

Arg Ala His Phe Pro Leu Asp Val Gln Trp Asn Asp Leu Asp Tyr Met
            340                 345                 350

Asp Ser Arg Arg Asp Phe Thr Phe Asn Lys Asp Gly Phe Arg Asp Phe
        355                 360                 365

Pro Ala Met Val Gln Glu Leu His Gln Gly Gly Arg Arg Tyr Met Met
    370                 375                 380

Ile Val Asp Pro Ala Ile Ser Ser Ser Gly Pro Ala Gly Ser Tyr Arg
385                 390                 395                 400

Pro Tyr Asp Glu Gly Leu Arg Arg Gly Val Phe Ile Thr Asn Glu Thr
                405                 410                 415
```

-continued

```
Gly Gln Pro Leu Ile Gly Lys Val Trp Pro Gly Ser Thr Ala Phe Pro
        420                 425                 430

Asp Phe Thr Asn Pro Thr Ala Leu Ala Trp Trp Glu Asp Met Val Ala
        435                 440                 445

Glu Phe His Asp Gln Val Pro Phe Asp Gly Met Trp Ile Asp Met Asn
        450                 455                 460

Glu Pro Ser Asn Phe Ile Arg Gly Ser Glu Asp Gly Cys Pro Asn Asn
465                 470                 475                 480

Glu Leu Glu Asn Pro Pro Tyr Val Pro Gly Val Val Gly Gly Thr Leu
                485                 490                 495

Gln Ala Ala Thr Ile Cys Ala Ser Ser His Gln Phe Leu Ser Thr His
            500                 505                 510

Tyr Asn Leu His Asn Leu Tyr Gly Leu Thr Glu Ala Ile Ala Ser His
        515                 520                 525

Arg Ala Leu Val Lys Ala Arg Gly Thr Arg Pro Phe Val Ile Ser Arg
        530                 535                 540

Ser Thr Phe Ala Gly His Gly Arg Tyr Ala Gly His Trp Thr Gly Asp
545                 550                 555                 560

Val Trp Ser Ser Trp Glu Gln Leu Ala Ser Ser Val Pro Glu Ile Leu
                565                 570                 575

Gln Phe Asn Leu Leu Gly Val Pro Leu Val Gly Ala Asp Val Cys Gly
            580                 585                 590

Phe Leu Gly Asn Thr Ser Glu Glu Leu Cys Val Arg Trp Thr Gln Leu
        595                 600                 605

Gly Ala Phe Tyr Pro Phe Met Arg Asn His Asn Ser Leu Leu Ser Leu
        610                 615                 620

Pro Gln Glu Pro Tyr Ser Phe Ser Glu Pro Ala Gln Gln Ala Met Arg
625                 630                 635                 640

Lys Ala Leu Thr Leu Arg Tyr Ala Leu Leu Pro His Leu Tyr Thr Leu
                645                 650                 655

Phe His Gln Ala His Val Ala Gly Glu Thr Val Ala Arg Pro Leu Phe
            660                 665                 670

Leu Glu Phe Pro Lys Asp Ser Ser Thr Trp Thr Val Asp His Gln Leu
        675                 680                 685

Leu Trp Gly Glu Ala Leu Leu Ile Thr Pro Val Leu Gln Ala Gly Lys
        690                 695                 700

Ala Glu Val Thr Gly Tyr Phe Pro Leu Gly Thr Trp Tyr Asp Leu Gln
705                 710                 715                 720

Thr Val Pro Val Glu Ala Leu Gly Ser Leu Pro Pro Pro Ala Ala
                725                 730                 735

Pro Arg Glu Pro Ala Ile His Ser Glu Gly Gln Trp Val Thr Leu Pro
                740                 745                 750

Ala Pro Leu Asp Thr Ile Asn Val His Leu Arg Ala Gly Tyr Ile Ile
        755                 760                 765

Pro Leu Gln Gly Pro Gly Leu Thr Thr Thr Glu Ser Arg Gln Gln Pro
        770                 775                 780

Met Ala Leu Ala Val Ala Leu Thr Lys Gly Gly Glu Ala Arg Gly Glu
785                 790                 795                 800

Leu Phe Trp Asp Asp Gly Glu Ser Leu Glu Val Leu Glu Arg Gly Ala
                805                 810                 815

Tyr Thr Gln Val Ile Phe Leu Ala Arg Asn Asn Thr Ile Val Asn Glu
        820                 825                 830
```

```
Leu Val Arg Val Thr Ser Glu Gly Ala Gly Leu Gln Leu Gln Lys Val
        835             840             845

Thr Val Leu Gly Val Ala Thr Ala Pro Gln Gln Val Leu Ser Asn Gly
    850             855             860

Val Pro Val Ser Asn Phe Thr Tyr Ser Pro Asp Thr Lys Val Leu Asp
865             870             875             880

Ile Cys Val Ser Leu Leu Met Gly Glu Gln Phe Leu Val Ser Trp Cys
        885             890             895

<210> SEQ ID NO 68
<211> LENGTH: 882
<212> TYPE: PRT
<213> ORGANISM: artificial
<220> FEATURE:
<223> OTHER INFORMATION: delta43-GAA

<400> SEQUENCE: 68

His Pro Gly Arg Pro Arg Ala Val Pro Thr Gln Cys Asp Val Pro Pro
1               5               10              15

Asn Ser Arg Phe Asp Cys Ala Pro Asp Lys Ala Ile Thr Gln Glu Gln
                20              25              30

Cys Glu Ala Arg Gly Cys Cys Tyr Ile Pro Ala Lys Gln Gly Leu Gln
        35              40              45

Gly Ala Gln Met Gly Gln Pro Trp Cys Phe Phe Pro Pro Ser Tyr Pro
    50              55              60

Ser Tyr Lys Leu Glu Asn Leu Ser Ser Ser Glu Met Gly Tyr Thr Ala
65              70              75              80

Thr Leu Thr Arg Thr Thr Pro Thr Phe Phe Pro Lys Asp Ile Leu Thr
                85              90              95

Leu Arg Leu Asp Val Met Met Glu Thr Glu Asn Arg Leu His Phe Thr
            100             105             110

Ile Lys Asp Pro Ala Asn Arg Arg Tyr Glu Val Pro Leu Glu Thr Pro
        115             120             125

His Val His Ser Arg Ala Pro Ser Pro Leu Tyr Ser Val Glu Phe Ser
    130             135             140

Glu Glu Pro Phe Gly Val Ile Val Arg Arg Gln Leu Asp Gly Arg Val
145             150             155             160

Leu Leu Asn Thr Thr Val Ala Pro Leu Phe Phe Ala Asp Gln Phe Leu
                165             170             175

Gln Leu Ser Thr Ser Leu Pro Ser Gln Tyr Ile Thr Gly Leu Ala Glu
            180             185             190

His Leu Ser Pro Leu Met Leu Ser Thr Ser Trp Thr Arg Ile Thr Leu
        195             200             205

Trp Asn Arg Asp Leu Ala Pro Thr Pro Gly Ala Asn Leu Tyr Gly Ser
    210             215             220

His Pro Phe Tyr Leu Ala Leu Glu Asp Gly Gly Ser Ala His Gly Val
225             230             235             240

Phe Leu Leu Asn Ser Asn Ala Met Asp Val Val Leu Gln Pro Ser Pro
                245             250             255

Ala Leu Ser Trp Arg Ser Thr Gly Gly Ile Leu Asp Val Tyr Ile Phe
            260             265             270

Leu Gly Pro Glu Pro Lys Ser Val Val Gln Gln Tyr Leu Asp Val Val
        275             280             285

Gly Tyr Pro Phe Met Pro Pro Tyr Trp Gly Leu Gly Phe His Leu Cys
    290             295             300
```

-continued

```
Arg Trp Gly Tyr Ser Ser Thr Ala Ile Thr Arg Gln Val Val Glu Asn
305             310             315             320

Met Thr Arg Ala His Phe Pro Leu Asp Val Gln Trp Asn Asp Leu Asp
            325             330             335

Tyr Met Asp Ser Arg Arg Asp Phe Thr Phe Asn Lys Asp Gly Phe Arg
            340             345             350

Asp Phe Pro Ala Met Val Gln Glu Leu His Gln Gly Gly Arg Arg Tyr
            355             360             365

Met Met Ile Val Asp Pro Ala Ile Ser Ser Ser Gly Pro Ala Gly Ser
    370             375             380

Tyr Arg Pro Tyr Asp Glu Gly Leu Arg Arg Gly Val Phe Ile Thr Asn
385             390             395             400

Glu Thr Gly Gln Pro Leu Ile Gly Lys Val Trp Pro Gly Ser Thr Ala
            405             410             415

Phe Pro Asp Phe Thr Asn Pro Thr Ala Leu Ala Trp Trp Glu Asp Met
            420             425             430

Val Ala Glu Phe His Asp Gln Val Pro Phe Asp Gly Met Trp Ile Asp
            435             440             445

Met Asn Glu Pro Ser Asn Phe Ile Arg Gly Ser Glu Asp Gly Cys Pro
    450             455             460

Asn Asn Glu Leu Glu Asn Pro Pro Tyr Val Pro Gly Val Val Gly Gly
465             470             475             480

Thr Leu Gln Ala Ala Thr Ile Cys Ala Ser Ser His Gln Phe Leu Ser
            485             490             495

Thr His Tyr Asn Leu His Asn Leu Tyr Gly Leu Thr Glu Ala Ile Ala
            500             505             510

Ser His Arg Ala Leu Val Lys Ala Arg Gly Thr Arg Pro Phe Val Ile
            515             520             525

Ser Arg Ser Thr Phe Ala Gly His Gly Arg Tyr Ala Gly His Trp Thr
    530             535             540

Gly Asp Val Trp Ser Ser Trp Glu Gln Leu Ala Ser Ser Val Pro Glu
545             550             555             560

Ile Leu Gln Phe Asn Leu Leu Gly Val Pro Leu Val Gly Ala Asp Val
            565             570             575

Cys Gly Phe Leu Gly Asn Thr Ser Glu Glu Leu Cys Val Arg Trp Thr
            580             585             590

Gln Leu Gly Ala Phe Tyr Pro Phe Met Arg Asn His Asn Ser Leu Leu
            595             600             605

Ser Leu Pro Gln Glu Pro Tyr Ser Phe Ser Glu Pro Ala Gln Gln Ala
    610             615             620

Met Arg Lys Ala Leu Thr Leu Arg Tyr Ala Leu Leu Pro His Leu Tyr
625             630             635             640

Thr Leu Phe His Gln Ala His Val Ala Gly Glu Thr Val Ala Arg Pro
            645             650             655

Leu Phe Leu Glu Phe Pro Lys Asp Ser Ser Thr Trp Thr Val Asp His
            660             665             670

Gln Leu Leu Trp Gly Glu Ala Leu Leu Ile Thr Pro Val Leu Gln Ala
            675             680             685

Gly Lys Ala Glu Val Thr Gly Tyr Phe Pro Leu Gly Thr Trp Tyr Asp
    690             695             700

Leu Gln Thr Val Pro Val Glu Ala Leu Gly Ser Leu Pro Pro Pro Pro
705             710             715             720

Ala Ala Pro Arg Glu Pro Ala Ile His Ser Glu Gly Gln Trp Val Thr
```

-continued

```
                725             730             735
Leu Pro Ala Pro Leu Asp Thr Ile Asn Val His Leu Arg Ala Gly Tyr
            740             745             750

Ile Ile Pro Leu Gln Gly Pro Gly Leu Thr Thr Thr Glu Ser Arg Gln
            755             760             765

Gln Pro Met Ala Leu Ala Val Ala Leu Thr Lys Gly Gly Glu Ala Arg
            770             775             780

Gly Glu Leu Phe Trp Asp Asp Gly Glu Ser Leu Glu Val Leu Glu Arg
        785             790             795             800

Gly Ala Tyr Thr Gln Val Ile Phe Leu Ala Arg Asn Asn Thr Ile Val
            805             810             815

Asn Glu Leu Val Arg Val Thr Ser Glu Gly Ala Gly Leu Gln Leu Gln
            820             825             830

Lys Val Thr Val Leu Gly Val Ala Thr Ala Pro Gln Gln Val Leu Ser
            835             840             845

Asn Gly Val Pro Val Ser Asn Phe Thr Tyr Ser Pro Asp Thr Lys Val
        850             855             860

Leu Asp Ile Cys Val Ser Leu Leu Met Gly Glu Gln Phe Leu Val Ser
865             870             875             880

Trp Cys

<210> SEQ ID NO 69
<211> LENGTH: 878
<212> TYPE: PRT
<213> ORGANISM: artificial
<220> FEATURE:
<223> OTHER INFORMATION: delta47-GAA

<400> SEQUENCE: 69

Pro Arg Ala Val Pro Thr Gln Cys Asp Val Pro Pro Asn Ser Arg Phe
1               5               10              15

Asp Cys Ala Pro Asp Lys Ala Ile Thr Gln Glu Gln Cys Glu Ala Arg
            20              25              30

Gly Cys Cys Tyr Ile Pro Ala Lys Gln Gly Leu Gln Gly Ala Gln Met
            35              40              45

Gly Gln Pro Trp Cys Phe Phe Pro Pro Ser Tyr Pro Ser Tyr Lys Leu
        50              55              60

Glu Asn Leu Ser Ser Ser Glu Met Gly Tyr Thr Ala Thr Leu Thr Arg
65              70              75              80

Thr Thr Pro Thr Phe Phe Pro Lys Asp Ile Leu Thr Leu Arg Leu Asp
            85              90              95

Val Met Met Glu Thr Glu Asn Arg Leu His Phe Thr Ile Lys Asp Pro
            100             105             110

Ala Asn Arg Arg Tyr Glu Val Pro Leu Glu Thr Pro His Val His Ser
            115             120             125

Arg Ala Pro Ser Pro Leu Tyr Ser Val Glu Phe Ser Glu Glu Pro Phe
        130             135             140

Gly Val Ile Val Arg Arg Gln Leu Asp Gly Arg Val Leu Leu Asn Thr
145             150             155             160

Thr Val Ala Pro Leu Phe Phe Ala Asp Gln Phe Leu Gln Leu Ser Thr
            165             170             175

Ser Leu Pro Ser Gln Tyr Ile Thr Gly Leu Ala Glu His Leu Ser Pro
            180             185             190

Leu Met Leu Ser Thr Ser Trp Thr Arg Ile Thr Leu Trp Asn Arg Asp
            195             200             205
```

-continued

```
Leu Ala Pro Thr Pro Gly Ala Asn Leu Tyr Gly Ser His Pro Phe Tyr
    210                 215                 220

Leu Ala Leu Glu Asp Gly Gly Ser Ala His Gly Val Phe Leu Leu Asn
225                 230                 235                 240

Ser Asn Ala Met Asp Val Val Leu Gln Pro Ser Pro Ala Leu Ser Trp
                245                 250                 255

Arg Ser Thr Gly Gly Ile Leu Asp Val Tyr Ile Phe Leu Gly Pro Glu
                260                 265                 270

Pro Lys Ser Val Val Gln Gln Tyr Leu Asp Val Val Gly Tyr Pro Phe
                275                 280                 285

Met Pro Pro Tyr Trp Gly Leu Gly Phe His Leu Cys Arg Trp Gly Tyr
    290                 295                 300

Ser Ser Thr Ala Ile Thr Arg Gln Val Val Glu Asn Met Thr Arg Ala
305                 310                 315                 320

His Phe Pro Leu Asp Val Gln Trp Asn Asp Leu Asp Tyr Met Asp Ser
                325                 330                 335

Arg Arg Asp Phe Thr Phe Asn Lys Asp Gly Phe Arg Asp Phe Pro Ala
                340                 345                 350

Met Val Gln Glu Leu His Gln Gly Gly Arg Arg Tyr Met Met Ile Val
    355                 360                 365

Asp Pro Ala Ile Ser Ser Ser Gly Pro Ala Gly Ser Tyr Arg Pro Tyr
    370                 375                 380

Asp Glu Gly Leu Arg Arg Gly Val Phe Ile Thr Asn Glu Thr Gly Gln
385                 390                 395                 400

Pro Leu Ile Gly Lys Val Trp Pro Gly Ser Thr Ala Phe Pro Asp Phe
                405                 410                 415

Thr Asn Pro Thr Ala Leu Ala Trp Trp Glu Asp Met Val Ala Glu Phe
                420                 425                 430

His Asp Gln Val Pro Phe Asp Gly Met Trp Ile Asp Met Asn Glu Pro
    435                 440                 445

Ser Asn Phe Ile Arg Gly Ser Glu Asp Gly Cys Pro Asn Asn Glu Leu
    450                 455                 460

Glu Asn Pro Pro Tyr Val Pro Gly Val Val Gly Gly Thr Leu Gln Ala
465                 470                 475                 480

Ala Thr Ile Cys Ala Ser Ser His Gln Phe Leu Ser Thr His Tyr Asn
                485                 490                 495

Leu His Asn Leu Tyr Gly Leu Thr Glu Ala Ile Ala Ser His Arg Ala
                500                 505                 510

Leu Val Lys Ala Arg Gly Thr Arg Pro Phe Val Ile Ser Arg Ser Thr
    515                 520                 525

Phe Ala Gly His Gly Arg Tyr Ala Gly His Trp Thr Gly Asp Val Trp
    530                 535                 540

Ser Ser Trp Glu Gln Leu Ala Ser Ser Val Pro Glu Ile Leu Gln Phe
545                 550                 555                 560

Asn Leu Leu Gly Val Pro Leu Val Gly Ala Asp Val Cys Gly Phe Leu
                565                 570                 575

Gly Asn Thr Ser Glu Glu Leu Cys Val Arg Trp Thr Gln Leu Gly Ala
                580                 585                 590

Phe Tyr Pro Phe Met Arg Asn His Asn Ser Leu Leu Ser Leu Pro Gln
    595                 600                 605

Glu Pro Tyr Ser Phe Ser Glu Pro Ala Gln Gln Ala Met Arg Lys Ala
    610                 615                 620
```

```
Leu Thr Leu Arg Tyr Ala Leu Leu Pro His Leu Tyr Thr Leu Phe His
625             630             635             640

Gln Ala His Val Ala Gly Glu Thr Val Ala Arg Pro Leu Phe Leu Glu
                645             650             655

Phe Pro Lys Asp Ser Ser Thr Trp Thr Val Asp His Gln Leu Leu Trp
            660             665             670

Gly Glu Ala Leu Leu Ile Thr Pro Val Leu Gln Ala Gly Lys Ala Glu
            675             680             685

Val Thr Gly Tyr Phe Pro Leu Gly Thr Trp Tyr Asp Leu Gln Thr Val
    690             695             700

Pro Val Glu Ala Leu Gly Ser Leu Pro Pro Pro Pro Ala Ala Pro Arg
705             710             715             720

Glu Pro Ala Ile His Ser Glu Gly Gln Trp Val Thr Leu Pro Ala Pro
            725             730             735

Leu Asp Thr Ile Asn Val His Leu Arg Ala Gly Tyr Ile Ile Pro Leu
            740             745             750

Gln Gly Pro Gly Leu Thr Thr Thr Glu Ser Arg Gln Gln Pro Met Ala
    755             760             765

Leu Ala Val Ala Leu Thr Lys Gly Gly Glu Ala Arg Gly Glu Leu Phe
    770             775             780

Trp Asp Asp Gly Glu Ser Leu Glu Val Leu Glu Arg Gly Ala Tyr Thr
785             790             795             800

Gln Val Ile Phe Leu Ala Arg Asn Asn Thr Ile Val Asn Glu Leu Val
            805             810             815

Arg Val Thr Ser Glu Gly Ala Gly Leu Gln Leu Gln Lys Val Thr Val
            820             825             830

Leu Gly Val Ala Thr Ala Pro Gln Gln Val Leu Ser Asn Gly Val Pro
            835             840             845

Val Ser Asn Phe Thr Tyr Ser Pro Asp Thr Lys Val Leu Asp Ile Cys
    850             855             860

Val Ser Leu Leu Met Gly Glu Gln Phe Leu Val Ser Trp Cys
865             870             875
```

CHIMERIC POLYPEPTIDES AND USES THEREOF

CROSS-REFERENCE TO RELATED APPLICATION

This application is the U.S. national stage application of International Patent Application No. PCT/EP2020/079693, filed Oct. 22, 2020.

REFERENCE TO SEQUENCE LISTING

The Sequence Listing for this application is labeled "Seq-List.txt" which was created on Mar. 12, 2022 and is 163 KB. The entire content of the sequence listing is incorporated herein by reference in its entirety.

Some therapies are based on the administration of a therapeutic polypeptide or on the administration of a gene therapy vector expressing a therapeutic polypeptide. Said polypeptide may be intended to circulate in the bloodstream in order to reach the targeted tissues. In this case, it is desirable to improve the properties of the therapeutic peptide in order to enhance its activity. For example, it may be advantageous to improve the stability of the therapeutic polypeptide in the plasma compartment, or to facilitate the uptake of the circulating polypeptide by the targeted tissues where it is intended to exert its therapeutic activity.

Such circulating polypeptides include the lysosomal enzyme acid alpha-glucosidase (GAA) polypeptide. In particular, it is desirable to improve the activity of the GAA polypeptide administered for therapeutic purposes, in the context of Pompe disease. Pompe disease, also known as glycogen storage disease (GSD) type II and acid maltase deficiency, is an autosomal recessive metabolic myopathy caused by a deficiency of the lysosomal enzyme acid alpha-glucosidase. GAA is an exo-1,4 and 1,6-α-glucosidase that hydrolyzes glycogen to glucose in the lysosome. Deficiency of GAA leads to glycogen accumulation in lysosomes and causes progressive damage to respiratory, cardiac, and skeletal muscle. The disease ranges from a rapidly progressive infantile course that is usually fatal by 1-2 years of age to a more slowly progressive and heterogeneous course that causes significant morbidity and early mortality in children and adults. Hirschhorn R R, The Metabolic and Molecular Bases of Inherited Disease, 3: 3389-3420 (2001, McGraw-Hill); Van der Ploeg and Reuser, Lancet 372: 1342-1351 (2008).

Current human therapy for treating Pompe disease involves administration of recombinant human GAA, otherwise termed enzyme-replacement therapy (ERT). ERT has demonstrated efficacy for severe, infantile GSD II. However the benefit of enzyme therapy is limited by a poor biodistribution of the protein following peripheral vein delivery, lack of uptake from several tissues, and the need for frequent infusions.

As an alternative or adjunct to ERT, the feasibility of gene therapy approaches to treat GSD-II have been investigated (Amalfitano, A., et al. (1999) Proc. Natl. Acad. Sci. USA 96:8861-8866, Ding, E., et al. (2002) Mol. Ther. 5:436-446, Fraites, T. J., et al. (2002) Mol. Ther. 5:571-578, Tsujino, S., et al. (1998) Hum. Gene Ther. 9:1609-1616).

Modified GAA proteins have also been proposed in the past to improve lysosomal storage disease treatment. In particular, application WO2004064750 and Sun et al. 2006, disclose a chimeric GAA polypeptide comprising a signal peptide operably linked to GAA as a way to enhance targeting of the protein to the secretory pathway. In WO2018/046772, WO2018/046775 and WO2018/046774 patent applications, GAA variants were provided to improve current gene replacement therapies for Pompe disease. Said patent applications disclose GAA variants that were shown to be highly secretable and less immunogenic than their wild type counterpart.

Further improvements of GAA are herein described.

SUMMARY OF THE INVENTION

The present invention relates to a nucleic acid molecule encoding a chimeric polypeptide comprising a peptide of interest fused to one or more heterologous moieties, wherein at least one of the heterologous moieties is a ligand of the Sortilin receptor.

In a particular embodiment, the chimeric polypeptide comprises a peptide of interest fused to one heterologous moiety being a ligand of the Sortilin receptor.

In a particular embodiment, the ligand of the Sortilin receptor is selected from:

a Spadin peptide encoded by the nucleotide sequence of SEQ ID NO: 14 or by a nucleotide sequence having at least 85% identity, preferably at least 90% identity, to the nucleotide sequence of SEQ ID NO: 14;

a Neurotensin peptide encoded by the nucleotide sequence of SEQ ID NO: 15 or by a nucleotide sequence having at least 85% identity, preferably at least 90% identity, to the nucleotide sequence of SEQ ID NO: 15; or a fragment of Neurotensin peptide encoded by the nucleotide sequence of SEQ ID NO: 16 or by a nucleotide sequence having at least 85% identity, preferably at least 90% identity, to the nucleotide sequence of SEQ ID NO: 16.

In a particular embodiment, the ligand of the Sortilin receptor is a Spadin peptide encoded by a nucleotide sequence comprising or consisting of SEQ ID NO: 14.

In a particular embodiment, the peptide of interest is a functional GAA polypeptide, which may be encoded by a nucleotide sequence selected in the group consisting of SEQ ID NO: 1-3 or by a nucleotide sequence having at least 85% identity, preferably at least 90% identity, to a nucleotide sequence selected in the group consisting of SEQ ID NO: 1-3.

In a particular embodiment, the peptide of interest is a functional GAA polypeptide corresponding to a truncated form of a GAA. In particular, said functional GAA polypeptide may have 42 consecutive amino acids truncated at its N-terminal end as compared to GAA. In a particular embodiment, the truncated GAA is encoded by the nucleotide sequence of SEQ ID NO:10 or by a nucleotide sequence having at least 85% identity, preferably at least 90% identity, to the nucleotide sequence of SEQ ID NO:10.

In a particular embodiment, the heterologous moiety as described above is fused at the N-terminal end of the peptide of interest.

In a particular embodiment, the nucleic acid molecule of the invention further comprises a signal peptide having an amino acid sequence selected in the group consisting of SEQ ID NO: 18-22, preferably SEQ ID NO:21.

The present invention also relates to a nucleic acid construct comprising the nucleic acid molecule as described above, operably linked to a promoter, wherein said nucleic acid construct may optionally further comprise an intron. In a particular embodiment, the nucleic acid construct may comprise, preferably in this order: a promoter; an intron; the nucleic acid molecule as described above; and a polyadenylation signal.

The present invention also relates to a vector comprising the nucleic acid molecule or the nucleic acid construct of the invention, such as a viral vector, preferably a retroviral vector, such as a lentiviral vector, or an AAV vector. In particular, the vector may be a single-stranded or double-stranded self-complementary AAV vector, preferably an AAV vector with an AAV-derived capsid, such as an AAV1 capsid, AAV2 capsid, variant AAV2 capsid, AAV3 capsid, variant AAV3 capsid, AAV3B capsid, variant AAV3B capsid, AAV4 capsid, AAV5 capsid, AAV6 capsid, variant AAV6 capsid, AAV7 capsid, AAV8 capsid, AAV9 capsid, AAV10 capsid such as AAVcy10 capsid and AAVrh10 capsid, AAVrh74 capsid, AAVdj capsid, AAVAnc80 capsid, AAV-LK03 capsid, AAV2i8 capsid, and porcine AAV capsid, such as AAVpo4 capsid and AAVpo6 capsid or with a chimeric capsid. In a particular embodiment, the AAV vector has an AAV8, AAV9, AAVrh74 or AAV2i8 capsid, in particular an AAV8, AAV9 or AAVrh74 capsid, more particularly an AAV8 capsid.

The invention also relates to an isolated cell transformed with the nucleic acid molecule, the nucleic acid construct or the vector as described above.

In addition, it is herein described a chimeric polypeptide encoded by the nucleic acid molecule of the invention.

The invention further relates to a pharmaceutical composition, comprising, in a pharmaceutically acceptable carrier, the nucleic acid molecule, the nucleic acid construct, the vector, the isolated cell or the chimeric polypeptide as described above.

It is also described the nucleic acid molecule, the nucleic acid construct, the vector, the isolated cell or the chimeric polypeptide as described above. for use as a medicament. In a particular embodiment, the nucleic acid molecule, the nucleic acid construct, the vector, the isolated cell or the chimeric polypeptide as described above are for use in a method for treating a lysosomal storage disease such as a glycogen storage disease (GSD), a mucopolysaccharidosis type I (MPSI), a mucopolysaccharidosis type II (MPSII), a metachromatic leukodystrophy (MLD), or a mucopolysaccharidosis type VI (MPS VI, in particular for treating GSDII (Pompe disease).

LEGENDS TO THE FIGURES

FIG. 1. Schematic representation of expression cassettes encoding chimeric GAA variants of the invention. The heterologous domains (HD) were cloned at the GAA N-terminus. ITR: inverted terminal repeats from AAV2; Promoter: ApoE Enhancer (ApoE) and hepatocyte-specific human alpha 1-antitrypsin promoter (hAAT); intron: optimized human haemoglobin I3-subunit synthetic intron (HBB2.1); signal peptide from the human Chymotrypsinogen (sp7); HD: heterologous domain; GAAco: codon optimized GAA; polyA: human bovine growth hormone polyadenylation sequence; ApoB: apolipoprotein B domain; ApoE: apolipoprotein E domain; Spadin: Spadin peptide; NT1-13: neurotensin amino acid 1-13; NT9-13: neurotensin amino acid 9-13; linker: 3 amino acids linker.

Figure 2:
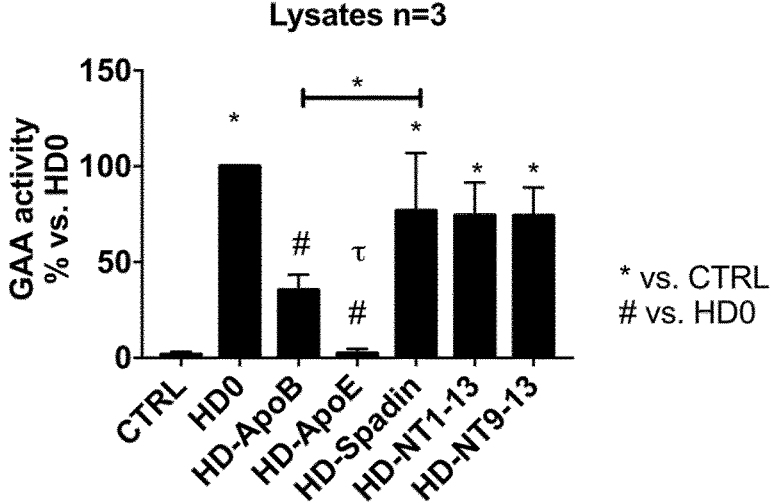

FIG. 2. Expression of chimeric GAA variants of the invention in human hepatocyte cell cultures. Analysis of HuH7 lysates 72 h after transfection with plasmids encoding for the chimeric GAA variants sp7-ApoB-Δ42-GAAco (HD-ApoB), sp7-ApoE-Δ42-GAAco (HD-ApoE), sp7-Spadin-Δ42-GAAco (HD-Spadin), sp7-Neurotensin 1-13-Δ42-GAAco (FID-NT1-13), sp7-Neurotensin 9-13-Δ42-GAAco (HD-NT1-9-13). The GAA variant devoid of heterologous domains sp7-Δ42-GAAco (HD0) was used as comparison. CTRL: control cells transfected with a plasmid encoding for the enhanced green fluorescent protein and used as negative control. Transfection was repeated in 3 independent experiments. For each replicate, GAA data were expressed as relative amount compared to HD0 (HD0=100%). Data are shown as mean±standard deviation of the mean (SD) of 3 independent experiments. Statistical analysis: one-way ANOVA with Tukey's post hoc. *$p < 0.05$.

Figure 3:
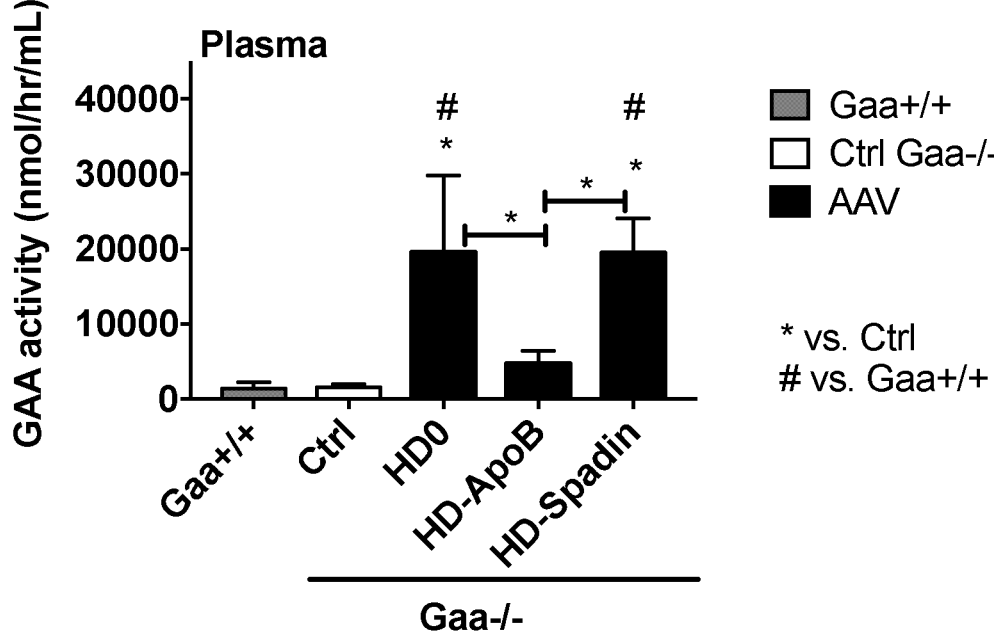

FIG. 3. Activity of GAA variants of the invention in the plasma of Gaa−/− mice following AAV liver gene transfer. Analyses of GAA activity in the plasma of Gaa−/− mice measured 4 months after intravenous administration of AAV8 vectors encoding for the chimeric GAA variants (AAV, n=6 mice/group; vector dose: $5 \times 10^{11}$ vg/kg); mice treated with PBS were used as negative control (Ctrl n=6 mice); HD-ApoB: sp7-ApoB-Δ42-GAAco, HD-Spadin: sp7-Spadin-Δ42-GAAco, HD0: sp7-Δ42-GAAco. Data are shown as mean±SD. Statistical analysis: One-way ANOVA with Tukey's post hoc multiple comparison "All groups vs. all, time point independent". Asterisks (*) and hashtags (#) indicate significant differences as specified in the legend. * $p < 0.05$.

Figure 4:
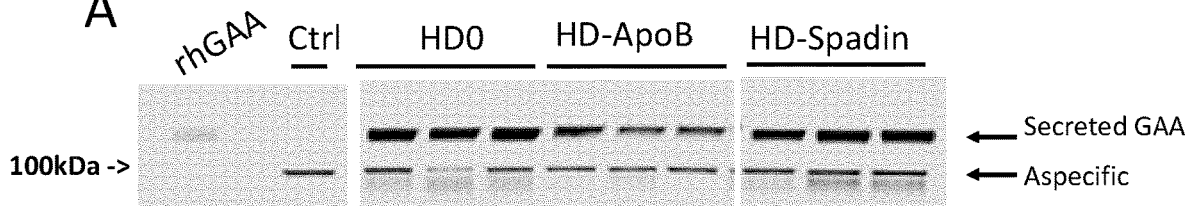
Figure 4:
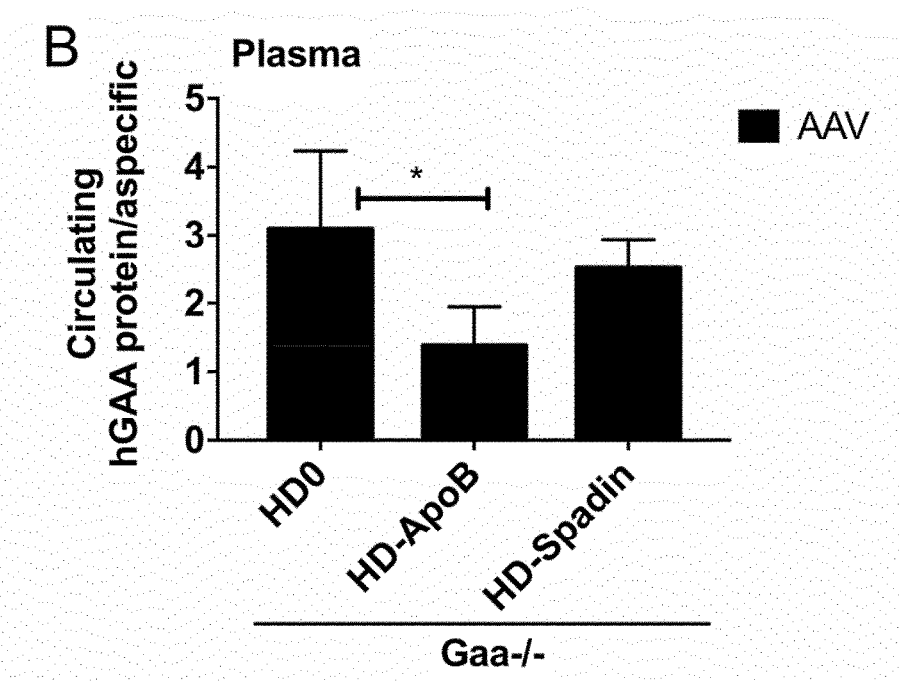

FIG. 4. Secretion of GAA variants of the invention in the plasma of Gaa−/− mice following AAV liver gene transfer. Analyses of GAA secretion in the plasma of Gaa−/− mice measured 4 months after intravenous administration of AAV8 vectors encoding for the chimeric GAA variants (AAV, n=6 mice/cohort; vector dose: $5 \times 10^{11}$ vg/kg); HD-ApoB: sp7-ApoB-Δ42-GAAco, HD-Spadin: sp7-Spadin-Δ42-GAAco, HD0: sp7-Δ42-GAAco. (A) Western blot in plasma with anti-hGAA antibody, recombinant human GAA (rhGAA) was used as positive control; the molecular weight marker is depicted. (B) Quantification of GAA protein bands from Western blot depicted in panels A, the non-specific lower band was used for loading normalization. Data are shown as mean±SD. Statistical analysis: One-way ANOVA with Tukey's post hoc, multiple comparison "All groups vs. all, time point independent", * $p < 0.05$.

Figure 5:
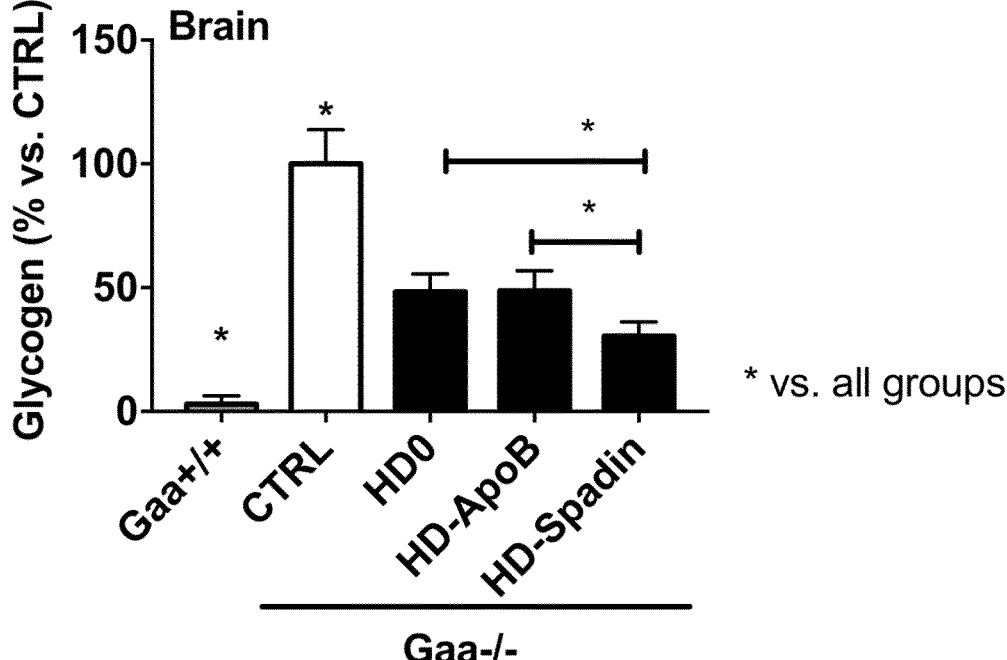

FIG. 5. Analyses of glycogen content in the brain of Gaa−/− mice following AAV liver gene transfer. Analyses of glycogen content in brains of Gaa−/− mice 4 months after treatment with AAV8 vectors encoding for the chimeric GAA variants (AAV, n=6/cohort; dose: $5 \times 10^{11}$ vg/kg); mice treated with PBS were used as negative control (CTRL, n=6); Gaa+/+(n=6) were used as unaffected control. Data are shown as mean±SD. Asterisks (*) and hashtags (#) indicate significant differences versus the groups indicated in the legend; Glycogen content in Brain is depicted. Statistical analysis: one-way ANOVA with Tukey's post hoc, multiple comparison "All groups vs. all". * $p < 0.05$, #$p < 0.05$.

Figure 6:
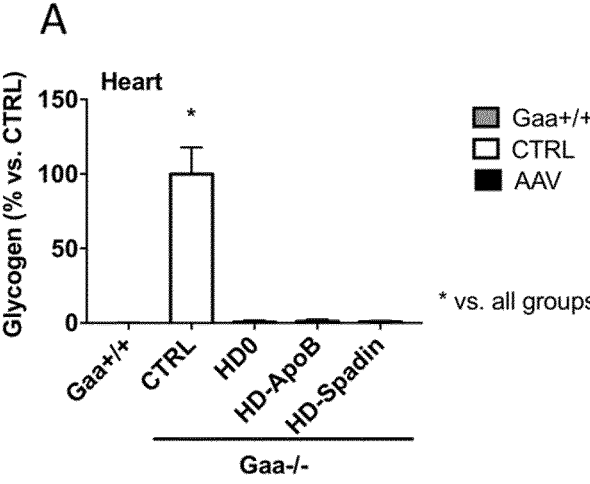
Figure 6:
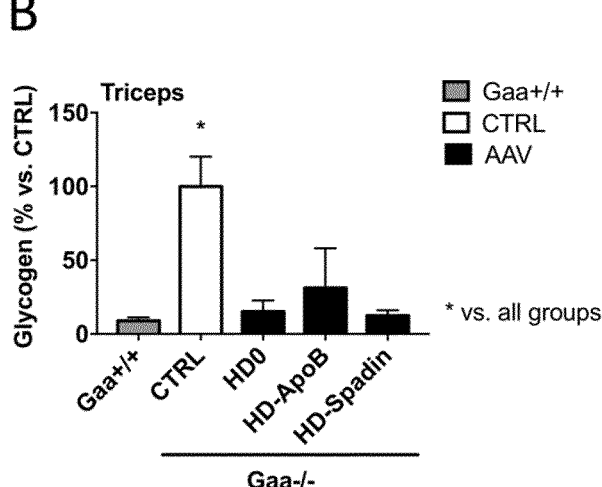
Figure 6:
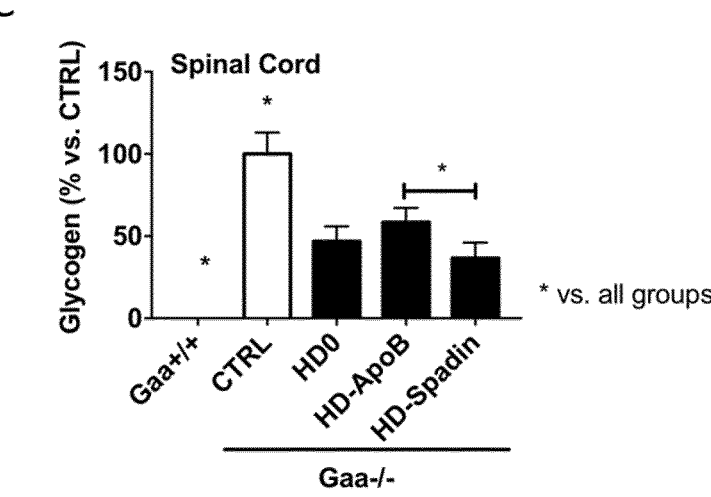

FIG. 6. Analyses of glycogen content in the tissues of Gaa−/− mice following AAV liver gene transfer. Analyses of glycogen content in tissues of Gaa−/− mice 4 months after treatment with AAV8 vectors encoding for the chimeric GAA variants (AAV, n=6/cohort; dose: $5 \times 10^{11}$ vg/kg); mice treated with PBS were used as negative control (CTRL, n=6); Gaa+/+(n=6) were used as unaffected control. Data are shown as mean±SD. Asterisks (*) and hashtags (#) indicate significant differences versus the groups indicated in the legend; Glycogen content in Heart (A), Triceps (B), Spinal cord (C) is depicted. Statistical analysis: one-way ANOVA with Tukey's post hoc, multiple comparison "All groups vs. all". * $p < 0.05$, #$p < 0.05$.

Figure 7:
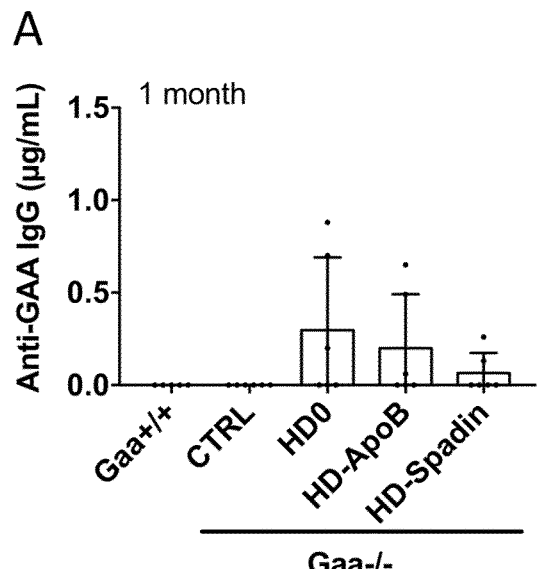
Figure 7:
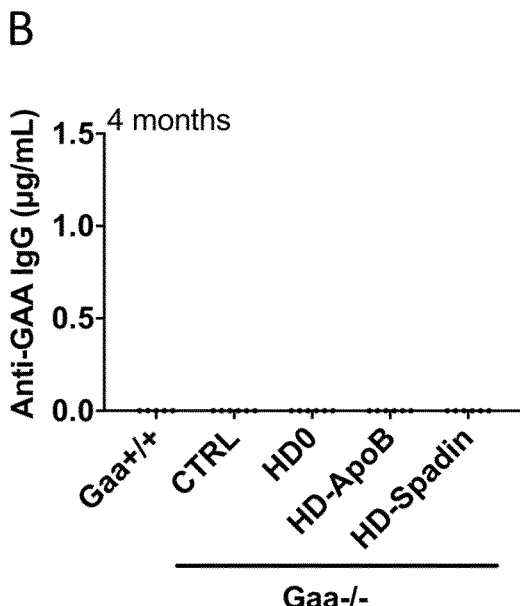

FIG. 7. Analyses of GAA immunogenicity in the plasma of Gaa−/− mice following AAV liver gene transfer Analyses of anti-GAA IgG in the plasma of Gaa−/− mice at 1 and 4 months after administration with AAV8 vectors encoding for the chimeric GAA variants (AAV, n=6/cohort; dose: 5×10$^{11}$ vg/kg); mice treated with PBS were used as negative control (CTRL, n=6); Gaa+/+(n=6) were used as unaffected control. Data are shown as mean±SD. Statistical analysis: one-way ANOVA with Tukey's post hoc, multiple comparison "All groups vs. all".

DETAILED DESCRIPTION OF THE INVENTION

The present inventors have conducted an extensive search of new methods for enhancing the in vivo activity of a peptide of interest by fusing heterologous moieties with the peptide of interest. In particular, the acid α-glucosidase polypeptide was used as a model peptide. As a result, the present inventors have shown that a fusion protein of a GAA with a ligand of the Sortilin receptor, in particular with a Spadin peptide has improved properties including, improved uptake in the central nervous system (CNS) and better activity in tissues such as the brain. Noteworthy, the addition of the ligand to the GAA peptide does not elicit an increased immunogenic response against the chimeric GAA polypeptide.

Thus, the present invention generally relates to a chimeric polypeptide, comprising a peptide of interest fused to one or more heterologous moieties, wherein at least one of the heterologous moieties is a ligand of the Sortilin receptor.

1—Nucleic Acid Molecule

A first aspect of the invention relates to a nucleic acid molecule encoding a chimeric polypeptide comprising a peptide of interest fused to one or more heterologous moieties, wherein at least one of the heterologous moieties is a ligand of the Sortilin receptor.

By "chimeric protein" or "fusion protein" is meant proteins created through the joining of two or more genes that originally encode separate proteins.

The chimeric polypeptide of the invention refers to the fusion of:

a peptide of interest, with one or more "heterologous moieties" derived from a polypeptide different from the peptide of interest.

Peptide of Interest

The peptide of interest may be any peptide, for which an improved activity in vivo is sought. In particular, the peptide of interest is a circulating peptide. By "circulating peptide" is meant any peptide, polypeptide or fragment thereof that is found in the blood circulation. The peptide of interest may be a secreted peptide. By "secreted protein" is meant any peptide, polypeptide or fragment thereof, which is intracellularly processed for secretion into the extracellular environment. In particular, the peptide of interest is a circulating peptide, for which an improved activity and/or stability in plasma is sought, or for which better lysosomal targeting and/or crossing of the blood brain barrier to effectively reach the CNS is sought. The peptide of interest may be any circulating peptide for which an improved uptake and/or activity in targeted tissues is sought. The targeted tissue can be for example the CNS such as the brain or the spinal cord, the muscles such as skeletal muscles, or the liver. In particular, the peptide is a peptide or polypeptide for which an improved uptake and/or activity in the CNS including the brain or the spinal cord is sought, in particular for which an improved uptake and/or activity in the brain is sought. In particular, the peptide of interest may be any peptide that is targeted to the lysosome.

In a particular embodiment, the peptide of interest is a therapeutic peptide, i.e. a peptide that is delivered for a therapeutic purpose, e.g. to treat, prevent, or ameliorate a disease or pathological state. In particular, the therapeutic peptide is administered by infusion of the peptide or by expression using a gene therapy vector.

In a particular embodiment, the peptide of interest is a peptide which is known to be deficient in a lysosomal disorder associated with neurological manifestations.

In a particular embodiment, the peptide of interest is selected from the group consisting of the lysosomal acid α-glucosidase (GAA), the alpha-iduronidase (IDUA), the lysosomal hydrolase iduronate 2-sulfatase (IDS), the arylsulfatase A (ARSA), alpha-galactosidase A (GLA), Glucosylceramidase, β-Galactosidase, β-Hexosaminidase A, β-Hexosaminidase B, β-Galactosyl-ceramidase, Acid sphingomyelinase, Heparan sulphamidase, Acetyl CoA: α-glucosaminide N-acetyltransferase, N-acetylglucosamine-6-sulphatase, β-Glucuronidase, Acid ceramidase, α-Mannosidase, β-Mannosidase, N-acetylgalactosaminidase, α-Neuraminidase, Palmitoyl-protein thioesterase 1, Carboxypeptidase, Multiple sulphatases, N-acetylglucosamine phosphate transferase, Protective protein cathepsin A, neuraminidase, NPC2, GM2 activator protein, LAMP2, NPC1, Sialin, CLN3, and Mucolipin.

In a particular embodiment, the peptide of interest is the lysosomal acid α-glucosidase or "GAA". In this embodiment, the nucleic acid molecule of the invention encodes a chimeric GAA polypeptide comprising:

a functional GAA polypeptide, fused to one or more heterologous moieties, wherein at least one of the heterologous moieties is a ligand of the Sortilin receptor.

Lysosomal acid α-glucosidase or "GAA" (E.C. 3.2. 1.20) (1,4-α-D-glucan glucohydrolase), is an exo-1,4-α-D-glucosidase that hydrolyses both α-1,4 and α-1,6 linkages of oligosaccharides to liberate glucose. A deficiency in GAA results in glycogen storage disease type II (GSDII), also referred to as Pompe disease (although this term formally refers to the infantile onset form of the disease). It catalyzes the complete degradation of glycogen with slowing at branching points. The 28 kb human acid α-glucosidase gene on chromosome 17 encodes a 3.6 kb mRNA which produces a 951 amino acid polypeptide (Hoefsloot et al., (1988) EMBO J. 7: 1697; Martiniuk et al., (1990) DNA and Cell Biology 9: 85). The enzyme receives co-translational N-linked glycosylation in the endoplasmic reticulum. It is synthesized as a 110-kDa precursor form, which matures by extensive glycosylation modification, phosphorylation and by proteolytic processing through an approximately 90-kDa endosomal intermediate into the final lysosomal 76 and 67 kDa forms (Hoefsloot, (1988) EMBO J. 7: 1697; Hoefsloot et al., (1990) Biochem. J. 272: 485; Wisselaar et al., (1993) J. Biol. Chem. 268: 2223; Hermans et al., (1993) Biochem. J. 289: 681).

In patients with GSD II, a deficiency of acid α-glucosidase causes massive accumulation of glycogen in lysosomes, disrupting cellular function (Hirschhorn, R. and Reuser, A. J. (2001), in The Metabolic and Molecular Basis for Inherited Disease, (eds, Scriver, C. R. et al.) pages 3389-3419 (McGraw-Hill, New York). In the most common infantile form, patients exhibit progressive muscle degeneration and cardiomyopathy and die before two years of age. Severe debilitation is present in the juvenile and adult onset forms.

The term "GAA" or "GAA polypeptide", as used herein, encompasses mature (~76 or ~67 kDa) and precursor (e.g., —110 kDa) GAA, in particular the precursor form, as well as modified or mutated by insertion(s), deletion (s) and/or substitution(s)) GAA proteins or fragments thereof that are functional derivatives of GAA, i.e. that retain biological function of GAA (i.e., have at least one biological activity of the native GAA protein, e.g., can hydrolyze glycogen, as defined above) and GAA variants (e.g., GAA II as described by Kunita et al., (1997) Biochemica et Biophysica Acta 1362: 269; GAA polymorphisms and SNPs are described by Hirschhorn, R. and Reuser, A. J. (2001) In The Metabolic and Molecular Basis for Inherited Disease (Scriver, C. R., Beaudet, A. L., Sly, W. S. & Valle, D. Eds.), pp. 3389-3419. McGraw-Hill, New York, see pages 3403-3405). Any GAA coding sequence known in the art may be used, for example, see SEQ ID NO:1; GenBank Accession number NM_00152 and Hoefsloot et al., (1988) EMBO J. 7: 1697 and Van Hove et al., (1996) Proc. Natl. Acad. Sci. USA 93: 65 (human), GenBank Accession number NM_008064 (mouse), and Kunita et al., (1997) Biochemica et Biophysica Acta 1362: 269 (quail).

The nucleic acid molecule encoding a chimeric GAA polypeptide comprises any "functional GAA polypeptide", i.e. it encodes for a GAA protein that, when expressed, has the functionality of wild-type GAA protein. As defined above, the functionality of wild-type GAA is to hydrolyse both α-1,4 and α-1,6 linkages of oligosaccharides and polysaccharides, more particularly of glycogen, to liberate glucose. The functional GAA protein encoded by the nucleic acid molecule may have a hydrolysing activity on glycogen of at least 50%, 60%, 70%, 80%, 90%, 95%, 99%, or at least 100% as compared to the wild-type GAA protein encoded by the nucleic acid sequence of SEQ ID NO:1 to 3, for example as compared to the GAA polypeptide having the amino acid sequence of SEQ ID NO:4. The activity of the functional GAA polypeptide encoded by the nucleic acid molecule may even be of more than 100%, such as of more than 110%, 120%, 130%, 140%, or even more than 150% of the activity of the wild-type GAA protein encoded by the nucleic acid sequence of SEQ ID NO:1 to 3, for example as compared to the GAA polypeptide having the amino acid sequence of SEQ ID NO:4.

A skilled person is readily able to determine whether a nucleic acid molecule expresses a functional GAA protein. For example, one suitable in vitro method involves inserting the nucleic acid into a vector, such as a plasmid or viral vector, transfecting or transducing host cells, such as 293T or HeLa cells, or other cells such as Huh7, with the vector, and assaying for GAA activity. Alternatively, a suitable in vivo method involves transducing a vector containing the nucleic acid into a mouse model of Pompe disease or another glycogen storage disorder and assaying for functional GAA in the plasma of the mouse and presence of GAA in tissues. Suitable methods are described in more details in the experimental part below.

The sequence of the nucleic acid molecule encoding the functional GAA polypeptide preferably has at least 85 percent, more preferably at least 90 percent, and even more preferably at least 92 percent identity, in particular at least 95 percent identity, for example at least 98, 99 or 100 percent identity to the nucleotide sequence of SEQ ID NO: 1 to 3.

The term "identical" and declinations thereof refers to the sequence identity between two nucleic acid molecules or two amino acid molecules. When a position in both of the two compared sequences is occupied by the same base or amino acid, then the molecules are identical at that position. The percent of identity between two sequences is a function of the number of matching positions shared by the two sequences divided by the number of positions compared× 100. For example, if 6 of 10 of the positions in two sequences are matched then the two sequences are 60% identical. Generally, a comparison is made when two sequences are aligned to give maximum identity. Various bioinformatic tools known to the one skilled in the art might be used to align nucleic acid sequences such as BLAST or FASTA.

In a particular embodiment, the functional GAA polypeptide encoded by the nucleic acid molecule as herein described is a functional, truncated form of GAA. By "truncated form" or "truncated GAA", it is meant a GAA polypeptide that comprises one or several consecutive amino acids deleted from the N-terminal part of a parent GAA polypeptide. According to the present invention a "parent GAA polypeptide" is a functional, precursor GAA sequence, but devoid of its signal peptide. For example, with reference to the typical wild-type human GAA polypeptide, a complete wild-type GAA polypeptide (i.e. a precursor form of GAA) is represented in SEQ ID NO: 5 or in SEQ ID NO: 6 and has a signal peptide (corresponding to amino acids 1-27 of SEQ ID NO: 5 or SEQ ID NO: 6), whereas the parent GAA polypeptide serving as basis for the truncated GAA forms of these wild-type human GAA polypeptides are represented in SEQ ID NO: 7 and SEQ ID NO: 8, respectively and have no signal peptide. In this example, the latter, corresponding to amino acids 28-952 of SEQ ID NO: 5 and to amino acids 28-952 of SEQ ID NO: 6, is referred to as a parent GAA polypeptide.

According to the invention, the truncated GAA polypeptide is a functional GAA polypeptide, i.e. it has the functionality of wild-type GAA polypeptide as defined above.

The amino acid sequence of the parent GAA polypeptide or its coding sequence can be derived from any source, including avian and mammalian species. The term "avian" as used herein includes, but is not limited to, chickens, ducks, geese, quail, turkeys and pheasants. The term "mammal" as used herein includes, but is not limited to, humans, simians and other non-human primates, bovines, ovines, caprines, equines, felines, canines, lagomorphs, etc. In embodiments of the invention, the parent GAA polypeptide is a human, mouse or quail, in particular a human, GAA polypeptide.

In addition, the parent GAA polypeptide may be a functional variant of a GAA polypeptide, comprising one or more amino acid modifications such as amino acid insertion, deletion and/or substitution as compared to a known GAA polypeptide. For example, the parent polypeptide may be a functional derivative of a human GAA polypeptide, such as the polypeptide of SEQ ID NO:7 or SEQ ID NO:8, in particular SEQ ID NO:7, having at least 80, 85, 90, 95, 96, 97, 98 or at least 99 percent sequence identity to this human GAA polypeptide. For example, the functional variant of a GAA polypeptide may have between 0 and 50, between 0 and 30, between 0 and 20, between 0 and 15, between 0 and 10, or between 0 and 5 amino acid changes to the parent GAA polypeptide, such as the parent GAA polypeptide shown in SEQ ID NO: 7 or SEQ ID NO:8, in particular SEQ ID NO:7. In particular, the parent GAA polypeptide may consist of the human GAA polypeptide having the amino acid sequence shown in SEQ ID NO:7 or SEQ ID NO:8, in particular in SEQ ID NO:7.

The truncated form of GAA according to the invention is a N-terminally truncated form of a parent GAA polypeptide, wherein at least one amino acid is deleted from the N-terminal end of said parent GAA polypeptide. For example, the truncated GAA polypeptide may have 1 to 75 consecutive amino acids or more than 75 consecutive amino acids truncated from its N-terminal end as compared to the parent GAA polypeptide. Specifically, the truncated GAA polypeptide may have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74 or 75 consecutive amino acids truncated from its N-terminal end as compared to the parent GAA protein (in particular a truncated form of the parent hGAA protein shown in SEQ ID NO: 7 or SEQ ID NO: 8, in particular in SEQ ID NO: 7). Using an alternative nomenclature, the GAA polypeptide resulting from the truncation of 1 amino acid in the parent GAA polypeptide is referred to as 41 GAA truncated form, the GAA polypeptide resulting from the truncation of 2 consecutive amino acids from the N-terminal end is referred to as Δ2 GAA truncated form, the GAA polypeptide resulting from the truncation of 3 consecutive amino acids in the parent GAA polypeptide is referred to as 43 GAA truncated form), etc. In a particular embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, Δ43, Δ44, Δ45, Δ46, Δ47, Δ48, Δ49, Δ50, Δ51, Δ52, Δ53, Δ54, Δ55, Δ56, Δ57, Δ58, Δ59, Δ60, Δ61, Δ62, Δ63, Δ64, Δ65, Δ66, Δ67, Δ68, Δ69, Δ70, Δ71, Δ72, Δ73, Δ74 or Δ75 GAA truncated form (in particular a truncated form of the parent hGAA protein shown in SEQ ID NO: 7 or SEQ ID NO:8, in particular in SEQ ID NO:7).

In another particular embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, Δ43, Δ44, Δ45, Δ46 or Δ47 GAA truncated form (in particular a truncated form of the parent hGAA protein shown in SEQ ID NO: 7 or SEQ ID NO: 8, in particular in SEQ ID NO: 7).

In another particular embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, Δ43, Δ44, Δ45 or Δ46 GAA truncated form (in particular a truncated form of the parent hGAA protein shown in SEQ ID NO: 7 or SEQ ID NO: 8, in particular in SEQ ID NO: 7).

In another particular embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, Δ43, Δ44 or Δ45 GAA truncated form (in particular a truncated form of the parent hGAA protein shown in SEQ ID NO: 7 or SEQ ID NO: 8, in particular in SEQ ID NO: 7).

In a further particular embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, Δ43 or Δ44 GAA truncated form (in particular a truncated form of the parent hGAA protein shown in SEQ ID NO: 7 or SEQ ID NO: 8, in particular in SEQ ID NO: 7).

In a further particular embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42 or Δ43 GAA truncated form (in particular a truncated form of the parent hGAA protein shown in SEQ ID NO: 7 or SEQ ID NO: 8, in particular in SEQ ID NO: 7).

In a further particular embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41 or Δ42 GAA truncated form (in particular a truncated form of the parent hGAA protein shown in SEQ ID NO: 7 or SEQ ID NO: 8, in particular in SEQ ID NO: 7).

In a further particular embodiment, the truncated GAA polypeptide of the invention is a Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42 or Δ43 GAA truncated form (in particular a truncated form of the parent hGAA protein shown in SEQ ID NO: 7 or SEQ ID NO: 8, in particular in SEQ ID NO: 7).

In a further particular embodiment, the truncated GAA polypeptide of the invention is a 43, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42 or Δ43 GAA truncated form (in particular a truncated form of the parent hGAA protein shown in SEQ ID NO: 7 or SEQ ID NO: 8, in particular in SEQ ID NO: 7).

In a further particular embodiment, the truncated GAA polypeptide of the invention is a Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42 or Δ43 GAA truncated form (in particular a truncated form of the parent hGAA protein shown in SEQ ID NO: 7 or SEQ ID NO: 8, in particular in SEQ ID NO: 7).

In a further particular embodiment, the truncated GAA polypeptide of the invention is a Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42 or Δ43 GAA truncated form (in particular a truncated form of the parent hGAA protein shown in SEQ ID NO: 7 or SEQ ID NO: 8, in particular in SEQ ID NO: 7).

In a further particular embodiment, the truncated GAA polypeptide of the invention is a Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42 or Δ43 GAA truncated form (in particular a truncated form of the parent hGAA protein shown in SEQ ID NO: 7 or SEQ ID NO: 8, in particular in SEQ ID NO: 7).

In a further particular embodiment, the truncated GAA polypeptide of the invention is a Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42 or Δ43 GAA truncated form (in particular a truncated form of the parent hGAA protein shown in SEQ ID NO: 7 or SEQ ID NO: 8, in particular in SEQ ID NO: 7).

In a further particular embodiment, the truncated GAA polypeptide of the invention is a Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42 or Δ43 GAA truncated form (in particular a truncated form of the parent hGAA protein shown in SEQ ID NO: 7 or SEQ ID NO: 8, in particular in SEQ ID NO: 7).

In a further particular embodiment, the truncated GAA polypeptide of the invention is a Δ6, Δ7, Δ8, Δ9 or Δ10 truncated form of GAA (in particular of the hGAA protein shown in SEQ ID NO: 7 or SEQ ID NO: 8, in particular in SEQ ID NO: 7), in particular a Δ7, Δ8 or Δ9 truncated form of GAA (in particular of the hGAA protein shown in SEQ ID NO: 7 or SEQ ID NO: 8, in particular in SEQ ID NO: 7), more particularly a Δ8 truncated form of GAA (in particular of the hGAA protein shown in SEQ ID NO: 7 or SEQ ID NO: 8, in particular in SEQ ID NO: 7).

In a further particular embodiment, the truncated GAA polypeptide of the invention is a Δ27, Δ28, Δ29, Δ30 or Δ31 truncated form of GAA (in particular of the hGAA protein shown in SEQ ID NO: 7 or SEQ ID NO: 8, particular in SEQ ID NO: 7), in particular a Δ28, Δ29 or Δ30 truncated form of GAA (in particular of the hGAA protein shown in SEQ ID NO: 7 or SEQ ID NO: 8, in particular in SEQ ID NO: 7), more particularly a Δ29 truncated form of GAA (in particular of the hGAA protein shown in SEQ ID NO: 7 or SEQ ID NO: 8, particular in SEQ ID NO: 7).

In another particular embodiment, the truncated GAA polypeptide of the invention is a Δ40, Δ41, Δ42, Δ43, or Δ44 truncated form of GAA (in particular of the hGAA protein shown in SEQ ID NO: 7 or SEQ ID NO: 8, particular in SEQ ID NO: 7), in particular a Δ41, Δ42 or Δ43 truncated form of GAA (in particular of the hGAA protein shown in SEQ ID NO: 7 or SEQ ID NO: 8, in particular in SEQ ID NO: 7), more particularly a Δ42 truncated form of GAA (in particular of the hGAA protein shown in SEQ ID NO: 7 or SEQ ID NO: 8, particular in SEQ ID NO: 7).

In a further particular embodiment, the truncated GAA polypeptide of the invention is a Δ41, Δ42, Δ43, Δ44 or Δ45 truncated form of GAA (in particular of the hGAA protein shown in SEQ ID NO: 7), in particular a Δ42, Δ43 or Δ44 truncated form of GAA (in particular of the hGAA protein shown in SEQ ID NO: 7 or SEQ ID NO: 8, in particular in SEQ ID NO: 7), more particularly a Δ43 truncated form of GAA (in particular of the hGAA protein shown in SEQ ID NO: 7).

In another embodiment, the truncated GAA polypeptide of the invention is a Δ6, Δ7, Δ8, Δ9, Δ10, Δ27, Δ28, Δ29, Δ30, Δ31, Δ40, Δ41, Δ42, Δ43, Δ44, Δ45, Δ46 or Δ47 truncated form of GAA (in particular of the hGAA protein shown in SEQ ID NO: 7 or SEQ ID NO: 8, particular in SEQ ID NO: 7).

In another embodiment, the truncated GAA polypeptide of the invention is a Δ7, Δ8, Δ9, Δ28, Δ29, Δ30, Δ41, Δ42, Δ43 or Δ44 truncated form of GAA (in particular of the hGAA protein shown in SEQ ID NO: 7 or SEQ ID NO: 8, particular in SEQ ID NO: 7).

In another embodiment, the truncated GAA polypeptide of the invention is a Δ6, Δ7, Δ8, Δ9, Δ10, Δ40, Δ41, Δ42, Δ43 or Δ44, truncated form of GAA (in particular of the hGAA protein shown in SEQ ID NO: 7 or SEQ ID NO: 8, particular in SEQ ID NO: 7).

In another embodiment, the truncated GAA polypeptide of the invention is a Δ8, Δ29, Δ42, Δ43 or Δ47 truncated form of GAA (in particular of the hGAA protein shown in SEQ ID NO: 7 or SEQ ID NO: 8, particular in SEQ ID NO: 7).

In another embodiment, the truncated GAA polypeptide of the invention is a Δ8, Δ29, Δ42 or Δ43 truncated form of GAA (in particular of the hGAA protein shown in SEQ ID NO: 7 or SEQ ID NO: 8, particular in SEQ ID NO: 7).

In another embodiment, the truncated GAA polypeptide of the invention is a Δ8 or Δ42 truncated form of GAA (in particular of the hGAA protein shown in SEQ ID NO: 7 or SEQ ID NO: 8, particular in SEQ ID NO: 7).

In a particular embodiment, of the invention, the truncated GAA polypeptide of the invention is a truncated form of a functional human GAA polypeptide. In a further particular embodiment, the parent hGAA polypeptide is the hGAA polypeptide shown in SEQ ID NO: 7 or SEQ ID NO: 8, in particular in SEQ ID NO: 7. In a variant of this embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, Δ43, Δ44, Δ45, Δ46, Δ47, Δ48, Δ49, Δ50, Δ51, Δ52, Δ53, Δ54, Δ55, Δ56, Δ57, Δ58, Δ59, Δ60, Δ61, Δ62, Δ63, Δ64, Δ65, Δ66, Δ67, Δ68, Δ69, Δ70, Δ71, Δ72, Δ73, Δ74 or Δ75 GAA truncated form of a hGAA polypeptide, and more particularly of the hGAA polypeptide shown in SEQ ID NO: 7 or SEQ ID NO: 8, even more particularly in SEQ ID NO: 7, or of a functional variant thereof comprising amino acid substitutions in the sequence shown in SEQ ID NO: 7 or SEQ ID NO: 8, in particular SEQ ID NO: 7, and having at least 75, 80, 85, 90, 91, 92, 93, 94, 95, 96, 97, 98 or 99 percent identity to SEQ ID NO: 7 SEQ ID NO: 8, in particular SEQ ID NO: 7.

In a variant of this embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, Δ43, Δ44, Δ45, Δ46 or Δ47 GAA truncated form of a hGAA polypeptide, and more particularly of the hGAA polypeptide shown in SEQ ID NO: 7 or SEQ ID NO: 8, even more particularly in SEQ ID NO: 7, or of a functional variant thereof comprising amino acid substitutions in the sequence shown in SEQ ID NO: 7 or SEQ ID NO: 8, in particular SEQ ID NO: 7, and having at least 75, 80, 85, 90, 91, 92, 93, 94, 95, 96, 97, 98 or 99 percent identity to SEQ ID NO: 7 SEQ ID NO: 8, in particular SEQ ID NO: 7.

In a variant of this embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, Δ43, Δ44, Δ45 or Δ46 GAA truncated form of a hGAA polypeptide, and more particularly of the hGAA polypeptide shown in SEQ ID NO: 7 or SEQ ID NO: 8, even more particularly in SEQ ID NO: 7, or of a functional variant thereof comprising amino acid substitutions in the sequence shown in SEQ ID NO: 7 or SEQ ID NO: 8, in particular SEQ ID NO: 7, and having at least 75, 80, 85, 90, 91, 92, 93, 94, 95, 96, 97, 98 or 99 percent identity to SEQ ID NO: 7 SEQ ID NO: 8, in particular SEQ ID NO: 7.

In a variant of this embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, Δ43, Δ44 or Δ45 GAA truncated form of a hGAA polypeptide, and more particularly of the hGAA polypeptide shown in SEQ ID NO: 7 or SEQ ID NO: 8, even more particularly in SEQ ID NO: 7, or of a functional variant thereof comprising amino acid substitutions in the sequence shown in SEQ ID NO: 7 or SEQ ID NO: 8, in particular SEQ ID NO: 7, and having at least 75, 80, 85, 90, 91, 92, 93, 94, 95, 96, 97, 98 or 99 percent identity to SEQ ID NO: 7 SEQ ID NO: 8, in particular SEQ ID NO: 7.

In another variant of this embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, Δ43 or Δ44 GAA truncated form of a hGAA polypeptide, and more particularly of the hGAA polypeptide shown in SEQ ID NO: 7 or SEQ ID NO: 8, even more particularly in SEQ ID NO: 7, or of a functional variant thereof comprising amino acid substitutions in the sequence shown in SEQ ID NO: 7 or SEQ ID NO: 8, in particular SEQ ID NO: 7, and having at least 75, 80, 85, 90, 91, 92, 93, 94, 95, 96, 97, 98 or 99 percent identity to SEQ ID NO: 7 SEQ ID NO: 8, in particular SEQ ID NO: 7.

In another variant of this embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, or Δ43 GAA truncated form of a hGAA polypeptide, and more particularly of the hGAA polypeptide shown in SEQ ID NO: 7 or SEQ ID NO: 8, even more particularly in SEQ ID NO: 7, or of a functional variant thereof comprising amino acid substitutions in the sequence shown in SEQ ID NO: 7 or SEQ ID NO: 8, in particular SEQ ID NO: 7, and having at least 75, 80, 85, 90, 91, 92, 93, 94, 95, 96, 97, 98 or 99 percent identity to SEQ ID NO: 7 SEQ ID NO: 8, in particular SEQ ID NO: 7.

In another variant of this embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41 or Δ42 GAA truncated form of a hGAA polypeptide, and more particularly of the hGAA polypeptide shown in SEQ ID NO: 7 or SEQ ID NO: 8, even more particularly in SEQ ID NO: 7, or of a functional variant thereof comprising amino acid substitutions in the sequence shown in SEQ ID NO: 7 or SEQ ID NO: 8, in particular SEQ ID NO: 7, and having at least 75, 80, 85, 90, 91, 92, 93, 94, 95, 96, 97, 98 or 99 percent identity to SEQ ID NO: 7 SEQ ID NO: 8, in particular SEQ ID NO: 7.

In another variant of this embodiment, the truncated GAA polypeptide of the invention is a Δ2, Δ3, 44, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41 or Δ42 GAA truncated form of a hGAA polypeptide, and more particularly of the hGAA polypeptide shown in SEQ ID NO: 7 or SEQ ID NO: 8, even more particularly in SEQ ID NO: 7, or of a functional variant thereof comprising amino acid substitutions in the sequence shown in SEQ ID NO: 7 or SEQ ID NO: 8, in particular SEQ ID NO: 7, and having at least 75, 80, 85, 90, 91, 92, 93, 94, 95, 96, 97, 98 or 99 percent identity to SEQ ID NO: 7 SEQ ID NO: 8, in particular SEQ ID NO: 7.

In another variant of this embodiment, the truncated GAA polypeptide of the invention is a 43, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41 or Δ42 GAA truncated form of a hGAA polypeptide, and more particularly of the hGAA polypeptide shown in SEQ ID NO: 7 or SEQ ID NO: 8, even more particularly in SEQ ID NO: 7, or of a functional variant thereof comprising amino acid substitutions in the sequence shown in SEQ ID NO: 7 or SEQ ID NO: 8, in particular SEQ ID NO: 7, and having at least 75, 80, 85, 90, 91, 92, 93, 94, 95, 96, 97, 98 or 99 percent identity to SEQ ID NO: 7 SEQ ID NO: 8, in particular SEQ ID NO: 7.

In another variant of this embodiment, the truncated GAA polypeptide of the invention is a Δ4, Δ5, 46, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41 or Δ42 GAA truncated form of a hGAA polypeptide, and more particularly of the hGAA polypeptide shown in SEQ ID NO: 7 or SEQ ID NO: 8, even more particularly in SEQ ID NO: 7, or of a functional variant thereof comprising amino acid substitutions in the sequence shown in SEQ ID NO: 7 or SEQ ID NO: 8, in particular SEQ ID NO: 7, and having at least 75, 80, 85, 90, 91, 92, 93, 94, 95, 96, 97, 98 or 99 percent identity to SEQ ID NO: 7 SEQ ID NO: 8, in particular SEQ ID NO: 7.

In another variant of this embodiment, the truncated GAA polypeptide of the invention is a Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41 or Δ42 GAA truncated form of a hGAA polypeptide, and more particularly of the hGAA polypeptide shown in SEQ ID NO: 7 or SEQ ID NO: 8, even more particularly in SEQ ID NO: 7, or of a functional variant thereof comprising amino acid substitutions in the sequence shown in SEQ ID NO: 7 or SEQ ID NO: 8, in particular SEQ ID NO: 7, and having at least 75, 80, 85, 90, 91, 92, 93, 94, 95, 96, 97, 98 or 99 percent identity to SEQ ID NO: 7 SEQ ID NO: 8, in particular SEQ ID NO: 7.

In another variant of this embodiment, the truncated GAA polypeptide of the invention is a Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41 or Δ42 GAA truncated form of a hGAA polypeptide, and more particularly of the hGAA polypeptide shown in SEQ ID NO: 7 or SEQ ID NO: 8, even more particularly in SEQ ID NO: 7, or of a functional variant thereof comprising amino acid substitutions in the sequence shown in SEQ ID NO: 7 or SEQ ID NO: 8, in particular SEQ ID NO: 7, and having at least 75, 80, 85, 90, 91, 92, 93, 94, 95, 96, 97, 98 or 99 percent identity to SEQ ID NO: 7 SEQ ID NO: 8, in particular SEQ ID NO: 7.

In another variant of this embodiment, the truncated GAA polypeptide of the invention is a Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41 or Δ42 GAA truncated form of a hGAA polypeptide, and more particularly of the hGAA polypeptide shown in SEQ ID NO: 7 or SEQ ID NO: 8, even more particularly in SEQ ID NO: 7, or of a functional variant thereof comprising amino acid substitutions in the sequence shown in SEQ ID NO: 7 or SEQ ID NO: 8, in particular SEQ ID NO: 7, and having at least 75, 80, 85, 90, 91, 92, 93, 94, 95, 96, 97, 98 or 99 percent identity to SEQ ID NO: 7 SEQ ID NO: 8, in particular SEQ ID NO: 7.

In another variant of this embodiment, the truncated GAA polypeptide of the invention is a Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41 or Δ42 GAA truncated form of a hGAA polypeptide, and more particularly of the hGAA polypeptide shown in SEQ ID NO: 7 or SEQ ID NO: 8, even more particularly in SEQ ID NO: 7, or of a functional variant thereof comprising amino acid substitutions in the sequence shown in SEQ ID NO: 7 or SEQ ID NO: 8, in particular SEQ ID NO: 7, and having at least 75, 80, 85, 90, 91, 92, 93, 94, 95, 96, 97, 98 or 99 percent identity to SEQ ID NO: 7 SEQ ID NO: 8, in particular SEQ ID NO: 7.

In another variant of this embodiment, the truncated GAA polypeptide of the invention is a Δ2, Δ3, 44, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, or Δ43 GAA truncated form of a hGAA polypeptide, and more particularly of the hGAA polypeptide shown in SEQ ID NO: 7 or SEQ ID NO: 8, even more particularly in SEQ ID NO: 7, or of a functional variant thereof comprising amino acid substitutions in the sequence shown in SEQ ID NO: 7 or SEQ ID NO: 8, in particular SEQ ID NO: 7, and having at least 75, 80, 85, 90, 91, 92, 93, 94, 95, 96, 97, 98 or 99 percent identity to SEQ ID NO: 7 SEQ ID NO: 8, in particular SEQ ID NO: 7.

In another variant of this embodiment, the truncated GAA polypeptide of the invention is a 43, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, or Δ43 GAA truncated form of a hGAA polypeptide, and more particularly of the hGAA polypeptide shown in SEQ ID NO: 7 or SEQ ID NO: 8, even more particularly in SEQ ID NO: 7, or of a functional variant thereof comprising amino acid substitutions in the sequence shown in SEQ ID NO: 7 or SEQ ID NO: 8, in particular SEQ ID NO: 7, and having at least 75, 80, 85, 90, 91, 92, 93, 94, 95, 96, 97, 98 or 99 percent identity to SEQ ID NO: 7 SEQ ID NO: 8, in particular SEQ ID NO: 7.

In another variant of this embodiment, the truncated GAA polypeptide of the invention is a Δ4, Δ5, 46, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, or Δ43 GAA truncated form of a hGAA polypeptide, and more particularly of the hGAA polypeptide shown in SEQ ID NO: 7 or SEQ ID NO: 8, even more particularly in SEQ ID NO: 7, or of a functional variant thereof comprising amino acid substitutions in the sequence shown in SEQ ID NO: 7 or SEQ ID NO: 8, in particular SEQ ID NO: 7, and having at least 75, 80, 85, 90, 91, 92, 93, 94, 95, 96, 97, 98 or 99 percent identity to SEQ ID NO: 7 SEQ ID NO: 8, in particular SEQ ID NO: 7.

In another variant of this embodiment, the truncated GAA polypeptide of the invention is a Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, or Δ43 GAA truncated form of a hGAA polypeptide, and more particularly of the hGAA polypeptide shown in SEQ ID NO: 7 or SEQ ID NO: 8, even more particularly in SEQ ID NO: 7, or of a functional variant thereof comprising amino acid substitutions in the sequence shown in SEQ ID NO: 7 or SEQ ID NO: 8, in particular SEQ ID NO: 7, and having at least 75, 80, 85, 90, 91, 92, 93, 94, 95, 96, 97, 98 or 99 percent identity to SEQ ID NO: 7 SEQ ID NO: 8, in particular SEQ ID NO: 7.

In another variant of this embodiment, the truncated GAA polypeptide of the invention is a Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, or Δ43 GAA truncated form of a hGAA polypeptide, and more particularly of the hGAA polypeptide shown in SEQ ID NO: 7 or SEQ ID NO: 8, even more particularly in SEQ ID NO: 7, or of a functional variant thereof comprising amino acid substitutions in the sequence shown in SEQ ID NO: 7 or SEQ ID NO: 8, in particular SEQ ID NO: 7, and having at least 75, 80, 85, 90, 91, 92, 93, 94, 95, 96, 97, 98 or 99 percent identity to SEQ ID NO: 7 SEQ ID NO: 8, in particular SEQ ID NO: 7.

In another variant of this embodiment, the truncated GAA polypeptide of the invention is a Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, or Δ43 GAA truncated form of a hGAA polypeptide, and more particularly of the hGAA polypeptide shown in SEQ ID NO: 7 or SEQ ID NO: 8, even more particularly in SEQ ID NO: 7, or of a functional variant thereof comprising amino acid substitutions in the sequence shown in SEQ ID NO: 7 or SEQ ID NO: 8, in particular SEQ ID NO: 7, and having at least 75, 80, 85, 90, 91, 92, 93, 94, 95, 96, 97, 98 or 99 percent identity to SEQ ID NO: 7 SEQ ID NO: 8, in particular SEQ ID NO: 7.

In another variant of this embodiment, the truncated GAA polypeptide of the invention is a Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, or Δ43 GAA truncated form of a hGAA polypeptide, and more particularly of the hGAA polypeptide shown in SEQ ID NO: 7 or SEQ ID NO: 8, even more particularly in SEQ ID NO: 7, or of a functional variant thereof comprising amino acid substitutions in the sequence shown in SEQ ID NO: 7 or SEQ ID NO: 8, in particular SEQ ID NO: 7, and having at least 75, 80, 85, 90, 91, 92, 93, 94, 95, 96, 97, 98 or 99 percent identity to SEQ ID NO: 7 SEQ ID NO: 8, in particular SEQ ID NO: 7.

In another variant of this embodiment, the truncated GAA polypeptide of the invention is a Δ6, Δ7, Δ8, 49 or Δ10, in particular a Δ7, Δ8 or Δ9, more particularly a Δ8 truncated form of a hGAA polypeptide, and more particularly of the hGAA polypeptide shown in SEQ ID NO: 7 or SEQ ID NO: 8, in particular in SEQ ID NO: 7, or of a functional variant thereof comprising amino acid substitutions in the sequence shown in SEQ ID NO: 7 or SEQ ID NO: 8, in particular in SEQ ID NO: 7, and having at least 80, 85, 90, 95, 96, 97, 98 or 99 percent identity to SEQ ID NO: 7 or SEQ ID NO: 8, in particular in SEQ ID NO: 7.

In another variant of this embodiment, the truncated GAA polypeptide of the invention is a Δ27, Δ28, Δ29, Δ30 or Δ31, in particular a Δ28, Δ29 or Δ30, more particularly a Δ29 truncated form of a hGAA polypeptide, and more particularly of the hGAA polypeptide shown in SEQ ID NO: 7 or SEQ ID NO: 8, in particular in SEQ ID NO: 7, or of a functional variant thereof comprising amino acid substitutions in the sequence shown in SEQ ID NO: 7 or SEQ ID NO: 8, in particular in SEQ ID NO: 7, and having at least 80, 85, 90, 95, 96, 97, 98 or 99 percent identity to SEQ ID NO: 7 or SEQ ID NO: 8, in particular in SEQ ID NO: 7.

In another variant of this embodiment, the truncated GAA polypeptide of the invention is a Δ40, Δ41, Δ42, Δ43 or Δ44, in particular a Δ41, Δ42 or Δ43, more particularly a Δ42 truncated form of a hGAA polypeptide, and more particularly of the hGAA polypeptide shown in SEQ ID NO: 7 or SEQ ID NO: 8, in particular in SEQ ID NO: 7, or of a functional variant thereof comprising amino acid substitutions in the sequence shown in SEQ ID NO: 7 or SEQ ID NO: 8, in particular in SEQ ID NO: 7, and having at least 80, 85, 90, 95, 96, 97, 98 or 99 percent identity to SEQ ID NO: 7 or SEQ ID NO: 8, in particular in SEQ ID NO: 7.

In another variant of this embodiment, the truncated GAA polypeptide of the invention is a Δ41, Δ42, Δ43, Δ44 or 445, in particular a Δ42, Δ43 or Δ44, more particularly a Δ43 truncated form of a hGAA polypeptide, and more particularly of the hGAA polypeptide shown in SEQ ID NO: 7 or SEQ ID NO: 8, in particular in SEQ ID NO: 7, or of a functional variant thereof comprising amino acid substitutions in the sequence shown in SEQ ID NO: 7 or SEQ ID NO: 8, in particular in SEQ ID NO: 7, and having at least 80, 85, 90, 95, 96, 97, 98 or 99 percent identity to SEQ ID NO: 7 or SEQ ID NO: 8, in particular in SEQ ID NO: 7.

In another variant of this embodiment, the truncated GAA polypeptide of the invention is a Δ6, Δ7, Δ8, Δ9, Δ10, Δ27, Δ28, Δ29, Δ30, Δ31, Δ40, Δ41, Δ42, Δ43, Δ44 or Δ45, in particular a Δ7, Δ8, Δ9, Δ28, Δ29, Δ30, Δ41, Δ42, Δ43 or Δ44, in particular a Δ8, Δ29, Δ42 or Δ43 truncated form of a hGAA polypeptide, and more particularly of the hGAA polypeptide shown in SEQ ID NO: 7 or SEQ ID NO: 8, in particular in SEQ ID NO: 7, or of a functional variant thereof comprising amino acid substitutions in the sequence shown in SEQ ID NO: 7 or SEQ ID NO: 8, in particular in SEQ ID NO: 7, and having at least 80, 85, 90, 95, 96, 97, 98 or 99 percent identity to SEQ ID NO: 7 or SEQ ID NO: 8, in particular in SEQ ID NO: 7.

In another variant of this embodiment, the truncated GAA polypeptide of the invention is a Δ6, Δ7, Δ8, Δ9, Δ10, Δ40, Δ41, Δ42, Δ43 or Δ44, in particular a Δ8 or Δ42 truncated form of a hGAA polypeptide, and more particularly of the hGAA polypeptide shown in SEQ ID NO: 7 or SEQ ID NO: 8, in particular in SEQ ID NO: 7, or of a functional variant thereof comprising amino acid substitutions in the sequence shown in SEQ ID NO: 7 or SEQ ID NO: 8, in particular in SEQ ID NO: 7, and having at least 80, 85, 90, 95, 96, 97, 98 or 99 percent identity to SEQ ID NO: 7 or SEQ ID NO: 8, in particular in SEQ ID NO: 7.

In another variant of this embodiment, the truncated GAA polypeptide of the invention is a Δ8, Δ29, Δ42, Δ43 or Δ47 truncated form of a hGAA polypeptide, and more particularly of the hGAA polypeptide shown in SEQ ID NO: 7 or SEQ ID NO: 8, in particular in SEQ ID NO: 7, or of a functional variant thereof comprising amino acid substitutions in the sequence shown in SEQ ID NO: 7 or SEQ ID NO: 8, in particular in SEQ ID NO: 7, and having at least 80, 85, 90, 95, 96, 97, 98 or 99 percent identity to SEQ ID NO: 7 or SEQ ID NO: 8, in particular in SEQ ID NO: 7.

In another variant of this embodiment, the truncated GAA polypeptide of the invention is a Δ8, Δ29, Δ42 or Δ43 truncated form of a hGAA polypeptide, and more particularly of the hGAA polypeptide shown in SEQ ID NO: 7 or SEQ ID NO: 8, in particular in SEQ ID NO: 7, or of a functional variant thereof comprising amino acid substitutions in the sequence shown in SEQ ID NO: 7 or SEQ ID NO: 8, in particular in SEQ ID NO: 7, and having at least 80, 85, 90, 95, 96, 97, 98 or 99 percent identity to SEQ ID NO: 7 or SEQ ID NO: 8, in particular in SEQ ID NO: 7.

In another variant of this embodiment, the truncated GAA polypeptide of the invention is a Δ8 or Δ42 truncated form of a hGAA polypeptide, and more particularly of the hGAA polypeptide shown in SEQ ID NO: 7 or SEQ ID NO: 8, in particular in SEQ ID NO: 7, or of a functional variant thereof comprising amino acid substitutions in the sequence shown in SEQ ID NO: 7 or SEQ ID NO: 8, in particular in SEQ ID NO: 7, and having at least 80, 85, 90, 95, 96, 97, 98 or 99 percent identity to SEQ ID NO: 7 or SEQ ID NO: 8, in particular in SEQ ID NO: 7.

In a particular embodiment, the truncated GAA polypeptide of the invention is a Δ42 truncated form of GAA (in particular of the hGAA protein shown in SEQ ID NO: 7 or SEQ ID NO: 8, particular in SEQ ID NO: 7).

In a particular embodiment, the truncated GAA polypeptide is a Δ42 truncated form of a hGAA polypeptide, and more particularly of the hGAA polypeptide shown in SEQ ID NO:7 or SEQ ID NO:8, in particular in SEQ ID NO:7, or of a functional variant thereof comprising amino acid substitutions in the sequence shown in SEQ ID NO:7 or SEQ ID NO:8, in particular in SEQ ID NO:7, and having at least 80, 85, 90, 95, 96, 97, 98 or 99 percent identity to SEQ ID NO:7 or SEQ ID NO:8, in particular in SEQ ID NO:7. In a particular embodiment, the functional variant of a GAA polypeptide may have, in addition to the truncation defined above, between 0 and 50, between 0 and 30, between 0 and 20, between 0 and 15, between 0 and 10, or between 0 and 5 amino acid changes to the parent GAA polypeptide, such as the parent GAA polypeptide shown in SEQ ID NO: 7 or SEQ ID NO:8, in particular SEQ ID NO:7.

In a specific embodiment, the truncated hGAA polypeptide of the invention has an amino acid sequence consisting of the sequence shown in SEQ ID NO: 66, SEQ ID NO: 9, SEQ ID NO: 67, SEQ ID NO: 68 or SEQ ID NO: 69, or a functional variant thereof comprising from 1 to 5 amino, in particular from 1 to 4, in particular from 1 to 3, more particularly from 1 to 2, in particular 1 amino acid substitution as compared to the sequence shown in SEQ ID NO: 66, SEQ ID NO: 9, SEQ ID NO: 67, SEQ ID NO: 68 or SEQ ID NO: 69. In another specific embodiment, the truncated hGAA polypeptide of the invention has an amino acid sequence consisting of the sequence shown in SEQ ID NO: 66, SEQ ID NO: 9, SEQ ID NO: 67 or SEQ ID NO: 68, or a functional variant thereof comprising from 1 to 5 amino acid substitutions as compared to the sequence shown in SEQ ID NO: 66, SEQ ID NO: 9, SEQ ID NO: 67 or SEQ ID NO: 68. In a specific embodiment, the truncated hGAA polypeptide of the invention has an amino acid sequence consisting of the sequence shown in SEQ ID NO: 66 or SEQ ID NO: 9, or a functional variant thereof comprising from 1 to 5 amino, in particular from 1 to 4, in particular from 1 to 3, more particularly from 1 to 2, in particular 1 amino acid substitution as compared to the sequence shown in SEQ ID NO: 66 or SEQ ID NO: 9.

In a specific embodiment, the truncated hGAA polypeptide of the invention has an amino acid sequence consisting of the sequence shown in SEQ ID NO: 9 or a functional variant thereof comprising from 1 to 5, in particular from 1 to 4, in particular from 1 to 3, more particularly from 1 to 2, in particular 1 amino acid substitution as compared to the sequence shown in SEQ ID NO: 9.

The nucleic acid sequence encoding the functional GAA polypeptide, in particular the truncated GAA polypeptide can be optimized for expression of the GAA polypeptide in vivo. Sequence optimization may include a number of changes in a nucleic acid sequence, including codon optimization, increase of GC content, decrease of the number of CpG islands, decrease of the number of alternative open reading frames (ARFs) and decrease of the number of splice donor and splice acceptor sites. Because of the degeneracy of the genetic code, different nucleic acid molecules may encode the same protein. It is also well known that the genetic codes of different organisms are often biased towards using one of the several codons that encode the same amino acid over the others. Through codon optimization, changes are introduced in a nucleotide sequence that take advantage of the codon bias existing in a given cellular context so that the resulting codon optimized nucleotide sequence is more likely to be expressed in such given cellular context at a relatively high level compared to the non-codon optimised sequence. In a preferred embodiment of the invention, such sequence optimized nucleotide sequence encoding a truncated GAA is codon-optimized to improve its expression in human cells compared to non-codon optimized nucleotide sequences coding for the same truncated GAA protein, for example by taking advantage of the human specific codon usage bias.

In a particular embodiment, the optimized GAA coding sequence is codon optimized, and/or has an increased GC content and/or has a decreased number of alternative open reading frames, and/or has a decreased number of splice donor and/or splice acceptor sites, as compared to nucleotides 82-2859 of the wild-type hGAA coding sequence of SEQ ID NO: 1. For example, nucleic acid sequence of the invention results in an at least 2, 3, 4, 5 or 10% increase of GC content in the GAA sequence as compared to the sequence of the wild-type GAA sequence. In a particular embodiment, the nucleic acid sequence of the invention results in a 2, 3, 4 or, more particularly, 5% or 10% (particularly 5%) increase of GC content in the GAA sequence as compared to the sequence of the wild-type GAA nucleotide sequence. In a particular embodiment, the nucleic acid sequence of the invention encoding a functional GAA polypeptide is "substantially identical", that is, about 70% identical, more preferably about 80% identical, even more preferably about 90% identical, even more preferably about 95% identical, even more preferably about 97%, 98% or even 99% identical to nucleotides 82-2859 of the sequence shown in SEQ ID NO: 1. As mentioned above, in addition to the GC content and/or number of ARFs, sequence optimization may also comprise a decrease in the number of CpG islands in the sequence and/or a decrease in the number of splice donor and acceptor sites. Of course, as is well known to those skilled in the art, sequence optimization is a balance between all these parameters, meaning that a sequence may be considered optimized if at least one of the above parameters is improved while one or more of the other parameters is not, as long as the optimized sequence leads to an improvement of the transgene, such as an improved expression and/or a decreased immune response to the transgene in vivo.

In addition, the adaptiveness of a nucleotide sequence encoding a functional GAA to the codon usage of human cells may be expressed as codon adaptation index (CAI). A codon adaptation index is herein defined as a measurement of the relative adaptiveness of the codon usage of a gene towards the codon usage of highly expressed human genes. The relative adaptiveness (w) of each codon is the ratio of the usage of each codon, to that of the most abundant codon for the same amino acid. The CAI is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Kim et al, Gene. 1997, 199:293-301; zur Megede et al, Journal of Virology, 2000, 74: 2628-2635). Preferably, a nucleic acid molecule encoding a GAA has a CAI of at least 0.75 (in particular 0.77), 0.8, 0.85, 0.90, 0.92 or 0.94.

The term "nucleic acid sequence" (or nucleic acid molecule) refers to a DNA or RNA molecule in single or double stranded form, particularly a DNA encoding a functional GAA polypeptide according to the invention.

In another embodiment of the invention, the part of the nucleic acid molecule of the invention encoding the truncated GAA polypeptide has at least 85 percent, more preferably at least 90 percent, and even more preferably at least 92 percent identity, in particular at least 95 percent identity, for example at least 98, 99 or 100 percent identity to the corresponding part of the nucleotide sequence SEQ ID NO: 2 or 3, which are sequence-optimized sequences.

In a preferred embodiment, the part of the nucleic acid molecule of the invention encoding the truncated GAA polypeptide has at least 85 percent, more preferably at least 90 percent, and even more preferably at least 92 percent identity, in particular at least 95 percent identity, for example at least 98, 99 or 100 percent identity to the SEQ ID NO:10 or SEQ ID NO:11, preferably SEQ ID NO:10, encoding the polypeptide having the amino acid sequence shown in SEQ ID NO: 9. In a particular embodiment, the nucleic acid sequence encoding the truncated GAA polypeptide consists of the sequence shown in SEQ ID NO:10 or SEQ ID NO:11, preferably SEQ ID NO:10, encoding the polypeptide having the amino acid sequence shown in SEQ ID NO: 9.

In addition, the functional GAA polypeptide may be any of the functional GAA polypeptide described in WO2018/046772, WO2018/046775 and WO2018/046774 patent applications.

Heterologous Moiety

The aim of the present inventors was to improve the activity of circulating peptides in vivo. The present inventors investigated the possibility to improve GAA activity by fusing the GAA polypeptide as defined above with one or more heterologous moieties. By "heterologous moiety" is meant a peptide moiety issued from a peptide or polypeptide different from the peptide of interest, in particular different from GAA. In the context of the invention "heterologous moiety" means any peptide moiety able to improve the activity of the peptide of interest in vivo, for example any peptide moiety improving plasmatic stability, plasmatic activity, lysosomal targeting, uptake to the target tissues such as the CNS or skeletal muscles and/or crossing of the blood brain barrier.

In particular, the nucleic acid molecule of the invention encodes a chimeric polypeptide comprising:

a peptide of interest as defined above, fused to:

one or more heterologous moieties, wherein at least one of the heterologous moieties is a ligand of the Sortilin receptor.

By "ligand of the Sortilin receptor" is meant any molecule that is able to bind the Sortilin receptor, in particular any molecule able to specifically bind the Sortilin receptor. The ligand can be a natural or synthetic molecule which binds to the Sortilin receptor to form a receptor-ligand complex. Preferably, the affinity arises by virtue of the ligand possessing a three-dimensional structure complementary to that of the Sortilin receptor. Preferably, the ligand is a proteinaceous ligand.

Sortilin receptor is a type I membrane glycoprotein belonging to the vacuolar protein sorting 10 protein (Vps10p) receptor family. "Sortilin" is also referred to as Neurotensin receptor 3 (NTR3), Glycoprotein 95 (Gp95) or 100 kDa NT receptor. Human Sortilin is accessed in Swiss Prot under ID No. Q99523. Sortilin is a protein that in humans is encoded by the SORT1 gene on chromosome 1 at the band 1p13.3. The Sortilin receptor is composed of a large extracellular domain (75 kDa), a single transmembrane helix and a short cytoplasmic tail. Sortilin receptor is expressed at high levels in brain, spinal cord, heart, skeletal muscle, thyroid, placenta and testis and expressed at lower levels in lymphoid organs, kidney, colon and liver.

The ligand of the Sortilin receptor may be any natural ligand, such as Spadin, Neurotensin (NT), lipoprotein lipase, the proforms of nerve growth factor-beta (proNGF) and brain derived neurotrophic factor (proBDNF), or the receptor associated protein (RAP).

In a particular embodiment, the ligand of the Sortilin receptor is the Spadin peptide or the Neurotensin peptide or any functional fragment thereof. By "functional fragment" is meant any fragment that is able to bind to the Sortilin receptor and that is able to improve the activity of the peptide of interest, in particular of GAA peptide. In particular, any functional fragment that is able to improve the uptake and/or activity of the peptide of interest in the brain can be used. In a particular embodiment, said functional fragment has at least 5 amino acids.

In a particular embodiment, the ligand of the Sortilin receptor is the Spadin peptide or a functional fragment thereof. In particular, the amino acid sequence of the Spadin peptide may have at least 80% identity, at least 85% identity, at least 90% identity, at least 92% identity, at least 95% identity, at least 98% identity, at least 99% identity or may have 100% identity to the amino acid sequence of SEQ ID NO: 31. For example, the Spadin peptide may have 1, 2, 3, 4 or 5 amino acid changes when compared to the Spadin peptide as shown in SEQ ID NO:31. In a particular embodiment, the Spadin peptide has the amino acid sequence as shown in SEQ ID NO:31.

In particular, the Spadin peptide may be encoded by the nucleotide sequence of SEQ ID NO:14 or by a nucleotide sequence having at least 85% identity, at least 90% identity, at least 92% identity, at least 95% identity, at least 98% identity, at least 99% identity or having 100% identity to the nucleotide sequence of SEQ ID NO: 14.

In another particular embodiment, the ligand of the Sortilin receptor is the Neurotensin peptide or a functional fragment thereof. In particular, the amino acid sequence of the Neurotensin peptide may have at least 80% identity, at least 85% identity, at least 90% identity, at least 92% identity, at least 95% identity, at least 98% identity, at least 99% identity or may have 100% identity to the amino acid sequence of SEQ ID NO: 32 For example, the Neurotensin peptide may have 1, 2, 3, 4 or 5 amino acid changes when compared to the Neurotensin peptide as shown in SEQ ID NO:32. In a particular embodiment, the Neurotensin peptide has the amino acid sequence as shown in SEQ ID NO:32.

In a particular embodiment, the Neurotensin peptide is encoded by the nucleotide sequence of SEQ ID NO: 15 or by a nucleotide sequence having at least 85% identity, at least 90% identity, at least 92% identity, at least 95% identity, at least 98% identity, at least 99% identity or having 100% identity to the nucleotide sequence of SEQ ID NO: 15.

In a particular embodiment, the ligand of the Sortilin receptor is a fragment of the Neurotensin peptide, in particular a fragment of the Neurotensin peptide, as set forth in SEQ ID NO: 32. In particular, the fragment of the Neurotensin peptide may have at least 80% identity, at least 85% identity, at least 90% identity, at least 92% identity, at least 95% identity, at least 98% identity, at least 99% identity or may have 100% identity to the amino acid sequence of SEQ ID NO: 33 For example, the Neurotensin peptide may have 1, 2 or 3 amino acid changes when compared to the fragment of Neurotensin peptide as shown in SEQ ID NO:33. In a particular embodiment, the fragment of the Neurotensin peptide has the amino acid sequence as shown in SEQ ID NO:33.

In particular, the fragment of the Neurotensin peptide is encoded by the nucleotide sequence of SEQ ID NO: 16 or by a nucleotide sequence having at least 85% identity, at least 90% identity, at least 92% identity, at least 95% identity, at least 98% identity, at least 99% identity or having 100% identity to the nucleotide sequence of SEQ ID NO: 16.

In a particular embodiment, the peptide of interest, in particular a functional GAA polypeptide, is fused to at least 1, 2, 3, 4, or at least 5 heterologous moieties, wherein at least one of said heterologous moieties is the ligand of the Sortilin receptor as defined above. In particular, the peptide of interest may be fused to 1, 2, 3, 4 or 5 heterologous moieties. Heterologous moieties other than the ligand of the Sortilin receptor may be any heterologous moiety able to improve the activity of the peptide of interest, in particular GAA. In particular any heterologous moiety improving plasmatic stability, plasmatic activity, lysosomal targeting, uptake to the target tissues and/or crossing of the blood brain barrier may be used.

In a particular embodiment, the peptide of interest is fused to 1, 2, 3, 4 or 5 heterologous moieties, wherein each of the heterologous moieties is a ligand of the Sortilin receptor as defined above. In a particular embodiment, the peptide of interest is fused to 1, 2, 3, 4 or 5 heterologous moieties, wherein each of the heterologous moieties is a Spadin peptide. Thus, in this embodiment, the peptide of interest is fused to a repetition of the same heterologous moiety, which is the Spadin peptide as defined above.

In a particular embodiment, the peptide of interest, in particular the functional GAA peptide as defined above, is fused to one (i.e. one and only one) heterologous moiety, wherein the heterologous moiety is a ligand of Sortilin receptor as defined above, in particular the Spadin peptide, the Neurotensin peptide or any fragment thereof as defined above. In a particular embodiment, the peptide of interest, in particular the functional GAA peptide as defined above, is fused to one (i.e. one and only one) heterologous moiety being the Spadin peptide as defined above.

In a particular embodiment, the peptide of interest is fused to at least 2 heterologous moieties, wherein at least one of the heterologous moieties is the ligand of the Sortilin receptor as defined above, and at least one of the heterologous moieties is a carboxy terminal peptide (CTP) of the human Chorionic Gonadotropin beta-subunit (hCGβ).

The carboxy terminal peptide (CTP) of the human Chorionic Gonadotropin beta-subunit (hCGβ) as described herein comprises the amino acid sequence from position 137 to position 165 of beta subunit of human chorionic gonadotropin, as set forth in SEQ ID NO: 34. In some embodiments, the CTP sequence peptide is 28, 29, 30, 31, 32, 33 or 34 amino acids long. Preferably, the CTP of the hCGβ is 28 amino acids long.

In a particular embodiment, the CTP of the hCGβ is a functional variant which differs from the native CTP by 1-5 amino acid substitutions. By "functional variant" is meant any CTP of the hCGβ able to improve the activity of GAA in vivo. In particular, the amino acid sequence of the CTP of the hCGβ may have a least 85% identity, at least 90% identity, at least 92% identity, at least 95% identity, at least 98% identity, at least 99% identity or may have 100% identity to the amino acid sequence of SEQ ID NO: 12. In a particular embodiment, the amino acid sequence of the CTP of the hCGβ comprises or consists of SEQ ID NO: 12.

In a particular embodiment, the CTP of the hCGβ is encoded by the nucleotide sequence of SEQ ID NO:13 or by a nucleotide sequence having at least 85% identity, at least 90% identity, at least 92% identity, at least 95% identity, at least 98% identity, at least 99% identity or having 100% identity to the nucleotide sequence of SEQ ID NO: 13.

In a particular embodiment, the peptide of interest, in particular the functional GAA polypeptide is fused to two heterologous moieties, one being a CTP of the hCGβ as defined above, and the other being a Spadin peptide as defined above.

In a particular embodiment, the one or more heterologous moieties is/are fused to the N-terminal end and/or to the C-terminal end of the peptide of interest, in particular of the functional GAA polypeptide. In a particular embodiment, one heterologous moiety is fused at the N-terminal end, and the same or a different heterologous moiety is fused to the C-terminal end of the peptide of interest. In a preferred embodiment, the one or more heterologous moieties is/are fused to the N-terminal end of the peptide of interest.

In a preferred embodiment, one heterologous moiety, which is a Spadin peptide as defined above, is fused at the N-terminal end of the peptide of interest, in particular of the functional GAA polypeptide.

In a particular embodiment, the one or more heterologous moieties are attached to the peptide of interest via a linker. The linker which connects the one or more heterologous moieties to the sequence of the peptide of interest can be a covalent bond or a peptide bond. Any conventional linker leading to a correct folding of the chimeric polypeptide may be used. In particular, any linker able to introduce flexibility between the linked domains of the polypeptide may be used. In a particular embodiment, the linker is a Glycine-rich linker.

According to a particular embodiment, the linker may be any linker described in Chichili et al, Protein Sci. 2013 February; 22(2):153-67.

In a particular embodiment, the linker has an amino acid sequence selected in the group consisting of:

```
                                    (SEQ ID NO: 65)
"GAP", (SEQ ID NO: 48)
"GGGGSLVPRGSGGGGS", (SEQ ID NO: 49)
"GSGSGS", (SEQ ID NO: 50)
"GGGGSLVPRGSGGGG", (SEQ ID NO: 51)
"GGSGGHMGSGG", (SEQ ID NO: 52)
"GGSGGSGGSGG", (SEQ ID NO: 53)
"GGSGG", (SEQ ID NO: 54)
"GGSGGGGG",
```

```
    -continued
                                    (SEQ ID NO: 55)
"GSGSGSGS", (SEQ ID NO: 56)
"GGGSEGGGSEGGGSEGGG", (SEQ ID NO: 57)
"AAGAATAA", (SEQ ID NO: 58)
"GGGGG", (SEQ ID NO: 59)
"GGSSG", (SEQ ID NO: 60)
"GSGGGTGGGSG", (SEQ ID NO: 61)
"GSGSGSGSGGSG", (SEQ ID NO: 62)
"GSGGSGGSGGSGGS", (SEQ ID NO: 63)
"GSGGSGSGGSGGSG"
or (SEQ ID NO: 64)
"GT".
```

In a preferred embodiment, the heterologous moiety is fused to the peptide of interest via a peptide linker having the amino acid sequence "GAP" (SEQ ID NO: 65).

In particular, the peptide linker is encoded by the nucleotide sequence of SEQ ID NO: 17 or by a nucleotide sequence at least 85% identity, at least 90% identity, at least 92% identity, at least 95% identity, at least 98% identity, at least 99% identity or at least 100% identity to the nucleotide sequence of SEQ ID NO: 17.

Signal Peptide

The chimeric polypeptide of the invention may further comprise a signal peptide. In particular, the chimeric GAA polypeptide encoded by the nucleic acid molecule of the invention may further comprise a signal peptide, such as the natural signal peptide of GAA, or an alternative signal peptide derived from another secreted protein. In the context of the present invention, the signal peptide is not an "heterologous moiety" as defined above.

Thus, the nucleic acid molecule of the invention encodes a chimeric polypeptide comprising:
a peptide of interest as defined above, in particular a functional GAA polypeptide as defined above, fused to:
one or more heterologous moieties as defined above, wherein at least one of the heterologous moieties is a ligand of the Sortilin receptor,
and optionally a signal peptide.

Non-limiting examples of such signal peptides include those described in the WO2018/046775 patent application. In particular, the signal peptide may be selected from the group consisting of SEQ ID NO: 18 to 22. The invention thereby provides a chimeric GAA polypeptide comprising a signal moiety, one or more heterologous moieties and a peptide of interest such as a functional GAA polypeptide as defined above. In a particular embodiment, the signal peptide is the natural signal peptide of a GAA, such as the signal peptide of hGAA shown in SEQ ID NO: 18. In another embodiment, the signal peptide is an exogenous (or alternative) signal peptide, derived from a protein different from GAA. In a particular embodiment, the alternative signal peptide is selected in the group consisting of SEQ ID NO: 19, 20, 21 and 22, or a functional derivative thereof as defined below. In particular, the signal peptide is selected in the group consisting of SEQ ID NO: 20, 21 and 22, or a functional derivative thereof as defined below.

Particular exogenous signal peptides workable in the present invention include amino acids 1-20 from chymotrypsinogen B2 (SEQ ID NO:21), the signal peptide of human alpha-1-antitrypsin (SEQ ID NO:19), amino acids 1-25 from iduronate-2-sulphatase (SEQ ID NO:20), and amino acids 1-23 from protease C1 inhibitor (SEQ ID NO:22). The signal peptides of SEQ ID NO: 18 and SEQ ID NO: 19 to SEQ ID NO: 22, allow higher secretion of the chimeric GAA polypeptide both in vitro and in vivo when compared to the chimeric GAA comprising its natural signal peptide. In a particular embodiment, the signal peptide has the sequence shown in SEQ ID NO: 18 to 22, or is a functional derivative thereof, i.e. a sequence comprising from 1 to 5, in particular from 1 to 4, in particular from 1 to 3, more particularly from 1 to 2, in particular 1 amino acid deletion(s), insertion(s) or substitution(s) as compared to the sequences shown in SEQ ID NO: 18 to 22, as long as the resulting sequence corresponds to a functional signal peptide, i.e. a signal peptide that allows secretion of a GAA protein.

In a particular embodiment, the signal peptide sequence has at least 85 percent, more preferably at least 90 percent, and even more preferably at least 92 percent identity, in particular at least 95 percent identity, for example at least 98, 99 or has 100 percent identity to a sequence selected in the group consisting of SEQ ID NO: 18 to 22, preferably to a sequence selected in the group consisting of SEQ ID NO: 19 to 22, more preferably to a sequence selected in the group consisting of SEQ ID NO: 20 to 22, even more preferably to the sequence of SEQ ID NO:21. In a particular embodiment, the signal peptide sequence consists of a sequence selected in the group consisting of SEQ ID NO: 18 to 22. Preferably, the signal peptide sequence consists of a sequence selected in the group consisting of SEQ ID NO: 19 to 22, more preferably the signal peptide sequence consists of a sequence selected in the group consisting of SEQ ID NO: 20 to 22. According to a preferred embodiment, the signal peptide sequence consists of the sequence has shown in SEQ ID NO:21.

In a particular embodiment, the nucleic acid molecule encodes a chimeric GAA polypeptide comprising, preferably in this order: a signal peptide as defined above, a heterologous moiety as defined above, optionally a linker as defined above, and a functional GAA polypeptide as defined above. In particular, the chimeric GAA polypeptide comprises, preferably in this order: the signal peptide consisting of the sequence as shown in SEQ ID NO: 21, a heterologous moiety consisting of the sequence as shown in SEQ ID NO:31-33 optionally a linker of the sequence "GAP", and a functional GAA polypeptide consisting of the sequence as shown in SEQ ID NO:9.

In a particular embodiment, the nucleic acid molecule encodes a chimeric GAA polypeptide comprising or consisting of SEQ ID NO: 35-37, or a functional derivative thereof having at least 90% identity, in particular at least 95%, at least 96%, at least 97%, at least 98%, or at least 99% identity to the sequence shown in SEQ ID NO:35-37.

In a particular embodiment, the nucleic acid molecule of the invention comprises or consists of the sequence SEQ ID NO:38 to 40, or a sequence having at least 90% identity, in particular at least 95%, at least 96%, at least 97%, at least 98%, or at least 99% identity to the sequence shown in SEQ ID NO:38-40.

2—Nucleic Acid Construct

The invention also relates to a nucleic acid construct comprising the nucleic acid molecule of the invention. The nucleic acid construct may correspond to an expression cassette comprising the nucleic acid sequence of the invention, operably linked to one or more expression control sequences and/or other sequences improving the expression of a transgene and/or sequences enhancing the secretion of the encoded protein and/or sequences enhancing the uptake of the encoded protein. As used herein, the term "operably linked" refers to a linkage of polynucleotide elements in a functional relationship. A nucleic acid is "operably linked" when it is placed into a functional relationship with another nucleic acid sequence. For instance, a promoter, or another transcription regulatory sequence, is operably linked to a coding sequence if it affects the transcription of the coding sequence. Such expression control sequences are known in the art, such as promoters, enhancers (such as cis-regulatory modules (CRM)), introns, polyA signals, etc.

In particular, the expression cassette may include a promoter. The promoter may be an ubiquitous or tissue-specific promoter, in particular a promoter able to promote expression in cells or tissues in which expression of the peptide of interest is desirable such as in cells or tissues in which the expression of the peptide of interest is desirable. When the peptide of interest is GAA, the promoter may be any promoter able to promote GAA expression in cells or tissues in which expression of the peptide of interest is desirable in GAA-deficient patients. In a particular embodiment, the promoter is a promoter specific to the CNS, in particular to the brain. In a particular embodiment, the promoter is a liver-specific promoter such as the alpha-1 antitrypsin promoter (hAAT) (SEQ ID NO: 23), the transthyretin promoter, the albumin promoter, the thyroxine-binding globulin (TBG) promoter, the LSP promoter (comprising a thyroid hormone-binding globulin promoter sequence, two copies of an alpha1-microglobulin/bikunin enhancer sequence, and a leader sequence—34.Ill, C. R., et al. (1997). Optimization of the human factor VIII complementary DNA expression plasmid for gene therapy of hemophilia A. Blood Coag. Fibrinol. 8: S23-S30.), etc. Other useful liver-specific promoters are known in the art, for example those listed in the Liver Specific Gene Promoter Database compiled the Cold Spring Harbor Laboratory (see World Wide Web: rulai.cshl.edu/LSPD/). In a particular embodiment, the promoter is the hAAT promoter. In another embodiment, the promoter is a promoter directing expression in one tissue or cell of interest (such as in muscle cells), and in liver cells. For example, to some extent, promoters specific of muscle cells such as the desmin, Spc5-12 and MCK promoters may present some leakage of expression into liver cells, which can be advantageous to induce immune tolerance of the subject to the chimeric GAA protein expressed from the nucleic acid molecule.

Other tissue-specific or non-tissue-specific promoters may be useful in the practice of the invention. For example, the expression cassette may include a tissue-specific promoter which is a promoter different from a liver specific promoter. For example the promoter may be muscle-specific, such as the desmin promoter (and a desmin promoter variant such as a desmin promoter including natural or artificial enhancers), the SPc5-12 or the MCK promoter. In another embodiment, the promoter is a promoter specific of other cell lineage, such as the erythropoietin promoter, for the expression of the chimeric polypeptide from cells of the erythroid lineage.

In another embodiment, the promoter is an ubiquitous promoter. Representative ubiquitous promoters include the cytomegalovirus enhancer/chicken beta actin (CAG) promoter, the cytomegalovirus enhancer/promoter (CMV), the PGK promoter, the SV40 early promoter, etc. In addition, the promoter may also be an endogenous promoter such as the albumin promoter or the GAA promoter. In a particular embodiment, the promoter is any hybrid regulatory element as described in patent application PCT/EP2019/053061, including the specific promoters referred as "LiMP" and "LiNeuP".

In a particular embodiment, the promoter is any hybrid promoter as described in patent application EP19 305455.8 herein incorporated by reference, wherein said hybrid promoter comprises one or a plurality of liver-selective enhancer(s) operably linked to a muscle-selective promoter. In particular, the promoter may be the specific promoter referred as EP1, EP2, EP3 or EP4 in patent application EP19 305455.8, in particular the promoter referred to as EP4.

In a particular embodiment, the promoter is associated to an enhancer sequence, such as a cis-regulatory module (CRMs) or an artificial enhancer sequence. For example, the promoter may be associated to an enhancer sequence such as the human ApoE control region (or Human apolipoprotein E/C-I gene locus, hepatic control region HCR-1—Genbank accession No. U32510, shown in SEQ ID NO:24). In a particular embodiment, an enhancer sequence such as the ApoE sequence is associated to a liver-specific promoter such as those listed above, and in particular such as the hAAT promoter. Other CRMs useful in the practice of the present invention include those described in Rincon et al., Mol Ther. 2015 January; 23(1):43-52, Chuah et al., Mol Ther. 2014 September; 22(9):1605-13 or Nair et al., Blood. 2014 May 15; 123(20):3195-9.

In another particular embodiment, the nucleic acid construct comprises an intron, in particular an intron placed between the promoter and the nucleic acid molecule of the invention encoding the chimeric polypeptide. An intron may be introduced to increase mRNA stability and the production of the protein. In a further embodiment, the nucleic acid construct comprises a human beta globin b2 (or HBB2) intron, a coagulation factor IX (FIX) intron, a SV40 intron or a chicken beta-globin intron. In another further embodiment, the nucleic acid construct of the invention contains a modified intron (in particular a modified HBB2 or FIX intron) designed to decrease the number of, or even totally remove, alternative open reading frames (ARFs) found in said intron. Preferably, ARFs are removed whose length spans over 50 bp and have a stop codon in frame with a start codon. ARFs may be removed by modifying the sequence of the intron. For example, modification may be carried out by way of nucleotide substitution, insertion or deletion, preferably by nucleotide substitution. As an illustration, one or more nucleotides, in particular one nucleotide, in an ATG or GTG start codon present in the sequence of the intron of interest may be replaced resulting in a non-start codon. For example, an ATG or a GTG may be replaced by a CTG, which is not a start codon, within the sequence of the intron of interest.

The classical HBB2 intron used in nucleic acid constructs is shown in SEQ ID NO: 25. For example, this HBB2 intron may be modified by eliminating start codons (ATG and GTG codons) within said intron. In a particular embodiment, the modified HBB2 intron comprised in the construct has the sequence shown in SEQ ID NO: 26. The classical FIX intron used in nucleic acid constructs is derived from the first intron of human FIX and is shown in SEQ ID NO: 27. FIX intron may be modified by eliminating start codons (ATG and GTG codons) within said intron. In a particular embodiment, the modified FIX intron comprised in the construct of the invention has the sequence shown in SEQ ID NO: 28. The classical chicken-beta globin intron used in nucleic acid constructs is shown in SEQ ID NO: 29. Chicken-beta globin intron may be modified by eliminating start codons (ATG and GTG codons) within said intron. In a particular embodiment, the modified chicken-beta globin intron comprised in the construct of the invention has the sequence shown in SEQ ID NO: 30.

The inventors have previously shown in WO2015/162302 that such a modified intron, in particular a modified HBB2 or FIX intron, has advantageous properties and can significantly improve the expression of a transgene.

In a particular embodiment, the nucleic acid construct of the invention is an expression cassette comprising, in the 5' to 3' orientation, a promoter optionally preceded by an enhancer, the nucleic acid molecule of the invention (i.e. the sequence encoding the chimeric polypeptide of the invention), and a polyadenylation signal (such as the bovine growth hormone polyadenylation signal, the SV40 polyadenylation signal, or another naturally occurring or artificial polyadenylation signal). In a particular embodiment, the nucleic acid construct of the invention is an expression cassette comprising, in the 5' to 3' orientation, a promoter optionally preceded by an enhancer, (such as the ApoE control region), an intron (in particular an intron as defined above), the nucleic acid molecule of the invention, and a polyadenylation signal. In a further particular embodiment, the nucleic acid construct of the invention is an expression cassette comprising, in the 5' to 3' orientation, an enhancer such as the ApoE control region, a promoter, an intron (in particular an intron as defined above), the nucleic acid molecule of the invention, and a polyadenylation signal. In a further particular embodiment of the invention the expression cassette comprising, in the 5' to 3' orientation, an ApoE control region, the hAAT-liver specific promoter, a HBB2 intron (in particular a modified HBB2 intron as defined above), the nucleic acid molecule of the invention, and the bovine growth hormone polyadenylation signal, such as the nucleic acid construct shown in SEQ ID NO:41-43, which includes the nucleic acid molecule of SEQ ID NO:38-40 encoding a chimeric GAA polypeptide.

In a particular embodiment, the expression cassette comprises the ApoE control region, the hAAT-liver specific promoter, a codon-optimized HBB2 intron, the sequence of the nucleic acid molecule of the invention and the bovine growth hormone polyadenylation signal.

In designing the nucleic acid construct of the invention, one skilled in the art will take care of respecting the size limit of the vector used for delivering said construct to a cell or organ. In particular, one skilled in the art knows that a major limitation of AAV vector is its cargo capacity which may vary from one AAV serotype to another but is thought to be limited to around the size of parental viral genome. For example, 5 kb is the maximum size usually thought to be packaged into an AAV8 capsid. (Wu Z. et al., Mol Ther., 2010, 18(1): 80-86; Lai Y. et al., Mol Ther., 2010, 18(1): 75-79; Wang Y. et al., Hum Gene Ther Methods, 2012, 23(4): 225-33). Accordingly, those skilled in the art will take care in practicing the present invention to select the components of the nucleic acid construct of the invention so that the resulting nucleic acid sequence, including sequences coding AAV 5'- and 3'-ITRs to preferably not exceed 110% of the cargo capacity of the AAV vector implemented, in particular to preferably not exceed 5.5 kb.

3—Vector

The invention also relates to a vector comprising a nucleic acid molecule or construct as disclosed herein. In particular, the vector of the invention is a vector suitable for protein expression, preferably for use in gene therapy. In one embodiment, the vector is a plasmid vector. In another embodiment, the vector is a nanoparticle containing a nucleic acid molecule of the invention, in particular a messenger RNA encoding the chimeric polypeptide of the invention. In another embodiment, the vector is a system based on transposons, allowing integration of the nucleic acid molecule or construct of the invention in the genome of the target cell, such as the hyperactive Sleeping Beauty (SB100X) transposon system (Mates et al. 2009). In another embodiment, the vector is a viral vector suitable for gene therapy, targeting any cell of interest such as liver tissue or cells, muscle cell, CNS cells (such as brain cells), or hematopoietic stem cells such as cells of the erythroid lineage (such as erythrocytes). In this case, the nucleic acid construct of the invention also contains sequences suitable for producing an efficient viral vector, as is well known in the art. In a particular embodiment, the viral vector is derived from an integrating virus. In particular, the viral vector may be derived from a retrovirus or a lentivirus. In a further particular embodiment, the viral vector is an AAV vector, such as an AAV vector suitable for transducing liver tissues or cells, more particularly an AAV-1, -2 and AAV-2 variants (such as the quadruple-mutant capsid optimized AAV-2 comprising an engineered capsid with Y44+500+730F+T491V changes, disclosed in Ling et al., 2016 Jul. 18, Hum Gene Ther Methods. [Epub ahead of print]), -3 and AAV-3 variants (such as the AAV3-ST variant comprising an engineered AAV3 capsid with two amino acid changes, S663V+T492V, disclosed in Vercauteren et al., 2016, Mol. Ther. Vol. 24(6), p. 1042), -3B and AAV-3B variants, -4, -5, -6 and AAV-6 variants (such as the AAV6 variant comprising the triply mutated AAV6 capsid Y731F/Y705F/T492V form disclosed in Rosario et al., 2016, Mol Ther Methods Clin Dev. 3, p. 16026), -7, -8, -9, -10 such as -cy10 and -rh10, -rh74, -dj, Anc80, LK03, AAV2i8, porcine AAV serotypes such as AAVpo4 and AAVpo6, etc., vector or a retroviral vector such as a lentiviral vector and an alpha-retrovirus. As is known in the art, depending on the specific viral vector considered for use, additional suitable sequences will be introduced in the nucleic acid construct of the invention for obtaining a functional viral vector. Suitable sequences include AAV ITRs for an AAV vector, or LTRs for lentiviral vectors. As such, the invention also relates to an expression cassette as described above, flanked by an ITR or an LTR on each side.

Advantages of viral vectors are discussed in the following part of this disclosure. Viral vectors are preferred for delivering the nucleic acid molecule or construct of the invention, such as a retroviral vector, for example a lentiviral vector, or a non-pathogenic parvovirus, more preferably an AAV vector. The human parvovirus Adeno-Associated Virus (AAV) is a dependovirus that is naturally defective for replication which is able to integrate into the genome of the infected cell to establish a latent infection. The last property appears to be unique among mammalian viruses because the integration occurs at a specific site in the human genome, called AAVS1, located on chromosome 19 (19q13.3-qter).

Therefore, AAV vectors have arisen considerable interest as potential vectors for human gene therapy. Among the favorable properties of the virus are its lack of association with any human disease, its ability to infect both dividing and non-dividing cells, and the wide range of cell lines derived from different tissues that can be infected.

Among the serotypes of AAVs isolated from human or non-human primates (NHP) and well characterized, human serotype 2 is the first AAV that was developed as a gene transfer vector. Other currently used AAV serotypes include AAV-1, AAV-2 variants (such as the quadruple-mutant capsid optimized AAV-2 comprising an engineered capsid with Y44+500+730F+T491V changes, disclosed in Ling et al., 2016 Jul. 18, Hum Gene Ther Methods. [Epub ahead of print]), -3 and AAV-3 variants (such as the AAV3-ST variant comprising an engineered AAV3 capsid with two amino acid changes, S663V+T492V, disclosed in Vercauteren et al., 2016, Mol. Ther. Vol. 24(6), p. 1042), -3B and AAV-3B variants, -4, -5, -6 and AAV-6 variants (such as the AAV6 variant comprising the triply mutated AAV6 capsid Y731F/Y705F/T492V form disclosed in Rosario et al., 2016, Mol Ther Methods Clin Dev. 3, p. 16026), -7, -8, -9, -10 such as cy10 and -rh10, -rh74, -dj, Anc80, LK03, AAV2i8, porcine AAV serotypes such as AAVpo4 and AAVpo6, and tyrosine, lysine and serine capsid mutants of the AAV serotypes, etc. In addition, other non-natural engineered variants and chimeric AAV can also be useful.

AAV viruses may be engineered using conventional molecular biology techniques, making it possible to optimize these particles for cell specific delivery of nucleic acid sequences, for minimizing immunogenicity, for tuning stability and particle lifetime, for efficient degradation, for accurate delivery to the nucleus.

Desirable AAV fragments for assembly into vectors include the cap proteins, including the vp1, vp2, vp3 and hypervariable regions, the rep proteins, including rep 78, rep 68, rep 52, and rep 40, and the sequences encoding these proteins. These fragments may be readily utilized in a variety of vector systems and host cells.

AAV-based recombinant vectors lacking the Rep protein integrate with low efficacy into the host's genome and are mainly present as stable circular episomes that can persist for years in the target cells. Alternatively to using AAV natural serotypes, artificial AAV serotypes may be used in the context of the present invention, including, without limitation, AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid. Accordingly, the present invention relates to an AAV vector comprising the nucleic acid molecule or construct of the invention. In the context of the present invention, the AAV vector comprises an AAV capsid able to transduce the target cells of interest, in particular hepatocytes. According to a particular embodiment, the AAV vector is of the AAV-1, -2, AAV-2 variants (such as the quadruple-mutant capsid optimized AAV-2 comprising an engineered capsid with Y44+500+730F+T491V changes, disclosed in Ling et al., 2016 Jul. 18, Hum Gene Ther Methods. [Epub ahead of print]), -3 and AAV-3 variants (such as the AAV3-ST variant comprising an engineered AAV3 capsid with two amino acid changes, S663V+T492V, disclosed in Vercauteren et al., 2016, Mol. Ther. Vol. 24(6), p. 1042), -3B and AAV-3B variants, -4, -5, -6 and AAV-6 variants (such as the AAV6 variant comprising the triply mutated AAV6 capsid Y731F/Y705F/T492V form disclosed in Rosario et al., 2016, Mol Ther Methods Clin Dev. 3, p. 16026), -7, -8, -9, -10 such as -cy10 and -rh10, -rh74, -dj, Anc80, LK03, AAV2i8, porcine AAV such as AAVpo4 and AAVpo6, and tyrosine, lysine and serine capsid mutants of a AAV serotypes, etc., serotype. In a particular embodiment, the AAV vector is of the AAV8, AAV9, AAVrh74 or AAV2i8 serotype (i.e. the AAV vector has a capsid of the AAV8, AAV9, AAVrh74 or AAV2i8 serotype). In a further particular embodiment, the AAV vector is a pseudotyped vector, i.e. its genome and capsid are derived from AAVs of different serotypes. For example, the pseudotyped AAV vector may be a vector whose genome is derived from one of the above mentioned AAV serotypes, and whose capsid is derived from another serotype. For example, the genome of the pseudotyped vector may have a capsid derived from the AAV8, AAV9, AAVrh74 or AAV2i8 serotype, and its genome may be derived from and different serotype. In a particular embodiment, the AAV vector has a capsid of the AAV8, AAV9 or AAVrh74 serotype, in particular of the AAV8 or AAV9 serotype, more particularly of the AAV8 serotype.

In a specific embodiment, wherein the vector is for use in delivering the transgene to muscle cells, the AAV vector may be selected, among others, in the group consisting of AAV8, AAV9 and AAVrh74. In another specific embodiment, wherein the vector is for use in delivering the transgene to liver cells, the AAV vector may be selected, among others, in the group consisting of AAVS, AAV8, AAV9, AAV-LK03, AAV-Anc80 and AAV3B.

In another embodiment, the capsid is a modified capsid. In the context of the present invention, a "modified capsid" may be a chimeric capsid or capsid comprising one or more variant VP capsid proteins derived from one or more wild-type AAV VP capsid proteins.

In a particular embodiment, the AAV vector is a chimeric vector, i.e. its capsid comprises VP capsid proteins derived from at least two different AAV serotypes, or comprises at least one chimeric VP protein combining VP protein regions or domains derived from at least two AAV serotypes. Examples of such chimeric AAV vectors useful to transduce liver cells are described in Shen et al., Molecular Therapy, 2007 and in Tenney et al., Virology, 2014. For example a chimeric AAV vector can derive from the combination of an AAV8 capsid sequence with a sequence of an AAV serotype different from the AAV8 serotype, such as any of those specifically mentioned above. In another embodiment, the capsid of the AAV vector comprises one or more variant VP capsid proteins such as those described in WO2015013313, in particular the RHM4-1, RHM15-1, RHM15-2, RHM15-3/RHM15-5, RHM15-4 and RHM15-6 capsid variants, which present a high liver tropism.

In another embodiment, the modified capsid can be derived also from capsid modifications inserted by error prone PCR and/or peptide insertion (e.g. as described in Bartel et al., 2011). In addition, capsid variants may include single amino acid changes such as tyrosine mutants (e.g. as described in Zhong et al., 2008).

In addition, the genome of the AAV vector may either be a single stranded or self-complementary double-stranded genome (McCarty et al., Gene Therapy, 2003). Self-complementary double-stranded AAV vectors are generated by deleting the terminal resolution site (trs) from one of the AAV terminal repeats. These modified vectors, whose replicating genome is half the length of the wild type AAV genome have the tendency to package DNA dimers. In a preferred embodiment, the AAV vector implemented in the practice of the present invention has a single stranded genome, and further preferably comprises an AAV8, AAV9, AAVrh74 or AAV2i8 capsid, in particular an AAV8, AAV9 or AAVrh74 capsid, such as an AAV8 or AAV9 capsid, more particularly an AAV8 capsid.

In a particular embodiment, the invention relates to an AAV vector comprising, in a single-stranded or double-stranded, self-complementary genome (e.g. a single-stranded genome), the nucleic acid construct of the invention. In one embodiment, the AAV vector comprises an AAV8, AAV9, AAVrh74 or AAV2i8 capsid, in particular an AAV8, AAV9 or AAVrh74 capsid, such as an AAV8 or AAV9 capsid, more particularly an AAV8 capsid. In a further particular embodiment, said nucleic acid is operably linked to a promoter, especially an ubiquitous or liver-specific promoter. According to a specific variant embodiment, the promoter is an ubiquitous promoter such as the cytomegalovirus enhancer/chicken beta actin (CAG) promoter, the cytomegalovirus enhancer/promoter (CMV), the PGK promoter and the SV40 early promoter. In a specific variant, the ubiquitous promoter is the CAG promoter. According to another variant, the promoter is a liver-specific promoter such as the alpha-1 antitrypsin promoter (hAAT), the transthyretin promoter, the albumin promoter and the thyroxine-binding globulin (TBG) promoter. In a specific variant, the liver-specific promoter is the hAAT liver-specific promoter of SEQ ID NO: 23. In a further particular embodiment, the nucleic acid construct comprised into the genome of the AAV vector of the invention further comprises an intron as described above, such as an intron placed between the promoter and the nucleic acid sequence encoding the chimeric polypeptide of the invention. Representative introns that may be included within the nucleic acid construct introduced within the AAV vector genome include, without limitation, the human beta globin b2 (or HBB2) intron, the FIX intron and the chicken beta-globin intron. Said intron within the genome of the AAV vector may be a classical (or unmodified) intron or a modified intron designed to decrease the number of, or even totally remove, alternative open reading frames (ARFs) within said intron. Modified and unmodified introns that may be used in the practice of this embodiment where the nucleic acid of the invention is introduced within an AAV vector are thoroughly described above. In a particular embodiment, the AAV vector, in particular an AAV vector comprising an AAV8, AAV9, AAVrh74 or AAV2i8 capsid, in particular an AAV8, AAV9 or AAVrh74 capsid, such as an AAV8 or AAV9 capsid, more particularly an AAV8 capsid, of the invention includes within its genome a modified (or optimized) intron such as the modified HBB2 intron of SEQ ID NO: 26, the modified FIX intron of SEQ ID NO: 28 and the modified chicken beta-globin intron of SEQ ID NO: 30. In a further particular embodiment, the vector of the invention is an AAV vector comprising comprises an AAV8, AAV9, AAVrh74 or AAV2i8 capsid, in particular an AAV8, AAV9 or AAVrh74 capsid, such as an AAV8 or AAV9 capsid, more particularly an AAV8 capsid, comprising a genome containing, in the 5' to 3' orientation: an AAV 5'-ITR (such as an AAV2 5'-ITR); an ApoE control region; the hAAT-liver specific promoter; a HBB2 intron (in particular a modified HBB2 intron as defined above); the nucleic acid molecule of the invention encoding the chimeric polypeptide, in particular the chimeric GAA polypeptide; the bovine growth hormone polyadenylation signal; and an AAV 3'-ITR (such as an AAV2 3'-ITR), such as a genome comprising a the nucleic acid construct shown in SEQ ID NO: 41-43-Z flanked by an AAV 5'-ITR (such as an AAV2 5'-ITR) and an AAV 3'-ITR (such as an AAV2 3'-ITR).

In a particular embodiment of the invention, the nucleic acid construct of the invention comprises a liver-specific promoter as described above, and the vector is a viral vector capable of transducing liver tissue or cells as described above. The protolerogenic and metabolic properties of the liver are advantageously implemented thanks to this embodiment to develop highly efficient and optimized vectors to express secretable forms of GAA in hepatocytes and to induce immune tolerance to the protein.

In addition, in a further particular embodiment, the invention provides the combination of two vectors, such as two viral vectors, in particular two AAV vectors, for improving gene delivery and treatment efficacy in the cells of interest. For example, the two vectors may carry the nucleic acid molecule of the invention coding for the chimeric polypeptide of the invention, under the control of one different promoter in each of these two vectors. In a particular embodiment, one vector comprises a promoter which is a liver-specific promoter (as one of those described above), and the other vector comprises a promoter which is specific of another tissue of interest for the treatment of a glycogen storage disorder, such as a muscle-specific promoter, for example the desmin promoter. In a particular variant of this embodiment, this combination of vectors corresponds to multiple co-packaged AAV vectors produced as described in WO2015196179.

4—Chimeric GAA Polypeptide

In another aspect, the invention provides a chimeric polypeptide, encoded by the nucleic acid molecule of the invention as described above. In particular, the chimeric polypeptide is a chimeric GAA polypeptide comprising a functional GAA polypeptide fused to one or more heterologous domains, wherein at least one of the heterologous domain is the ligand of the Sortilin receptor as defined above. In a particular embodiment, the chimeric GAA polypeptide has the sequence shown in SEQ ID NO:35-37, or is a functional derivative thereof having at least 90% identity, in particular at least 95%, at least 96%, at least 97%, at least 98%, or at least 99% identity to the sequence shown in SEQ ID NO:35-37.

In a particular embodiment, the chimeric polypeptide, in particular the chimeric GAA polypeptide, is able to reduce glycogen content in the CNS (such as spinal cord and brain), in particular in the brain. In a particular embodiment, the chimeric polypeptide, in particular the chimeric GAA polypeptide leads to an improved reduction of the glycogen content in the CNS (such as spinal cord and brain), in particular in the brain, when compared to a non-chimeric polypeptide, in particular a non-chimeric GAA polypeptide, that is not fused to one or more heterologous domains as described above.

5—Cell

The invention also relates to an isolated cell, for example a liver cell, that is transformed with a nucleic acid molecule or construct of the invention as is the case for ex vivo gene therapy. Thus, the invention relates to an isolated cell, for example a liver cell, that comprises the nucleic acid molecule, the nucleic acid construct or the vector of the invention.

Cells of the invention may be delivered to the subject in need thereof, such as GAA-deficient patient, by any appropriate administration route such as via injection in the liver or in the bloodstream of said subject. In a particular embodiment, the invention involves introducing the nucleic acid of the invention into liver cells, in particular into liver cells of the subject to be treated, and administering said transformed liver cells into which the nucleic acid has been introduced to the subject. Advantageously, this embodiment is useful for secreting GAA from said cells. In a particular embodiment, the liver cells are liver cells from the patient to be treated, or are liver stem cells that are further transformed, and differentiated in vitro into liver cells, for subsequent administration to the patient.

The present invention further relates to a transgenic, nonhuman animal comprising in its genome the nucleic acid molecule or construct of the invention encoding the chimeric polypeptide according to the invention. In a particular embodiment, the animal is a mouse.

Apart from the specific delivery systems embodied below in the examples, various delivery systems are known and can be used to administer the nucleic acid molecule or construct of the invention, e.g., encapsulation in liposomes, microparticles, microcapsules, recombinant cells capable of expressing the nucleic acid sequence of the invention, receptor-mediated endocytosis, construction of a therapeutic nucleic acid as part of a retroviral or other vector, etc.

According to an embodiment, it may be desirable to introduce the chimeric polypeptide, nucleic acid molecule, nucleic acid construct or the isolated cell of the invention into the liver of the subject by any suitable route. In addition naked DNA such as minicircles and transposons can be used for delivery or lentiviral vectors. Additionally, gene editing technologies such as zinc finger nucleases, meganucleases, TALENs, and CRISPR can also be used to deliver the coding sequence of the invention.

6—Pharmaceutical Composition

The present invention also provides pharmaceutical compositions comprising the nucleic acid molecule, the nucleic acid construct, the vector, the chimeric polypeptide, or the isolated cell of the invention. Such compositions comprise a therapeutically effective amount of the therapeutic (the nucleic acid molecule, the nucleic acid construct, the vector, the chimeric polypeptide or the cell of the invention), and a pharmaceutically acceptable carrier. In a specific embodiment, the term "pharmaceutically acceptable" means approved by a regulatory agency of the Federal or a state government or listed in the U.S. or European Pharmacopeia or other generally recognized pharmacopeia for use in animals, and humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsions, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the subject. In a particular embodiment, the nucleic acid, vector or cell of the invention is formulated in a composition comprising phosphate-buffered saline and supplemented with 0.25% human serum albumin. In another particular embodiment, the nucleic acid, vector or cell of the invention is formulated in a composition comprising ringer lactate and a non-ionic surfactant, such as pluronic F68 at a final concentration of 0.01-0.0001%, such as at a concentration of 0.001%, by weight of the total composition. The formulation may further comprise serum albumin, in particular human serum albumin, such as human serum albumin at 0.25%. Other appropriate formulations for either storage or administration are known in the art, in particular from WO 2005/118792 or Allay et al., 2011.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to, ease pain at the, site of the injection.

7—Administration and Use

In an embodiment, the nucleic acid molecule, the nucleic acid construct, the vector, the chimeric polypeptide or the cell of the invention can be delivered in a vesicle, in particular a liposome. In yet another embodiment, the nucleic acid molecule, the nucleic acid construct, the vector, the chimeric polypeptide or the cell of the invention can be delivered in a controlled release system.

Methods of administration of the nucleic acid molecule, the nucleic acid construct, the vector, the chimeric polypeptide or the cell of the invention include but are not limited to intradermal, intramuscular, intraperitoneal, intravenous, subcutaneous, intranasal, epidural, and oral routes. In a particular embodiment, the administration is via the intravenous or intramuscular route. The nucleic acid molecule, the nucleic acid construct, the vector, the chimeric polypeptide or the cell of the invention, whether vectorized or not, may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the pharmaceutical compositions of the invention locally to the area in need of treatment, e.g. the liver. This may be achieved, for example, by means of an implant, said implant being of a porous, nonporous, or gelatinous material, including membranes, such as sialastic membranes, or fibers.

The amount of the therapeutic of the invention (i.e. the nucleic acid molecule, the nucleic acid construct, the vector, the chimeric polypeptide or the isolated cell of the invention) which will be effective in the treatment of a disease, in particular a glycogen storage disease can be determined by standard clinical techniques. In addition, in vivo and/or in vitro assays may optionally be employed to help predict optimal dosage ranges. The precise dose to be employed in the formulation will also depend on the route of administration, and the seriousness of the disease, and should be decided according to the judgment of the practitioner and each patient's circumstances. The dosage of the nucleic acid molecule, the nucleic acid construct, the vector, the chimeric polypeptide or the cell of the invention administered to the subject in need thereof will vary based on several factors including, without limitation, the route of administration, the specific disease treated, the subject's age or the level of expression necessary to obtain the therapeutic effect. One skilled in the art can readily determine, based on its knowledge in this field, the dosage range required based on these factors and others. In case of a treatment comprising administering a viral vector, such as an AAV vector, to the subject, typical doses of the vector are of at least $1 \times 10^8$ vector genomes per kilogram body weight (vg/kg), such as at least $1 \times 10^9$ vg/kg, at least $1 \times 10^{10}$ vg/kg, at least $1 \times 10^{11}$ vg/kg, at least $1 \times 10^{12}$ vg/kg at least $1 \times 10^{13}$ vg/kg, or at least $1 \times 10^{14}$ vg/kg.

The invention further relates to a method for treating a lysosomal storage disease, which comprises a step of delivering a therapeutic effective amount of the nucleic acid, the vector, the chimeric polypeptide, the pharmaceutical composition or the cell of the invention to a subject in need thereof.

In a particular embodiment, the lysosomal disease is associated with neurological manifestations.

In particular, the lysosomal disease can be a glycogen storage disease (GSD) such as Pompe disease, a mucopolysaccharidosis type I (MPSI), a mucopolysaccharidosis type II (MPSII), a mucopolysaccharidosis type IIIA (MPSIIIA), a mucopolysaccharidosis type IIIB (MPSIIIB), a mucopolysaccharidosis type IIIC (MPSIIIC), a mucopolysaccharidosis type IIID (MPSIIID), a mucopolysaccharidosis type VII (MPSVII), a metachromatic leukodystrophy (MLD), Gaucher's disease type 2, Gaucher's disease type 3, GM1 gangliosidosis, Tay-Sachs disease, Sandhoff's disease, Fabry's disease, Krabbe's disease, Niemann-Pick Type A, Metachromatic leukodystrophy, Farber's disease, α-Mannosidosis, β-Mannosidosis, Schindler disease, Sialidosis, Neuronal ceroid-lipofuscinosis type 1 (NCL1), Neuronal ceroid-lipofuscinosis type 2 (NCL2), multiple sulfatase deficiency (MSD), Mucolipidosis type II, Mucolipidosis type IIIA, Galactosialidosis, Niemann-Pick type C, GM2 activator protein deficiency, Danon disease, Salla disease, NCL3 disease, or Mucolipidosis type IV.

In a particular embodiment the disease is a glycogen storage disease, in particular GSDII (Pompe disease).

The invention also relates to a method for reducing glycogen content in the CNS (such as in the spinal cord and/or the brain), in particular in the brain, which comprises a step of delivering a therapeutic effective amount of the nucleic acid, the vector, the chimeric polypeptide, the pharmaceutical composition or the cell of the invention to a subject in need thereof.

In a particular embodiment, the invention relates to a method for treating a glycogen storage disease, which comprises a step of delivering a therapeutic effective amount of the nucleic acid, the vector, the chimeric GAA polypeptide, the pharmaceutical composition or the cell of the invention to a subject in need thereof.

The invention also relates to a method for treating a glycogen storage disease, said method inducing no immune response to the transgene (i.e. to the chimeric GAA polypeptide), or inducing a reduced immune response to the transgene, comprising a step of delivering a therapeutic effective amount of the nucleic acid molecule, nucleic acid construct, chimeric polypeptide, vector, pharmaceutical composition or cell of the invention to a subject in need thereof. The invention also relates to a method for treating a glycogen storage disease, said method comprising repeated administration of a therapeutic effective amount of the nucleic acid molecule, nucleic acid construct, chimeric polypeptide, vector, pharmaceutical composition or cell of the invention to a subject in need thereof. In this aspect, the nucleic acid molecule or the nucleic acid construct of the invention comprises a promoter which is functional in liver cells, thereby allowing immune tolerance to the expressed chimeric GAA polypeptide produced therefrom. As well, in this aspect, the pharmaceutical composition used in this aspect comprises a nucleic acid molecule or nucleic acid construct comprising a promoter which is functional in liver cells. In case of delivery of liver cells, said cells may be cells previously collected from the subject in need of the treatment and that were engineered by introducing therein the nucleic acid molecule or the nucleic acid construct of the invention to thereby make them able to produce the chimeric GAA polypeptide of the invention. According to an embodiment, in the aspect comprising a repeated administration, said administration may be repeated at least once or more, and may even be considered to be done according to a periodic schedule, such as once per week, per month or per year. The periodic schedule may also comprise an administration once every 2, 3, 4, 5, 6, 7, 8, 9 or 10 year, or more than 10 years. In another particular embodiment, administration of each administration of a viral vector of the invention is done using a different virus for each successive administration, thereby avoiding a reduction of efficacy because of a possible immune response against a previously administered viral vector. For example, a first administration of a viral vector comprising an AAV8 capsid may be done, followed by the administration of a vector comprising an AAV9 capsid, or even by the administration of a virus unrelated to AAVs, such as a retroviral or lentiviral vector.

The invention also relates to a method for treating a glycogen storage disease, comprising a step of delivering a therapeutic effective amount of the nucleic acid molecule, nucleic acid construct, vector, chimeric GAA polypeptide, pharmaceutical composition or cell of the invention to a subject in need thereof. The transgene may be used to produce high levels of GAA protein, and provides therapeutic benefits such as improving GAA activity in plasma and/or in tissues such as skeletal muscles. The invention also relates to a method for treating a glycogen storage disease, said method comprising repeated administration of a therapeutic effective amount of the nucleic acid molecule, nucleic acid construct, vector, chimeric GAA polypeptide, pharmaceutical composition or cell of the invention to a subject in need thereof. In this aspect, the nucleic acid molecule or the nucleic acid construct of the invention comprises a promoter which is functional in liver cells, thereby allowing immune tolerance to the expressed chimeric GAA polypeptide produced therefrom. As well, in this aspect, the pharmaceutical composition used in this aspect comprises a nucleic acid molecule or nucleic acid construct comprising a promoter which is functional in liver cells. In case of delivery of liver cells, said cells may be cells previously collected from the subject in need of the treatment and that were engineered by introducing therein the nucleic acid molecule or the nucleic acid construct of the invention to thereby make them able to produce the chimeric GAA polypeptide of the invention. According to an embodiment, in the aspect comprising a repeated administration, said administration may be repeated at least once or more, and may even be considered to be done according to a periodic schedule, such as once per week, per month or per year. The periodic schedule may also comprise an administration once every 2, 3, 4, 5, 6, 7, 8, 9 or 10 year, or more than 10 years. In another particular embodiment, administration of each administration of a viral vector of the invention is done using a different virus for each successive administration, thereby avoiding a reduction of efficacy because of a possible immune response against a previously administered viral vector. For example, a first administration of a viral vector comprising an AAV8 capsid may be done, followed by the administration of a vector comprising an AAV9 capsid, or even by the administration of a virus unrelated to AAVs, such as a retroviral or lentiviral vector.

According to the present invention, a treatment may include curative, alleviation or prophylactic effects. Accordingly, therapeutic and prophylactic treatment includes amelioration of the symptoms of a particular glycogen storage disease or preventing or otherwise reducing the risk of developing a particular glycogen storage disease. The term "prophylactic" may be considered as reducing the severity or the onset of a particular condition. "Prophylactic" also includes preventing reoccurrence of a particular condition in a patient previously diagnosed with the condition. "Therapeutic" may also reduce the severity of an existing condition. The term 'treatment' is used herein to refer to any regimen that can benefit a animal, in particular a mammal, more particularly a human subject.

The invention also relates to an ex vivo gene therapy method for the treatment of a glycogen storage disease, comprising introducing the nucleic acid molecule or the nucleic acid construct of the invention into an isolated cell of a patient in need thereof, for example an isolated hematopoietic stem cell, and introducing said cell into said patient in need thereof. In a particular embodiment of this aspect, the nucleic acid molecule or construct is introduced into the cell with a vector as defined above. In a particular embodiment, the vector is an integrative viral vector. In a further particular embodiment, the viral vector is a retroviral vector, such as a lenviral vector. For example, a lentiviral vector as disclosed in van Til et al., 2010, Blood, 115(26), p. 5329, may be used in the practice in the method of the present invention.

The invention also relates to the nucleic acid molecule, the nucleic acid construct, the vector, the chimeric GAA polypeptide or the cell of the invention for use as a medicament.

The invention also relates to the nucleic acid molecule, the nucleic acid construct, the vector, the chimeric GAA polypeptide or the cell of the invention, for use in a method for treating a disease caused by a mutation in the GAA gene, in particular in a method for treating Pompe disease. The invention further relates to the nucleic acid molecule, the nucleic acid construct, the vector, the chimeric GAA polypeptide or the cell of the invention, for use in a method for treating a glycogen storage disease, such as GSDI (von Gierke's disease), GSDII (Pompe disease), GSDIII (Cori disease), GSDIV, GSDV, GSDVI, GSDVII, GSDVIII and lethal congenital glycogen storage disease of the heart, more particularly GSDI, GSDII or GSDIII, even more particularly GSDII and GSDIII, and most particularly GSDII. The chimeric GAA polypeptide of the invention may be administered to a patient in need thereof, for use in enzyme replacement therapy (ERT), such as for use in enzyme replacement therapy of one of a glycogen storage disease, such as GSDIII (Cori's disease) but also for GSD-IV, —VI, —IX, —XI and cardiac glycogenosis due to AMP-activated protein kinase gamma subunit 2 deficiency.

The invention further relates to the use of the nucleic acid molecule, the nucleic acid construct, the vector, the chimeric GAA polypeptide or the cell of the invention, in the manufacture of a medicament useful for treating a glycogen storage disease, such as GSDI (von Gierke's disease), GSDII (Pompe disease), GSDIII (Cori disease), GSDIV, GSDV, GSDVI, GSDVII, GSDVIII and lethal congenital glycogen storage disease of the heart, more particularly GSDI, GSDII or GSDIII, even more particularly GSDII and GSDIII, and most particularly GSDII.

EXAMPLES

Materials and Methods

GAA Expression Cassettes and AAV Vectors

The GAA transgene expression cassettes used in this study contained the codon-optimized human GAA (hGAA) coding sequence [Puzzo F., et al., Sci Transl Med. 2017 Nov. 29; 9 (418)]. Codon-optimization was performed using a commercial algorithm (Thermo Fisher Scientific) [Puzzo F., et al., Sci Transl Med. 2017 Nov. 29; 9 (418)]. The heterologous domains (Spadin, ApoE, ApoB) were cloned at the N-terminus of the GAA transgene as depicted in FIG. 1. Transgene sequences were cloned into an AAV vector backbone under the transcriptional control of the apolipoprotein E (hepatocyte control region enhancer) and the human alpha 1-antitrypsin (hAAT) promoter. All DNA sequences used in the study were synthetized either by GeneCust or Thermo Fisher Scientific.

AAV vectors used in this study were produced using an adenovirus-free transient transfection method of HEK293 cells as described [Puzzo F, et al. Sci Transl Med. 2017 Nov. 29; 9 (418)]. Titers of AAV vector stocks were determined using quantitative real-time PCR (qPCR) and SDS-PAGE followed by SYPRO Ruby protein gel stain and band densitometry. All vector preparations used in the study were quantified side-by-side before use. The primers used for qPCR on AAV genome annealed to BGH polyA (Fw: tctagttgccagccatctgttgt (SEQ ID NO: 44); Rev: tgg-gagtggcaccttcca (SEQ ID NO: 45) and codon-optimized hGAA (Fw: agatacgccggacattggactg (SEQ ID NO: 46); Rev: gcacgcccagcagattgaac (SEQ ID NO: 47). The AAV serotypes used is AAV8 (Zincarelli et al. Mol Ther. 2008 June; 16(6):1073-80).

In Vitro Experiments

Human hepatoma cells (HuH7) were seeded in 6-well plates ($5 \times 10^5$ cells/well) and transfected using Lipofectamine 3000 (Thermo Fisher Scientific) according to manufacturer's instructions. 72 hours after transfection, cells were harvested and analyzed for GAA activity and Western blot analyses. For the enzyme uptake experiments HuH7 cells were seeded in T75-well plates ($1 \times 10^7$ cells/well) and transfected using Lipofectamine 3000 (Thermo Fisher Scientific) accordingly to manufacturer's instructions. 72 hours after transfection, HuH7 conditioned media were harvested and used to culture fibroblasts derived from Pompe disease patients (GMO 20124 GSDII 3p). After 72 hours in culture the fibroblasts were washed 3 times with PBS, harvested and analyzed for Western blot analyses.

Mouse Studies

Wild type C57BL/6 mice were purchased from Charles River (Charles River, France). The Gaa−/− mouse was generated by targeted disruption of exon 6 (Raben N. et al. J Biol Chem. 1998 Jul. 24; 273(30):19086-92). Gaa−/− mice in the C57BL/6J/129X1/SvJ background were used. Male littermate affected Gaa−/− and unaffected Gaa+/+ mice were used. AAV vectors were delivered to: 1. adult mice via the tail vein in a volume of 0.2 ml. Experimental groups were sized to allow for statistical analysis; all the animals were included in the analysis and none of the outliers was excluded. Mice were assigned randomly to the experimental groups, and the operators who performed vector delivery and functional analyses were blinded to group identity.

GAA Activity

GAA activity was measured in mouse plasma (1/1000-1/2000 dilution) and tissues. Snap-frozen tissues were homogenized in di UltraPure™ DNase/RNase-Free Distilled Water (Thermo Fisher Scientific). 50-100 mg of tissue were weighed and homogenized, then centrifuged for 20 minutes at 10000×g to collect supernatant. The enzymatic reaction was set up using 10 μl of sample (plasma or tissue homogenate) and 20 μl of substrate—4MU-alpha-D-glucoside, in a 96 wells plate. The reaction mixture was incubated at 37° C. for one hour, and then stopped by adding 150 μl of Sodium Carbonate buffer pH 10.5. A standard curve (0-2500 pmol/μl of 4MU) was used to measure released fluorescent 4MU from individual reaction mixture, using the EnSpire alpha plate reader (Perkin-Elmer) at 449 nm (Emission) and 360 nm (Excitation). The protein concentration of the clarified supernatant was quantified by BCA (Thermo Fisher Scientific). To calculate the GAA activity, released 4MU concentration was divided by the sample protein concentration and activity was reported as nmol/hour/mg protein.

Western Blot Analyses

HuH7 and Fibroblasts cell lysates were prepared using 10 mM PBS (pH7.4) containing 1% of Triton-X100 and protease inhibitors (Roche Diagnosis). Western blot on mouse plasma was performed on samples diluted 1:4 in distilled water. Mouse tissues were prepared as indicated for GAA activity. Protein concentration was determined using the BCA Protein Assay (Thermo Fisher Scientific). SDS-page electrophoresis was performed in a 4-12% polyacrylamide gel. After transfer the membrane was blocked with Odyssey buffer (Li-Cor Biosciences) and incubated with an anti-GAA antibody (rabbit monoclonal, Abcam), or anti-vinculin (mouse monoclonal, Sigma Aldrich). The membrane was washed and incubated with the appropriate secondary antibody (Li-Cor Biosciences), and visualized by Odyssey imaging system (Li-Cor Biosciences).

Anti-GAA Antibody Detection

Anti-GAA antibody measurement was performed according to a published protocol. Briefly, maxisorp 96 wells plates (Thermo Fisher Scientific) were coated with 1 μg/ml of rhGAA. IgG standard curves were made by serial 1 to 2 dilutions of commercial mouse (Sigma Aldrich) recombinant IgG which were coated directly onto the wells in duplicate. Anti-mouse (Southern biotech) IgG secondary antibodies were used as secondary antibodies.

Results

1. Cloning of the GAA Variant in AAV Plasmids

We selected initially five heterologous domains to improve CNS targeting of GAA: 1. the Apolipoprotein B domain (ApoB), 2. the Apolipoprotein E domain (ApoE), 3. Spadin, 4. Neurotensin amino acid 1-13 (NT1-13); Neurotensin amino acid 9-13 (NT9-13). The ApoB and ApoE domains are ligands of LDL receptors and have been previously described to enhance CNS targeting when conjugated to proteins (Bockenhoff A. et al., J. Neurosci., 2014, vol. 34, no. 9, pp. 3122-3129; Sorrentino N. C. et al., EMBO Mol. Med., 2013, vol. 5, no. 5, pp. 675-690; Spencer et al., PNAS 2007; vol. 104, no. 18, pp. 7594-7599; Gleitz H. F. E. et al, EMBO Mol Med. 2018). The Spadin peptide, NT1-13 and NT9-13, which are Sortilin ligands, have instead never conjugated to other protein and/or exploited for their targeting to the CNS.

The ApoB, ApoE, Spadin, NT1-13 and NT9-13 peptides were inserted at the N-terminus of the sp7-Δ42-GAAco variant [Puzzo F., et al., Sci Transl Med. 2017 Nov. 29; 9 (418), patent application WO2018/046774)] to generate the: sp7-ApoB-Δ42-GAAco variant (abbreviated as HD-ApoB), the sp7-ApoE-Δ42-GAAco variant (abbreviated as HD-ApoE), the sp7-Spadin-Δ42-GAAco variant (abbreviated as HD-Spadin), the sp7-NT1-13-Δ42-GAAco variant (abbreviated as HD-NT1-13) Spadin), the sp7-NT9-13-Δ42-GAAco variant (abbreviated as HD-NT9-13) (FIG. 1). An aminoacidic linker (3 aminoacids, Maga J A, et al., J Biol Chem. 2013; 288(3):1Δ28-1438.) was placed between the stability domains and the GAA to ensure proper enzyme folding (FIG. 1).

To achieve efficient expression in the liver, all the sp7-Δ42-GAAco variants were cloned in an expression cassette under the control of the hepatocyte-restricted Apolipopro-tein (ApoE) enhancer with human alpha-1 anti-trypsin (hAAT) promoter. All the transgenes expression cassette encoding for the sp7-Δ42-GAAco variants contained the same previously described regulatory elements [Puzzo F., et al., Sci Transl Med. 2017 Nov. 29; 9 (418); FIG. 1):

an AAV cis-packaging backbone containing two ITR sequences from AAV2, required for the packaging of the viral genome, the apolipoprotein E (ApoE) hepatocyte control region enhancer the hepatocyte-specific human alpha 1-antitrypsin (hAAT) promoter human haemoglobin I3-subunit synthetic intron (HBB2.1) to stabilize the mRNA and enhance protein expression, a codon optimized version of the GAA coding sequence devoid of the endogenous signal peptide an heterologous signal peptide to allow the GAA secretion (sp7)

the bovine growth hormone (bGH) polyadenylation signal.

2. Analysis of the GAA Variants in Human Hepatocyte Cell Cultures

The production and enzymatic activity of the GAA variants with the heterologous domains [sp7-ApoB-Δ42-GAAco (HD-ApoB), sp7-ApoE-Δ42-GAAco (HD-ApoE), sp7-Spadin-Δ42-GAAco (HD-Spadin), sp7-NT1-13-Δ42-GAAco (HD-NT1-13), sp7-NT9-13-Δ42-GAAco variant (HD-NT9-13)] were first tested in a human hepatocyte cell line (HuH7) in culture by transient transfection of the respective pAAV plasmids. The variant devoid of heterologous domains (sp7-Δ42-GAAco, abbreviated as HD0) was used as positive control. Three independent transient transfections of HuH7 cells were performed (FIG. 2). Cells were harvested 72 h after transfection and GAA enzyme activity was measured in cell lysates (FIG. 2). Compared to HD0, only the HD-Spadin, HD-NT1-13 and HD-NT9-13 variants showed a preserved enzymatic activity in cell lysates indicating proper enzyme production and maturation (FIG. 2). The HD-ApoE resulting in undetectable GAA activity in cells (FIG. 2) was not further analyzed.

3. Analysis of the GAA Variants in the GAA Knock-Out (GAA–/–) Mouse Model of Pompe Disease Following AAV-Mediated Liver Gene Transfer We tested the therapeutic efficacy of the chimeric HD-ApoB and HD-Spadin GAA variant in the Gaa–/– mouse model of Pompe disease following AAV liver gene transfer. We generated AAV8 vectors encoding for each variant: sp7-ApoB-Δ42-GAAco (HD-ApoB) and sp7-Spadin-Δ42-GAAco (HD-Spadin). AAV8 vectors encoding for the GAA variant devoid of heterologous domains sp7-Δ42-GAAco (HD0) was used as positive control. The AAV8 vectors were produced as they efficiently transduce mouse hepatocytes. Two-month-old Gaa–/– mice (n=6/group) were injected intravenously with AAV8 vectors encoding for HD-ApoB, HD-Spadin or HD0 as comparison (vector dose: $5 \times 10^{11}$ vg/kg). Littermate Gaa–/– mice (n=6) treated with PBS were used as affected controls (Ctrl). Littermate Gaa+/+ mice (n=5) were used as unaffected controls. The study follow-up was 4 months.

Plasma samples collected and analyzed at 4 months after treatment to measure circulating GAA activity (FIG. 3) and protein amount (FIG. 4). Circulating GAA activity was not significantly different between HD-Spadin and HD0, while significantly lower activity was achieved in the HD-ApoB treatment group (FIG. 3). Secretion of GAA in the circulation was readily confirmed in the plasma of all mice treated with AAV vectors at the end of the study (4 months after treatment) by Western blot analyses with anti-GAA antibody (FIG. 4A). GAA band quantification (FIG. 4B) showed no significant differences between HD-Spadin and HD0, while significantly lower amount of enzyme was achieved in the HD-ApoB treatment group (FIG. 4B), confirming the activity data (FIG. 3). Overall these data suggest that the chimeric HD-Spadin variant is efficiently produced and secreted by hepatocytes after AAV liver gene transfer and has preserved enzymatic activity.

Then, to evaluate the therapeutic efficacy of the chimeric GAA variants we measured glycogen content in the brain (FIG. 5). Notably, in the brain, glycogen clearance was significantly improved in Gaa–/– mice treated with HD-Spadin vectors compared to both HD-ApoB and HD0 vectors (FIG. 5). These results demonstrate the superiority of the HD-Spadin chimeric polypeptide, in terms of brain uptake and GAA activity in the brain.

Glycogen content was also measured in muscle (heart, triceps) and spinal cord (FIG. 6). As expected, glycogen content was increased in all tissues of PBS-treated Gaa–/– mice compared to Gaa+/+ (FIG. 6). Significant glycogen clearance was observed in the muscle and CNS of all AAV-treated cohorts (FIG. 6). However, glycogen content in the CNS of AAV-treated Gaa–/– mice was still higher than that measured in Gaa+/+. Notably, glycogen clearance was significantly improved in the spinal cord of Gaa–/– mice treated with HD-Spadin vectors compared to HD-ApoB vectors (FIG. 6C).

Finally, we evaluated the immunogenicity of the HD-Spadin variant by measuring anti-GAA immunoglobulin G (IgG) in mouse plasma at 1 and 4 months after vector administration (FIG. 7). No significant anti-GAA humoral immune response was observed in mice treated with HD-Spadin variant compared to HD0 (FIG. 7). Low (<1 μg/mL) and sporadic anti-GAA IgG were detected at 1 month but they came back to 0 at the end of the study (FIG. 7), as observed in a previous study of AAV liver gene transfer with secretable GAA [Puzzo F., et al., Sci Transl Med. 2017 Nov. 29; 9 (418)].

In addition, uptake of the chimeric GAA variant in Pompe disease fibroblasts in culture was evaluated. It was shown that the HD-spadin variant was readily internalized and maturated within the cells (data not shown).

In conclusion, the chimeric GAA variant containing the Spadin heterologous domain (abbreviated as HD-Spadin) resulted in preserved GAA enzyme secretion and enzyme activity and in improved correction of the pathological accumulation of glycogen in the CNS, in particular in the brain, in the absence of immune response in a mouse model of Pompe disease.

The invention claimed is:

1. A nucleic acid molecule encoding a chimeric polypeptide comprising a peptide of interest fused to one or more heterologous moieties, wherein at least one of the heterologous moieties is a ligand of the Sortilin receptor, and said heterologous moiety is a Spadin peptide encoded by the nucleotide sequence of SEQ ID NO: 14 or by a nucleotide sequence having at least 85% identity to the nucleotide sequence of SEQ ID NO: 14.

2. The nucleic acid molecule according to claim 1, wherein the peptide of interest is a functional GAA polypeptide encoded by a nucleotide sequence selected from the group consisting of SEQ ID NOs: 1-3 or by a nucleotide sequence having at least 85% identity to a nucleotide sequence selected from the group consisting of SEQ ID NOs: 1-3.

3. The nucleic acid molecule according to claim 1, wherein the peptide of interest is a functional truncated GAA polypeptide.

4. The nucleic acid molecule according to claim 1, wherein the heterologous moiety is fused at the N-terminal end of the peptide of interest.

5. The nucleic acid molecule according to claim 1, further comprising a signal peptide having an amino acid sequence selected from the group consisting of SEQ ID NOs: 18-22.

6. A nucleic acid construct comprising the nucleic acid molecule according to claim 1 operably linked to a promoter, wherein said nucleic acid construct optionally further comprises an intron.

7. The nucleic acid construct according to claim 6, comprising: a promoter; an intron; the nucleic acid molecule; and a polyadenylation signal.

8. A viral vector comprising the nucleic acid molecule of claim 1 or a nucleic acid construct thereof.

9. The vector according to claim 8, which is a single-stranded or double-stranded self-complementary AAV vector.

10. An isolated cell transformed with the nucleic acid molecule according to claim 1 or a nucleic acid construct comprising said nucleic acid molecule or a vector comprising said nucleic acid construct or said nucleic acid molecule.

11. A chimeric polypeptide encoded by the nucleic acid molecule according to claim 1.

12. A pharmaceutical composition, comprising, in a pharmaceutically acceptable carrier, the nucleic acid molecule according to claim 1, a nucleic acid construct comprising said nucleic acid molecule, a vector comprising said nucleic acid construct or said nucleic acid molecule, a cell comprising said nucleic acid molecule, nucleic acid construct or said vector, or a chimeric polypeptide encoded by said nucleic acid molecule.

13. A method of treating GSD II (Pompe disease) comprising the administration of a pharmaceutical composition according to claim 12 to a subject in need of treatment, wherein the nucleic acid molecule encoding the chimeric polypeptide comprises a nucleic acid sequence encoding a functional GAA polypeptide, said nucleic acid sequence being selected from the group consisting of SEQ ID NOs: 1-3 or by a nucleotide sequence having at least 85% identity to a nucleotide sequence selected from the group consisting of SEQ ID NOs: 1-3.

* * * * *